United States Patent
Keith et al.

(10) Patent No.: US 8,915,938 B2
(45) Date of Patent: *Dec. 23, 2014

(54) APPARATUS AND METHOD FOR TREATMENT OF SINUSITIS

(75) Inventors: Peter T. Keith, Lanesboro, MN (US); Theodore O. Truitt, St. Cloud, MN (US); Thomas V. Ressemann, St. Cloud, MN (US); John R. Drontle, Monticello, MN (US); Joel R. Munsinger, Blaine, MN (US); Anthony J. Hanson, St. Cloud, MN (US)

(73) Assignee: Entellus Medical Inc., Maple Grove, MN (US)

( * ) Notice: Subject to any disclaimer, the term of this patent is extended or adjusted under 35 U.S.C. 154(b) by 272 days.

This patent is subject to a terminal disclaimer.

(21) Appl. No.: 13/237,398

(22) Filed: Sep. 20, 2011

(65) Prior Publication Data

US 2012/0010646 A1    Jan. 12, 2012

Related U.S. Application Data

(63) Continuation of application No. 11/623,740, filed on Jan. 16, 2007, now abandoned.

(51) Int. Cl.
| | | |
|---|---|---|
| *A61M 29/02* | (2006.01) | |
| *A61B 1/00* | (2006.01) | |
| *A61B 17/34* | (2006.01) | |
| *A61B 17/24* | (2006.01) | |

(52) U.S. Cl.
CPC ........ *A61M 29/02* (2013.01); *A61B 2017/3425* (2013.01); *A61B 1/00154* (2013.01); *A61B 2017/3445* (2013.01); *A61B 17/3431* (2013.01); *A61B 17/3496* (2013.01); *A61B 17/24* (2013.01); *A61B 2017/246* (2013.01); *A61B 17/3421* (2013.01)
USPC ........................................ 606/196

(58) Field of Classification Search
USPC ............ 606/190–199; 604/514, 506; 424/434
See application file for complete search history.

(56) References Cited

U.S. PATENT DOCUMENTS

| | | | |
|---|---|---|---|
| 2,525,183 A | 10/1950 | Robison | |
| 3,800,788 A | 4/1974 | White | |

(Continued)

FOREIGN PATENT DOCUMENTS

| | | |
|---|---|---|
| EP | 0129634 A1 | 1/1985 |
| EP | 1598015 A1 | 11/2005 |

(Continued)

OTHER PUBLICATIONS

Petersen, Robert J., Canine Fossa Puncture, The Laryngoscope Office, Oct. 5, 1972, pp. 369-371.

(Continued)

*Primary Examiner* — Ryan Severson
*Assistant Examiner* — Anh Dang
(74) *Attorney, Agent, or Firm* — Vista IP Law Group LLP

(57) ABSTRACT

A method of treating a constricted sinus passageway of a patient includes traversing the canine fossa region of the patient so as to form a passageway in the sinus cavity. A cannula is positioned in the passageway. A visualization tool such as an endoscope is passed through a lumen or channel in the cannula to aid in visualization of the anatomical site of interest. A balloon dilation catheter is then deployed through or along the cannula so as to place the balloon within or across the constricted anatomical space (e.g., ostium). The balloon is then expanded so as to expand at least a portion of the constricted anatomical space. Alternative embodiments include the use of an optional guide wire and incorporating a endoscope lumen through the balloon dilation catheter.

18 Claims, 39 Drawing Sheets

(56) References Cited

U.S. PATENT DOCUMENTS

| | | | |
|---|---|---|---|
| 4,737,141 A | 4/1988 | Spits | |
| 5,021,043 A | 6/1991 | Becker et al. | |
| 5,024,658 A | 6/1991 | Kozlov et al. | |
| 5,169,386 A | 12/1992 | Becker et al. | |
| 5,645,528 A | 7/1997 | Thome | |
| 5,795,325 A | 8/1998 | Valley et al. | |
| 5,964,767 A | 10/1999 | Tapia et al. | |
| 6,083,188 A | 7/2000 | Becker | |
| 6,090,132 A | 7/2000 | Fox | |
| 6,113,567 A | 9/2000 | Becker | |
| 6,143,016 A | 11/2000 | Bleam et al. | |
| 6,238,364 B1 | 5/2001 | Becker | |
| 6,264,670 B1* | 7/2001 | Chin | 606/190 |
| 6,491,940 B1 | 12/2002 | Levin | |
| D501,677 S | 2/2005 | Becker | |
| 6,851,424 B2 | 2/2005 | Scopton | |
| 7,169,161 B2 | 1/2007 | Bonnette et al. | |
| 7,419,497 B2 | 9/2008 | Muni et al. | |
| 7,520,876 B2* | 4/2009 | Ressemann et al. | 604/510 |
| 7,842,062 B2 | 11/2010 | Keith et al. | |
| 7,879,061 B2 | 2/2011 | Keith et al. | |
| 7,918,871 B2 | 4/2011 | Truitt et al. | |
| 8,241,266 B2 | 8/2012 | Keith et al. | |
| 8,348,969 B2 | 1/2013 | Keith et al. | |
| 8,568,439 B2 | 10/2013 | Keith et al. | |
| 8,585,728 B2 | 11/2013 | Keith et al. | |
| 8,585,729 B2 | 11/2013 | Keith et al. | |
| 8,623,043 B1 | 1/2014 | Keith et al. | |
| 2001/0014439 A1 | 8/2001 | Meller et al. | |
| 2002/0072729 A1 | 6/2002 | Hoste et al. | |
| 2002/0138121 A1 | 9/2002 | Fox | |
| 2003/0045834 A1 | 3/2003 | Wing et al. | |
| 2004/0064083 A1 | 4/2004 | Becker | |
| 2004/0064150 A1 | 4/2004 | Becker | |
| 2005/0240147 A1 | 10/2005 | Makower et al. | |
| 2005/0245906 A1 | 11/2005 | Makower | |
| 2006/0004286 A1 | 1/2006 | Chang et al. | |
| 2006/0004323 A1* | 1/2006 | Chang et al. | 604/28 |
| 2006/0063973 A1 | 3/2006 | Makower et al. | |
| 2006/0095066 A1 | 5/2006 | Chang et al. | |
| 2006/0100687 A1 | 5/2006 | Fahey et al. | |
| 2006/0106361 A1 | 5/2006 | Muni et al. | |
| 2006/0149310 A1 | 7/2006 | Becker | |
| 2006/0173298 A1 | 8/2006 | Tucker | |
| 2006/0210605 A1 | 9/2006 | Chang et al. | |
| 2006/0235458 A1* | 10/2006 | Belson | 606/191 |
| 2008/0015472 A1 | 1/2008 | Ressemann et al. | |
| 2009/0216196 A1 | 8/2009 | Drontle et al. | |
| 2011/0288477 A1 | 11/2011 | Ressemann et al. | |
| 2012/0283625 A1 | 11/2012 | Keith et al. | |

FOREIGN PATENT DOCUMENTS

| | | |
|---|---|---|
| WO | WO 91/17787 A1 | 11/1991 |
| WO | WO 02/082978 A2 | 10/2002 |
| WO | WO 2005/086945 A2 | 9/2005 |

OTHER PUBLICATIONS

Elidan, J., MD., Irrigation of the Maxillary Sinus by Canine Fossa Puncture Experience with 202 Patients, Ann Otol Rhinol Laryngol, 92:1983, pp. 528-529.

Yanagisawa, Eiji, et al., Trans-Canine-Fossa Maxillary Sinoscopy for Biopsy Via the Stammberger Technique, ENT Rhinoscopic Clinic, Aug. 2001 Rhino, pp. 1-3.

Yanagisawa, Eiji, et al., Powered Endoscopic Inferior Meatal Antrostomy Under Canine Fossa Telescopic Guidance, ENT-Ear, Nose & Throat Journal, Sep. 2001, pp. 618-620.

Sathananthar, Shanmugam, et al., Canine Fossa Puncture and Clearance of the Maxillary Sinus for the Severely Diseased Maxillary Sinus, The Laryngoscope 115: Jun. 2005, pp. 1026-1029.

Robinson, Simon, et al., Patterns of Innervation of the Anterior Maxilla: A Cadaver Study with Relevance to Canine Fossa Puncture of the Maxillary Sinus, Laryngoscope 115: Oct. 2005, pp. 1785-1788.

Bolger, William, E., et al., Catheter-Based Dilation of the Sinus Ostia: Initial Safety and Feasibility Analysis in a Cadaver Model, Maryland Sinus Clinic, Bethesda, Maryland, and California Sinus Institute, Palo Alto, California, OceanSide Publications, Inc., May-Jun. 2006, vol. 20, No. 3, pp. 290-294.

Friedman, Michael, M.D. et al., Functional Endoscopic Dilatation of the Sinuses (FEDS): Patient Selection and Surgical Technique, Operative Technologies in Otolaryngology, vol. 17, No. 2, Jun. 2006, pp. 126-134.

Jones, Nick, Commentary on "Safety and Feasibility of Balloon Catheter Dilation of Paranasal Sinus Ostia: A Preliminary Investigation", Annals of Otology, Rhinology & Laryngology 115(4), pp. 300-301 (2006).

Bolger, William E., Commentary Misconceptions Regarding Balloon Catheter Dilation of Paranasal Sinus Ostia, Annals of Otology, Rhinology & Laryngology 115(10): 791-792 (2006).

Lanza, Donald, C., et al., Commentary Balloon Sinuplasty: Not Ready for Prime Time, Annals of Otology, Rhinology & Laryngology 115(10): 789-790 (2006).

Brown, Christopher, L. et al., Safety and Feasibility of Balloon Catheter Dilation of Paranasal Sinus Ostia: A Preliminary Investigation, Annals of Otology, Rhinology & Laryngology 115(4):293-299 (2006).

Gottman, D., et al., Balloon Dilatation of Recurrent Ostia Occlusion of the Frontal Sinus, ECR Mar. 3, 2001, 2:-3:30 PM, Vienna Austria (1p).

Gottman et al., "Balloon Dilation of Recurrent Ostial Occlusion of the Frontal Sinus", Gottmann et al. Abstract (B-0453) Mar. 2001, 22 pages.

Entellus Medical, (510(k) Premarket Notification cover letter and Attachment B: Predicate Device Labeling, dated Aug. 15, 2007.

Iro, H., J. Zenk. "A new device for frontal sinus endoscopy: First Clinical Report", Department of Otorhinolaryngology, University of Eralngen-Nuremberg, Germany. Otorhinolaryngology, Head and Neck Surgery vol. 125 No. 6, Dec. 2001, pp. 613-616 (4 pages).

Office Communication, Extended European Search report dated Jun. 18, 2010 for Application No. 07866014.9 PCT/US2007/088834, Applicant: Entellus Medical, Inc., EPO forms 1503 03.82, P0459, and 1703 01 (7 pages).

R. Peterson, Sinus Puncture Therapy; Canine Fossa Puncture Method "How I Do It" Head and Neck, The Laryngoscope 91: Dec. 1981 pp. 2126-2128.

T.G.A. Ijaduola, Use of a Foley Catheter for Short-Tern Drainage of Frontal Sinus Surgery, Journ. of Laryngology and Otology, Apr. 1989, vol. 103, pp. 375-378.

A. Gatot et al., Early Treatment of Oribital Floor Fractures with Catheter Balloon in Children, Inti. J. of Ped. Otorhinolaryngology, 21 (1991) 97-101.

D.I. Tarasov et al., Treatment of Chronic Ethmoiditis by IntraCellular Administration of Medicines to the Ethmoidal Labyrinth, Vestn Otorinolaringol. Nov.-Dec. 1978; (6):45-47 (Abstract in English).

J. M. Robison, Pressure Treatment of Maxillary Sinusitis, J.A.M.A., May 31, 1952, pp. 436-440.

J. M. Robison, Pressure Treatment of Purulent Maxillary Sinusitis, Texas State Journal of Medicine, May 1952, pp. 281-288.

Entellus Medical, 51O(k) Letter (Amendment 1) and Attachments D & E, dated Mar. 13, 2008.

PCT International Preliminary Report on Patentability (Chapter I of the Patent Cooperation Treaty) for PCT/US2007/066187, Applicant: Entellus Medical, Inc., Form PCT/IB/326 and 373, dated Oct. 21, 2008 (6 pages).

PCT International Preliminary Report on Patentability (Chapter I of the Patent Cooperation Treaty) for PCT/US2007/088834, Applicant: Entellus Medical, Inc., Form PCT/IB/326 and 373, dated Jul. 30, 2009 (9 pages).

(56) References Cited

OTHER PUBLICATIONS

PCT International Search Report for PCT/US2007/088834, Applicant: Entellus Medical, Inc., Forms PCT/ISA/220 and PCT/ISA/210, dated May 20, 2008 (4 pages).
PCT Written Opinion for PCT/US2007/088834, Applicant: Entellus Medical, Inc., Form PCT/ISA/237, dated May 20, 2008 (10 pages).
PCT International Search Report for PCT/US2007/66187, Applicant: Entellus Medical, Inc., Forms PCT/ISA/220 and PCT/ISA/210, dated Apr. 17, 2008 (5 pages).
PCT Written Opinion for PCT/US2007/66187, Applicant: Entellus Medical, Inc., Form PCT/ISA/237, dated Apr. 17, 2008 (5 pages).

* cited by examiner

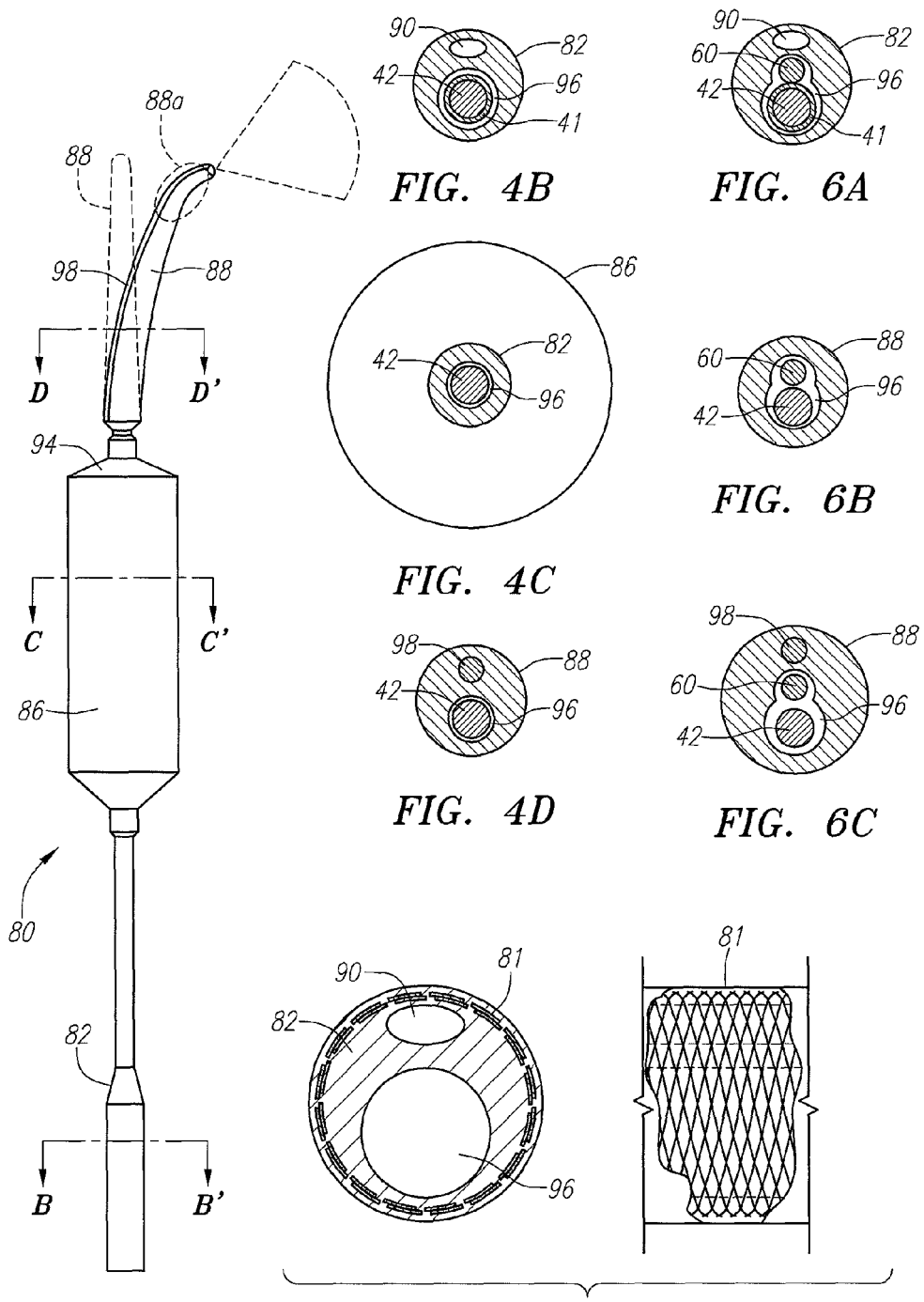

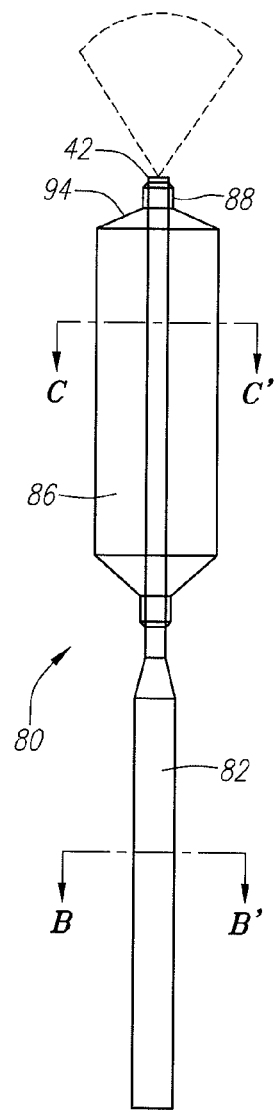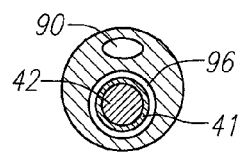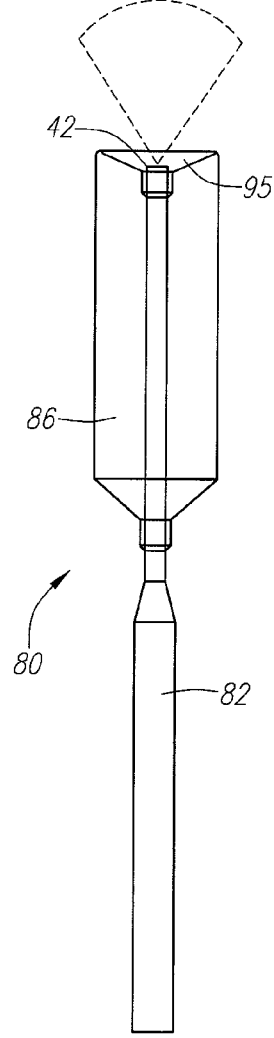
FIG. 7A
FIG. 7B
FIG. 7C
FIG. 7D

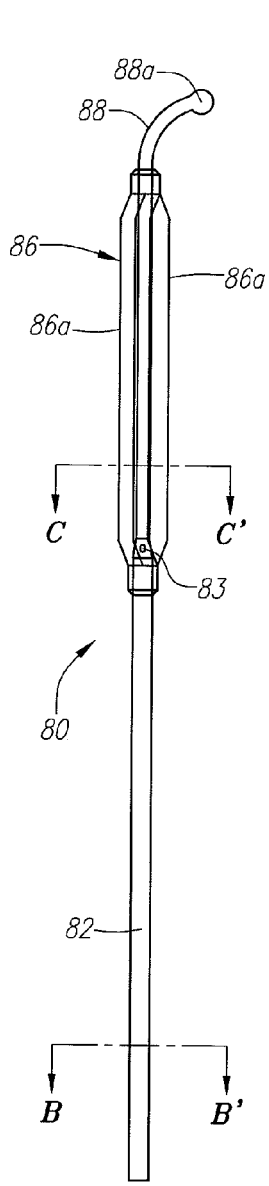
FIG. 8A
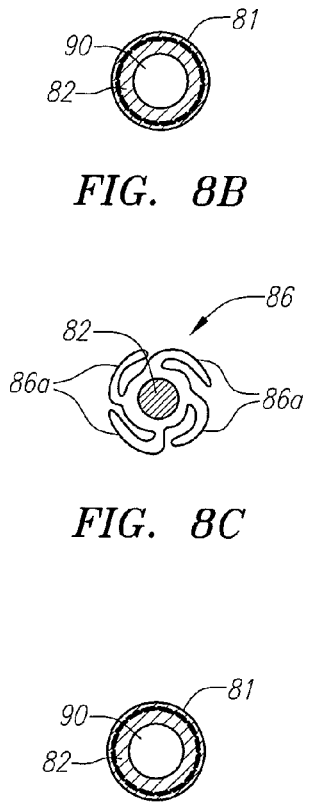
FIG. 8B
FIG. 8C
FIG. 8E
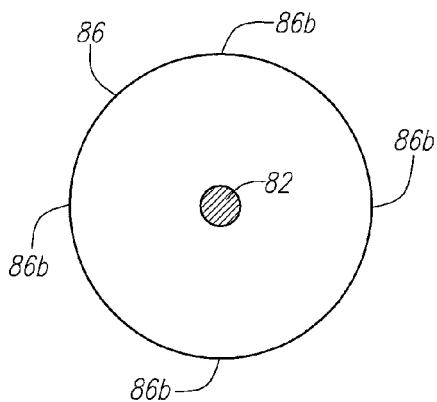
FIG. 8F
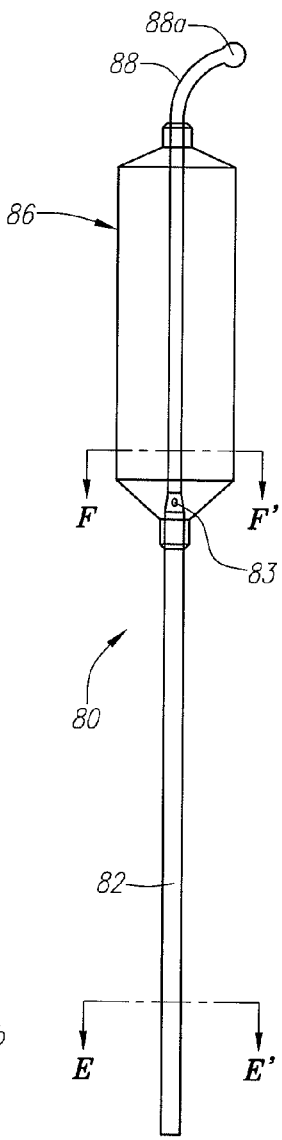
FIG. 8D

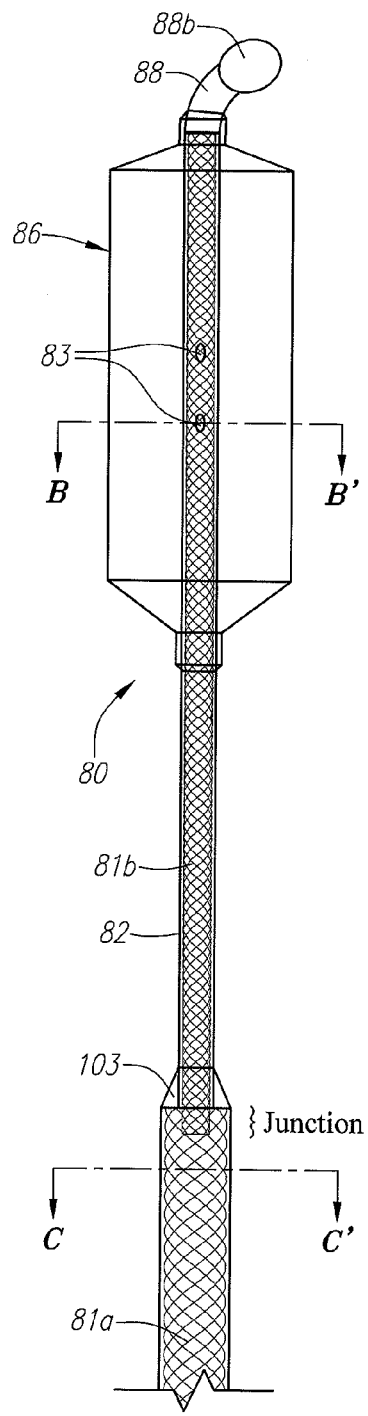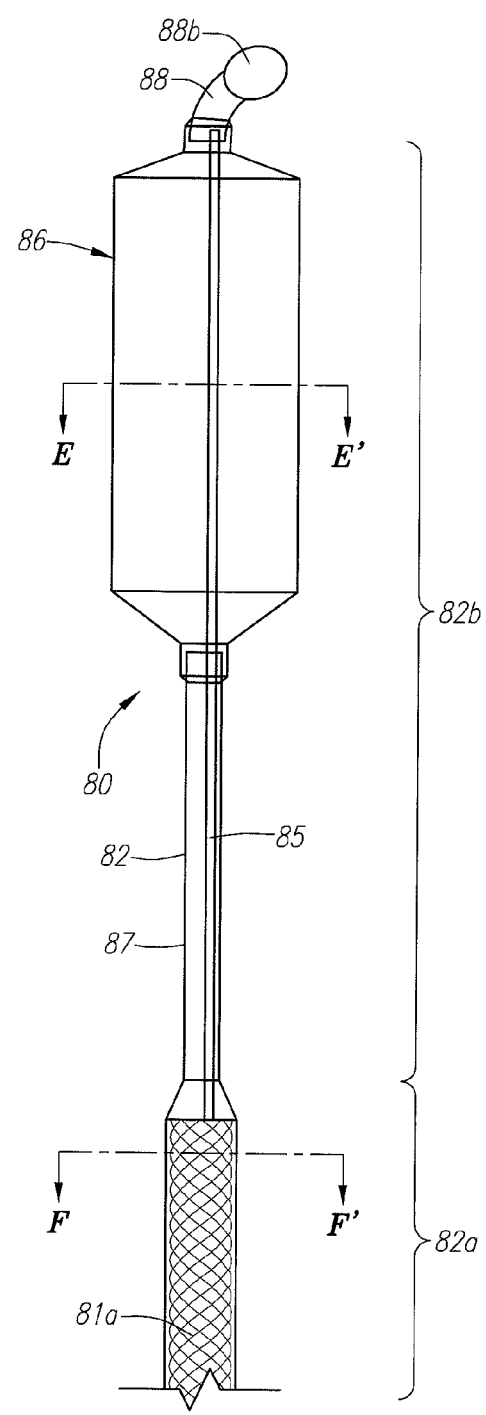
FIG. 11A                    FIG. 11D

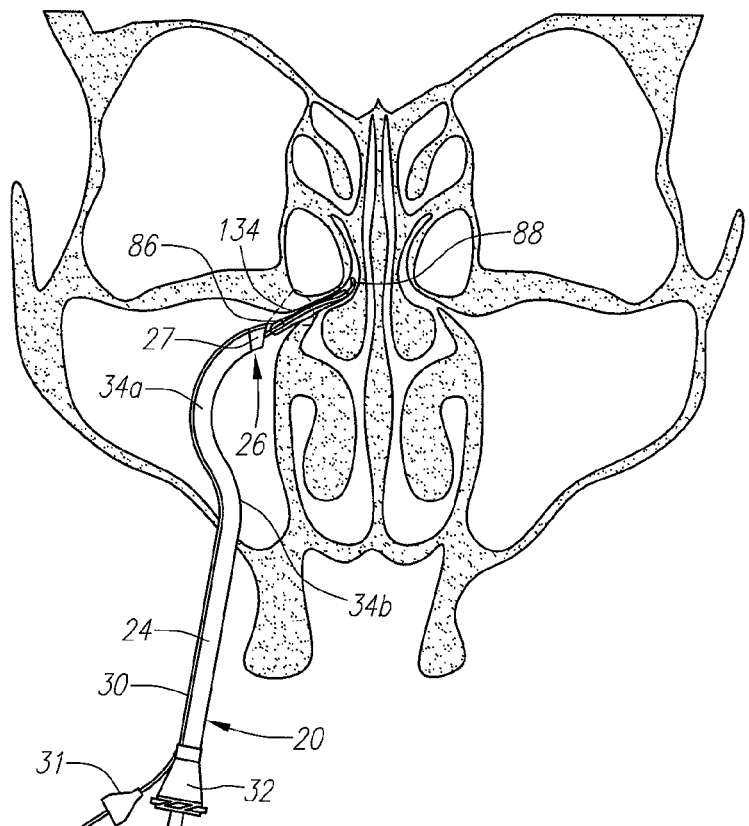
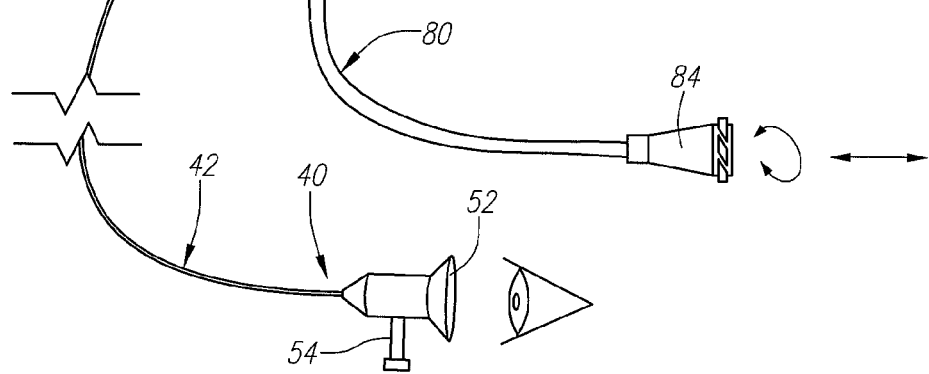
FIG. 24

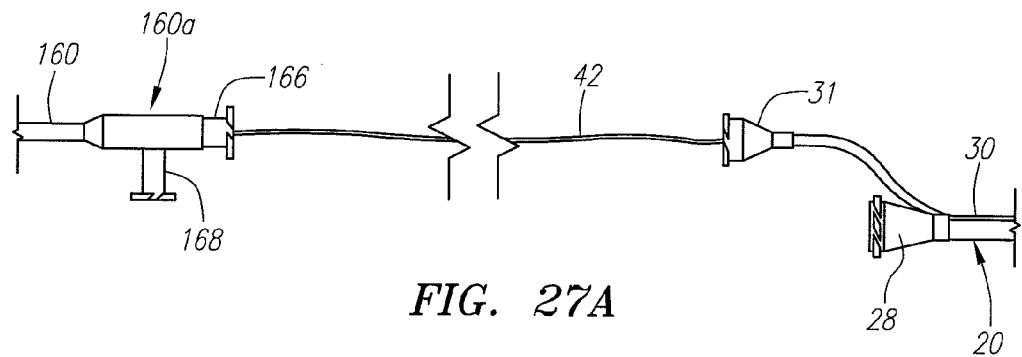
FIG. 27A
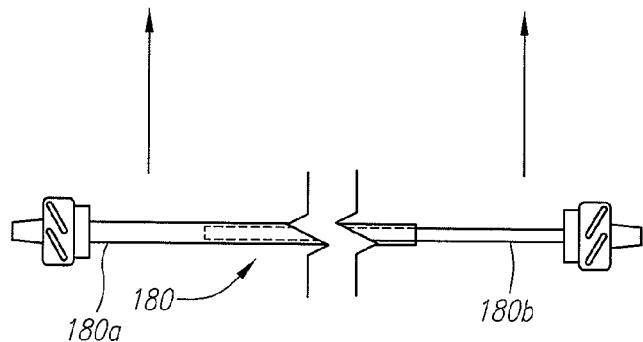
FIG. 27B
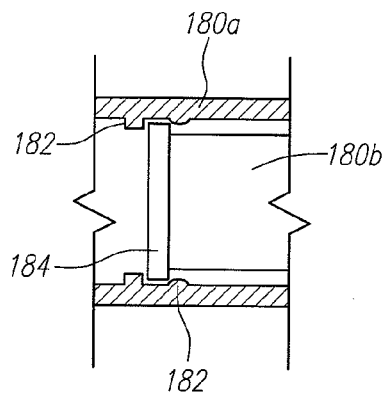
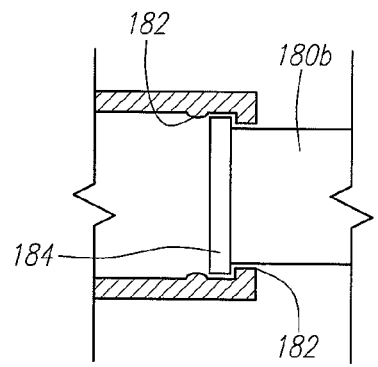
FIG. 28A      FIG. 28B

APPARATUS AND METHOD FOR TREATMENT OF SINUSITIS

FIELD OF THE INVENTION

The field of the invention generally relates to devices and methods for the treatment or amelioration of sinusitis.

BACKGROUND OF THE INVENTION

Sinusitis is a condition affecting over 35 million Americans, and similarly large populations in the rest of the developed world. Sinusitis occurs when one or more of the four paired sinus cavities (i.e., maxillary, ethmoid, frontal, sphenoid) becomes obstructed. Normally the sinus cavities, each of which are lined by mucosa, produce mucous which is then moved by beating cilia from the sinus cavity out to the nasal cavity and down the throat. The combined sinuses produce approximately one liter of mucous daily, so the effective transport of this mucous is important to sinus health.

Each sinus cavity has an opening into the nasal passage called an ostium. When the mucosa of one or more of the ostia or regions near the ostia become inflamed, the egress of mucous is interrupted, setting the stage for an infection of the sinus cavity, i.e., sinusitis. Infections of the maxillary and/or ethmoid sinuses make up the vast majority of cases of sinusitis, with far fewer cases involving the sphenoids and frontals.

Though many instances of sinusitis may be treatable with antibiotics, in some cases sinusitis persists for months, a condition called chronic sinusitis. Some patients are also prone to multiple episodes of sinusitis in a given period of time, a condition called recurrent sinusitis.

Currently, patients experiencing chronic sinusitis are eligible to have a surgical procedure called functional endoscopic sinus surgery (FESS). In this procedure, which almost always done in an operating room setting with the patient under general anesthesia, surgical cutting instruments are guided with an endoscopic visualization tool to the various sinus ostia and adjacent regions. Inflamed mucosa and underlying bony tissue are cut away in an effort to widen the outlet of the sinuses of interest. Once opened, the infected sinuses are able to drain and return to a relatively normal state.

While this procedure is generally effective, it is a relatively invasive procedure to the nasal cavity and sinuses. There can be significant post-operative pain for the patient, and sometimes there are bleeding complications that require packing to be placed in the nasal cavity. Subsequent removal of this packing can be quite painful. Also, since the nasal and sinus tissue are significantly traumatized, it may take several days to weeks to know whether the surgery was successful.

Additionally, in certain patients, the ostial regions of the surgically-treated sinuses can become re-obstructed with excess growth of scar tissue as a result of the tissue trauma. When the advantages and disadvantages of the surgery are considered for a patient with sinusitis, there are many patients in whom the surgery may not be appropriate. For example, their condition may not be considered severe enough or extensive enough to warrant FESS surgery. In other situations, the patient may have "recurrent acute" sinusitis, rather than "chronic" sinusitis, and FESS surgery may not be warranted. In still other situations, the patient may be fearful of the pain or other aspects of having FESS performed. Alternatively, the FESS procedure may be too costly for a particular patient.

For these and other reasons, there is a clear need for better methods and devices for the treatment of sinusitis.

SUMMARY OF THE INVENTION

In a first aspect of the invention, a method of treating sinusitis in a patient includes forming an artificial access passageway into a sinus cavity of the patient. A cannula is then positioned within the access passageway, the cannula having a first lumen adapted for passage of a balloon dilation catheter, and a secondary lumen adapted for passage of a visualization tool. The visualization tool is inserted into the secondary lumen and the anatomical region of interest is visualized. Next, the balloon dilation catheter is inserted into the first lumen and advanced so as to place the dilation balloon in or across the anatomical region of interest. The dilation balloon is then dilated.

In another aspect of the invention, a system for treatment of sinusitis in a patient includes a piercing tool for creating an artificial access passageway to a sinus cavity of the patient. The system further includes a cannula having a first lumen adapted for passage of a balloon dilation catheter, and a secondary lumen adapted for passage of a visualization tool. The system also includes a balloon dilation catheter having an expandable balloon on a distal region thereof, the balloon dilation catheter being dimensioned for passage through the first lumen of the cannula. The system may be sold as a kit or, alternatively, one or more sub-components of the overall system may be sold separately or in combination.

In still another embodiment, a system for treatment of sinusitis in a patient includes a sheath for maintaining a working lumen through an artificial access passageway to a sinus cavity of the patient. The system further includes a cannula having a first lumen adapted for passage of a balloon dilation catheter, and a secondary lumen adapted for passage of a visualization tool. The system includes a balloon dilation catheter having an expandable balloon on a distal region thereof, the balloon dilation catheter being dimensioned for passage through the first lumen of the cannula. As with the prior embodiment, the system may be sold as a kit or, alternatively, one or more sub-components of the overall system may be sold separately or in combination.

In another embodiment, a system for treatment of sinusitis in a patient includes a piercing tool for creating an artificial access passageway to a sinus cavity of the patient. A cannula is also provided that has a lumen adapted for passage of a visualization tool and a balloon dilation catheter at the same time. The balloon dilation catheter has an expandable balloon on a distal region thereof and a lumen adapted for receiving the visualization tool. The system may be sold as a kit or in one or more sub-components or combinations as described herein.

In still another embodiment, a method of treating sinusitis in a patient includes forming an artificial access passageway into a sinus cavity of the patient. A cannula is positioned within the access passageway, the cannula having a lumen adapted for receiving a visualization tool and a balloon dilation catheter. A balloon dilation catheter is then advanced through the lumen of the cannula with the dilation balloon in a collapsed state. The visualization tool is advanced through a lumen in the balloon dilation catheter and an anatomical region of interest is then visualized with the visualization tool. The balloon dilation catheter is then advanced to place the dilation balloon in or across the anatomical region of interest and the dilation balloon is dilated (e.g., inflated).

In still another embodiment, a method of treating sinusitis in a patient includes forming an artificial access passageway into a sinus cavity of the patient and positioning a cannula within the access passageway. The cannula has a first lumen adapted for passage of a balloon dilation catheter and also includes an integrated visualization tool. An anatomical region of interest is then visualized with the visualization tool. The balloon dilation catheter is then inserted into the first lumen and advanced so as to place the dilation balloon in or across the anatomical region of interest. The dilation balloon is then dilated.

In yet another embodiment, a system for treatment of sinusitis in a patient includes a piercing tool for creating an artificial access passageway to a sinus cavity of the patient. The system also includes a cannula having a first lumen adapted for passage of a balloon dilation catheter. A visualization tool is also secured to the cannula. The system includes a balloon dilation catheter having an expandable balloon on a distal region thereof, the balloon dilation catheter being dimensioned for passage through the first lumen of the cannula.

A balloon dilation catheter for dilating an anatomical structure associated with paranasal sinus drainage including an elongate tubular shaft having a proximal end and a distal end and a lumen extending therethrough. The balloon dilation catheter includes an inflatable dilation balloon having a proximal end and a distal end, the proximal and distal ends of the inflatable dilation balloon being secured to an outer surface of the shaft, the portion of the shaft contained within the dilation balloon including at least one or more ports in communication with the shaft lumen. The balloon dilation catheter includes a curved tip extending distally from the distal end of the dilation balloon.

In still another embodiment, a method of treating an ostium of a paranasal sinus includes placing a balloon dilation catheter in the paranasal sinus, the balloon dilation catheter comprising a shaft, an inflatable dilation balloon disposed on a distal region of the shaft, and a curved tip extending from a distal end of the dilation balloon. The balloon dilation catheter is then advanced into the ostium. The shaft of the balloon dilation catheter is rotated so as to re-orient the curved tip. The balloon dilation catheter is then further advanced in the re-oriented direction. The inflation dilation balloon can then be inflated to dilate the ostium.

In yet another embodiment, an access tool for creating an artificial access passageway to a sinus cavity of the patient includes an elongate tissue penetration member including a shaft and a distal tip, and a recess disposed in the shaft proximal of the distal tip. The tool further includes a tubular sheath removably secured to the shaft in the recess, the tubular sheath including a flange portion.

In still another embodiment, a cannula for positioning one or more devices within a paranasal sinus includes an elongate tubular shaft having a proximal end and a distal end and a first lumen extending therethrough, the elongate tubular shaft further including a second lumen extending along side at least a portion of the first lumen, the distal end of the elongate tubular shaft including at least one curved portion having a curvature between about 5° and 30°.

Further features and advantages will become apparent upon review of the following drawings and description of the preferred embodiments.

BRIEF DESCRIPTION OF THE DRAWINGS

FIG. 4A illustrates a plan view of a balloon dilation catheter according to one embodiment.

FIG. 4B illustrates a cross-sectional view of the balloon dilation catheter taken along the line B-B' of FIG. 4A.

FIG. 4C illustrates a cross-sectional view of the balloon dilation catheter taken along the line C-C' of FIG. 4A.

FIG. 4D illustrates a cross-sectional view of the balloon dilation catheter taken along the line D-D' of FIG. 4A.

FIG. 5 illustrates a cross-sectional and partial side view of a balloon dilation catheter according to another embodiment.

FIGS. 6A-6C illustrate cross-sectional views of a catheter taken along the lines B-B', C-C', and D-D', respectively.

FIG. 7A illustrates a plan view of a balloon dilation catheter according to another embodiment.

FIG. 7B illustrates a cross-sectional view the balloon dilation catheter of FIG. 7A taken along the line B-B'.

FIG. 7C illustrates a cross-sectional view the balloon dilation catheter of FIG. 7A taken along the line C-C'.

FIG. 7D illustrates a plan view of a balloon dilation catheter according to another embodiment.

FIG. 8A illustrates a plan view of a balloon dilation catheter according to another embodiment.

FIG. 8B illustrates a cross-sectional view the balloon dilation catheter of FIG. 8A taken along the line B-B'.

FIG. 8C illustrates a cross-sectional view the balloon dilation catheter of FIG. 8A taken along the line C-C'.

FIG. 8D illustrates a plan view of a balloon dilation catheter according to another embodiment.

FIG. 8E illustrates a cross-sectional view the balloon dilation catheter of FIG. 8D taken along the line E-E'.

FIG. 8F illustrates a cross-sectional view the balloon dilation catheter of FIG. 8D taken along the line F-F'.

FIG. 11A illustrates a plan view of a balloon dilation catheter according to another embodiment. The shaft of the balloon dilation catheter is partially transparent illustrating a braid structure.

FIG. 11D illustrates a plan view of a balloon dilation catheter according to another embodiment. The shaft of the balloon dilation catheter is partially transparent illustrating an internal core wire along with a braid structure.

FIG. 17 illustrates a different embodiment of the balloon dilation catheter.

FIG. 24 illustrates a cross-sectional view of the body structure of the skull defining the sinus cavities of FIG. 23. A balloon dilation catheter is advanced through the cannula. The balloon on the distal portion of the dilation catheter is in a deflated state.

FIG. 27A illustrates an endoscope coupled to the proximal end or hub of a secondary lumen or channel of a cannula.

FIG. 27B illustrates a protective sleeve that can be placed over the main, flexible portion of the endoscope for protective purposes.

FIG. 28A illustrates a cross-sectional view of the nesting tubes of the protective sleeve according to one embodiment. The configuration shown in FIG. 28A illustrates the protective sleeve in a collapsed state.

FIG. 28B illustrates a cross-sectional view of the nesting tubes of the protective sleeve according to one embodiment. The configuration shown in FIG. 28B illustrates the protective sleeve in an extended state.

DETAILED DESCRIPTION OF THE PREFERRED EMBODIMENTS

Figure 1A:
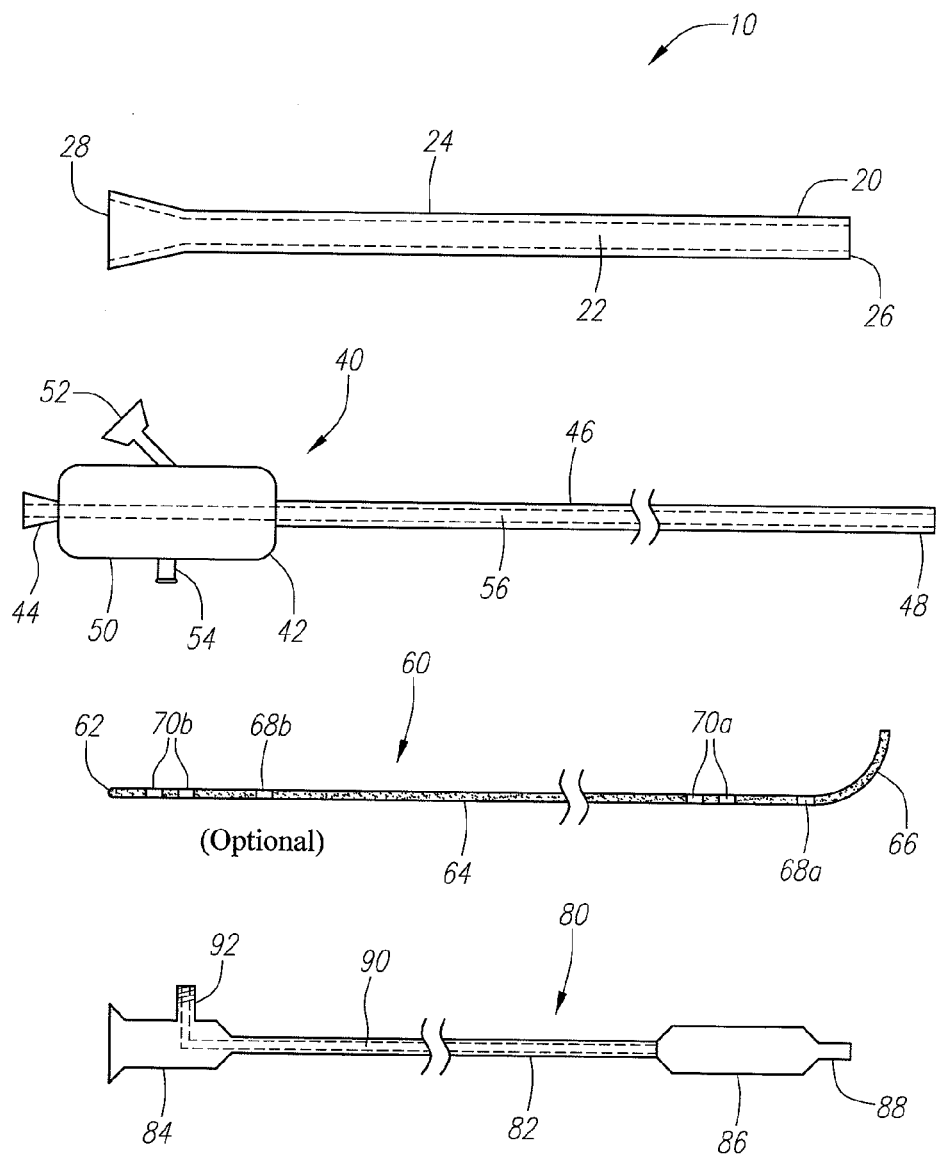
FIG. 1A illustrates various sub-components, some of which are optional, of an apparatus for treating sinusitis. The sub-components include a cannula or guide catheter, a visualization tool such as an endoscope, a guide wire, and a catheter having an expandable member (e.g., balloon) located on a distal end thereof.
Figure 1B:
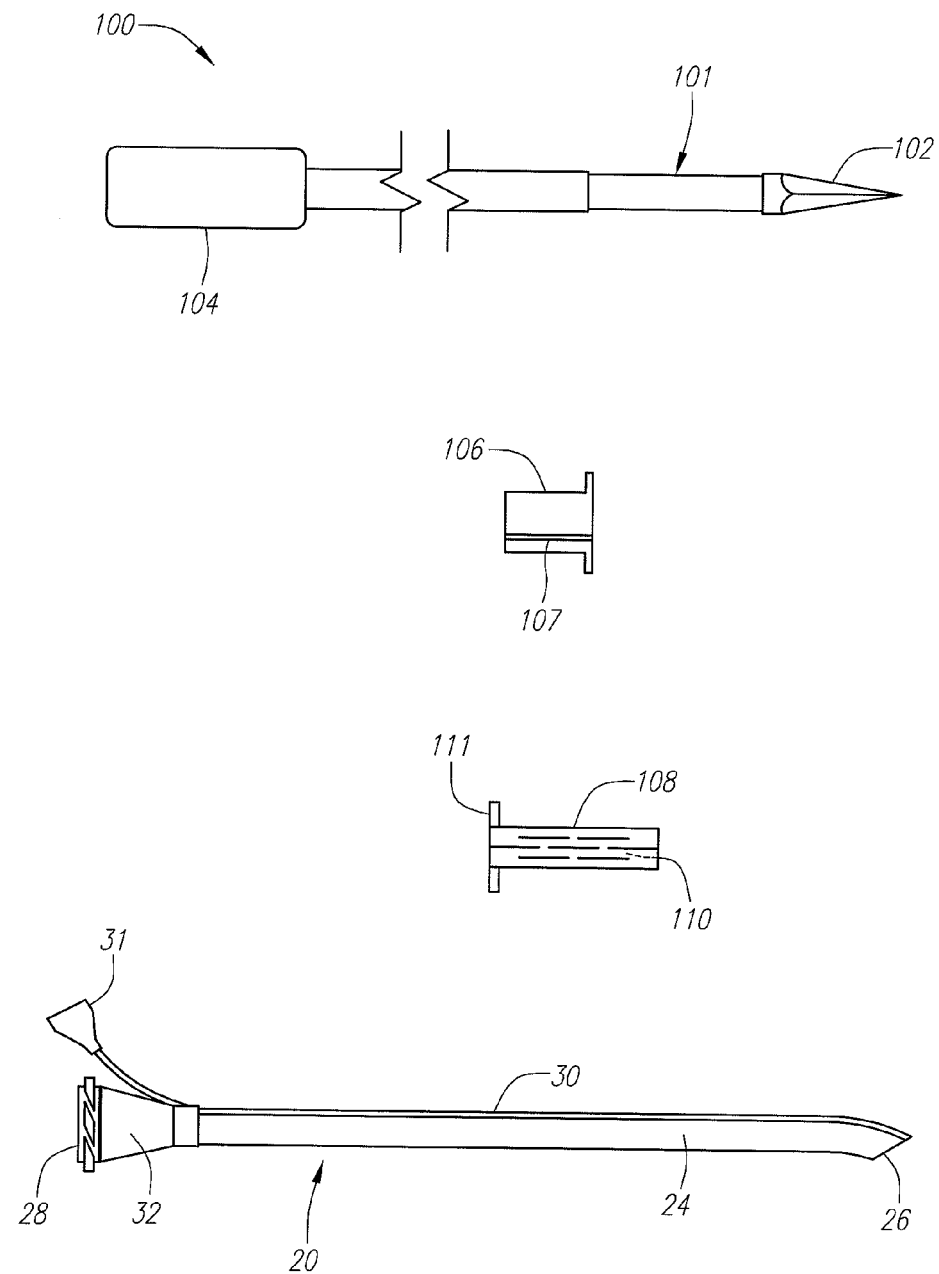
FIG. 1B illustrates a trocar or piercing member along with a stop, sheath, and yet another version of a cannula having a secondary lumen sized for receiving an endoscope.

FIG. 1A illustrates an apparatus 10 for the treatment of sinusitis according to one embodiment. The apparatus 10 may include a number of sub-components as is shown in FIGS. 1A and 1B. In this regard, the apparatus 10 may be sold or offered as a kit or the like that includes all the necessary sub-components necessary to form the complete apparatus or system 10. However, in an alternative aspect of the invention, the apparatus 10 may be sold or offered with fewer than all the sub-components illustrated in FIGS. 1A and 1B. For example, the guide wire or endoscope may, in some instances, be off-the-shelf components existing at the physician's office or hospital that can be utilized with the remaining sub-components of the apparatus 10. In still other instances, the complete apparatus 10 does not need certain sub-components to operate. For example, as explained herein, in certain aspects of the invention, there is not need for a separate guide wire.

As seen in FIG. 1A, the apparatus 10 includes a cannula 20 that is used to provide an access passageway to one or more sinus cavities of the patient. The cannula 20 includes at least one lumen 22 therein. FIG. 1A illustrates a single lumen 22 passing through a central portion of the cannula 20. In other embodiments, as described in more detail herein, there may be multiple, separate lumens or channels 22 contained with the cannula 20. These lumens 22 may located centrally within the cannula 20, incorporated into the wall or exterior of the cannula 20, or even located externally to the main body of the cannula 20.

The cannula 20 is generally made a rigid material such as a rigid polymeric or metallic material such that the cannula 20 maintains its generally elongate shape. However, as explained below, in some alternative embodiments, one or more regions of the cannula 20 may include flexible regions that assist in visualization of the anatomical region of interest in the sinus and/or placement of the expandable member within the anatomical region of interest. Further, the cannula 20 may include an optional Luer fitting or other type of fitting known to those skilled in the art that are associated with one or more lumens 22.

The cannula 20 generally includes an elongate shaft 24 that terminates at a distal end or tip 26 and a proximal end 28. As explained below, the cannula 20 is used with a balloon dilation catheter or other expandable member to aid in the delivery and/or placement of the balloon or expandable member adjacent to or across an anatomical region of interest. For example, the cannula 20 may be dimensioned to permit placement of the balloon dilation catheter in the maxillary sinus ostium and infundibulum via the canine fossa region. As will be explained below, in certain embodiments, the cannula 20 is dimensioned to pass through an artificial passageway or hole created at or in the vicinity of the canine fossa region. The overall length of the cannula 20 depends on the clinical application but for a trans-canine fossa approach that accesses the maxillary sinus ostium, a preferred length is between about 5 cm and about 20 cm. Of course, the length may be shorter or longer than this range depending on, for example, the anatomical nature of the sinus cavity.

As explained above, the cannula 20 may have one or more lumens 22 for passage of various devices. For example, with reference to the lumen 22 of FIG. 1A, the lumen 22 extending along the entire length permits passage of a catheter having an expandable member (e.g., balloon dilation catheter), visualization tool (e.g., endoscope), suction catheter, aspiration catheter, guide wire, and the like. For example, a single lumen 22 cannula 20 like that disclosed in FIG. 1A may be used for delivery of a balloon catheter (described in more detail below) having preferred balloon inflation sizes of between 3 and 7 mm. To accommodate the various devices within the lumen 22, the internal diameter of the cannula lumen 22 may be between about 0.040 inches to about 0.120 inches or even between about 0.060 inches and about 0.090 inches. In general, a smaller diameter cannula 20 will necessitate less tissue trauma at the access site.

Referring back to FIG. 1A, the apparatus 10 includes an imaging tool 40. The imaging tool 40 may include a flexible or semi-flexible endoscope 42 as is shown in FIG. 1A. The endoscope 42 includes a proximal end 44, an elongate shaft portion 46, and a distal tip 48. The proximal end 44 of the endoscope 42 may include a hub 50 or the like that includes an eyepiece 52 that is used visualize the placement and positioning of the apparatus 10 within the patient's sinus cavity and related anatomy. The hub 50 may include a connector 54 that connects to a light source for illuminating the anatomical space. In addition, in certain embodiments, the endoscope 42 may be coupled to a monitor or the like such that the anatomical working space may be visualized better during the procedure. Such attachments and couplings are known to those skilled in the art and are not described herein.

As seen in FIG. 1A, the endoscope 42 may include an optional lumen 56 therein for passage of, for example, a guide wire (described below). In this regard, the endoscope 42 can be used in an "over-the-wire" configuration. In other embodiments, however, there is no need for guide wire lumen. The endoscope 42 is preferably flexible to permit the distal end 48 thereof containing the lens and other optical components to be placed in the desired location within the patient's sinus cavity. The shaft portion 46 is preferably dimensioned so that the same can be slidably disposed within the lumen 22 of the cannula 20. For example, in one aspect of the invention, the endoscope 42 may be placed inside the cannula 20 during placement of a guide wire. The endoscope 42 may then be withdrawn from the cannula 20 and a balloon dilation catheter (described below) can be fed over the guide wire. The exterior of the shaft 46 may be coated with or otherwise contain a lubricous coating to aid in slidability within the cannula 20.

Referring still to FIG. 1A, in certain embodiments the apparatus 10 includes a guide wire 60. In still other embodiments, however, the guide wire 60 may be eliminated entirely. In those embodiments using a guide wire 60, it includes proximal end 62, a central portion 64, and a distal end 66. The guide wire 60 may have a conventional construction for guide wires used in other applications. For example, the guide wire 60 may include a tapered core wire and outer jacket, coating, or coil extending along some or all of the length of the core wire. The guide wire 60 is semi-flexible, preferably with increasing flexibility towards the distal end, to permit passage through the cannula 20, which in certain configurations, may include one or more bent or curved sections. The guide wire 60 also has sufficient columnar strength to prevent buckling when the guide wire 60 is positioned through or across an anatomical space that is to be dilated (e.g., ostium). The guide wire 60 may be coated with or otherwise contain a lubricous coating to aid in pushability through the various lumens (e.g., lumen 22) through which it can be passed. As seen in FIG. 1A, the distal end 66 of the guide wire 60 may be pre-formed or pre-shaped with a j-shaped bend. The distal end 66 (with the optional j-shaped bend) may be manipulated by moving the proximal end 62. For example, the distal end 66 may be moved axially by pushing or pulling the guide wire 60. Similarly, the distal end 66 may be rotated or steered about an axis by rotation of the guide wire's proximal end 62. Such "steerability" facilitates passage of the guide wire 60 through the anatomical structures of the sinus and nasal cavities.

The guide wire 60 may include one or more visible markers 68a, 68b, 70a, 70b that are used to aid the user in placing the guide wire 60 in the proper location. For example, as seen in FIG. 1A, a distal marker 68a is placed that may be visually identified by, for instance, its color. A corresponding marker 68*b* is located proximally on the guide wire 60 and may be colored with the same color. FIG. 1A further shows an additional set of distally placed markers 70*a*. These markers are distinguished from the marker 68*a* because there are two (2) markers or bands. The proximal portion of the guide wire 60 includes corresponding markers 70*b* which also comprises two (2) marker bands. As an alternative, the two (2) markers 70*a*, 70*b* could be replaced by a single maker that is a different color than markers 68*a*, 68*b*. The makers on the distal 68*a*, 70*a* and proximal ends 68*b*, 70*b* are separated by the same distance such that the physician can correlate axial movement of the distal end 66 of the guide wire 60 with movement of the proximal end 62.

Still referring to FIG. 1A, the apparatus 10 includes a balloon dilation catheter 80. The balloon dilation catheter 80 includes an elongate tubular section 82 (sometimes referred to as a shaft) that has a proximal hub 84 and a distally-located expandable member 86 which may take the form of a balloon. The balloon dilation catheter 80 may also include an optional distal tip 88 which, as explained in more detail below, may take the form of a number of configurations and shapes. The balloon dilation catheter 80 includes a central lumen 90 or passageway that communicates with the expandable member 86 and the proximal hub 84. In this regard, there is a fluidic passageway through which a fluid can pass to selectively expand and contract the expandable member 86. The proximal hub 84 may include a connector 92 such as a Luer fitting or the like which can be coupled to a device for delivering/extracting the fluid to expand/contract the expandable member 86. For example, a syringe, or inflation apparatus known to those skilled in the art (now shown), or the like may be fluidically coupled to the connector 92 that can be used by the operator to expand/deflate the expandable member 86 as needed. In addition, in still other embodiments (not shown in FIG. 1A), the balloon dilation catheter 80 may contain additional lumens for the passage of various devices. For example, added lumens may be dimensioned to provide access for a guide wire 60 or an imaging tool 40 like an endoscope 42.

Referring now to FIG. 1B, in some embodiments the apparatus 10 may include additional components as part of kit to provide access to the patient's sinus cavity of interest. For example, a piercing tool 100 in the form of a trocar, drill, or the like may be provided. The piercing tool 100 includes a sharpened distal tip 102 and a proximal hub 104 or handle that can be grasped by the physician. The piercing tool 100 is used to create an artificial opening in, for example, the canine fossa region to provide an access passageway to the sinus cavity of interest. The piercing tool 100 may include an optional recessed portion 101 that is used to hold a sheath 108 (described in more detail below) during placement. An optional stop 106 may also be included that is used in conjunction with the piercing tool 100 to limit the depth of penetration of the piercing tool 100. In this regard, the stop 106 acts as a safety device that limits axial movement of the piercing tool 100 during the process of forming the access passageway. The stop 106 may include a slit 107 or the like along its length so that the same can be easily placed over the piercing tool 100 during placement.

FIG. 1B also illustrates a sheath 108 that may be positioned within the passageway created by the piercing tool 100. The sheath 108 includes an elongate body portion having a lumen 110 passing there through. The proximal end of the sheath 108 may include a rim or flange 111 that is used to secure the sheath 108 in the newly created artificial opening. FIG. 1B illustrates an alternative embodiment of the cannula 20 illustrated in FIG. 1A. The cannula 20 of FIG. 1B includes a secondary lumen 30, which in this illustrated embodiment, is positioned external to the main cannula shaft 24. The secondary lumen 30 runs substantially the entire length of the cannula 20 and terminates at a proximal hub 31 and can be used to guide an imaging tool 40 such as an endoscope 42. The proximal hub 31 may be made of any number of fittings, connectors, or interfaces that can be used to couple to an imaging tool 40 like an endoscope 42. The cannula 20 illustrated in FIG. 1B may be used, for example, in those embodiments where the guide wire is eliminated.

Figure 2A:
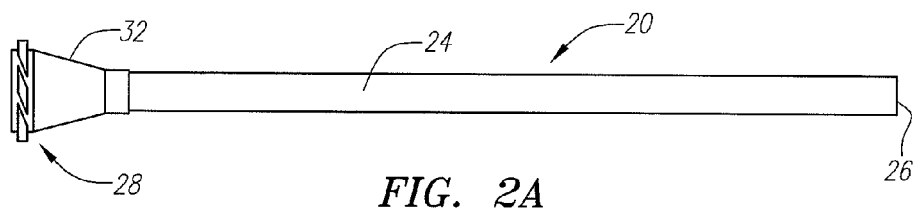
FIGS. 2A-2G illustrate side views of various embodiments of a cannula or guide catheter.
Figure 2B:
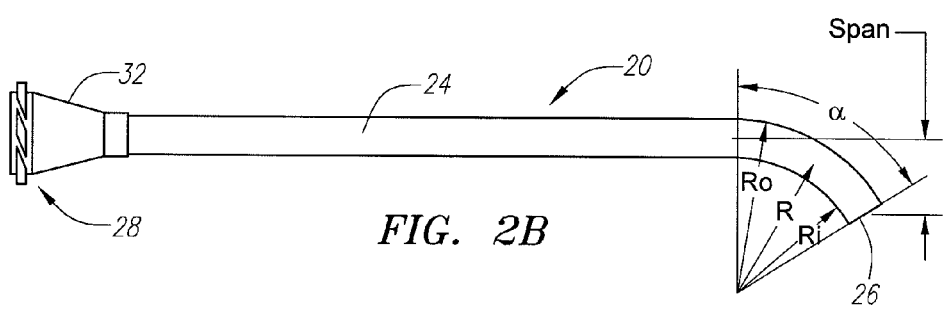
Figure 2C:
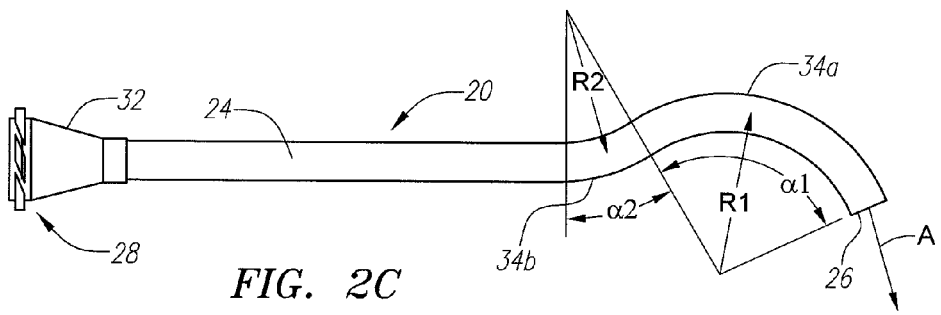
Figure 2D:
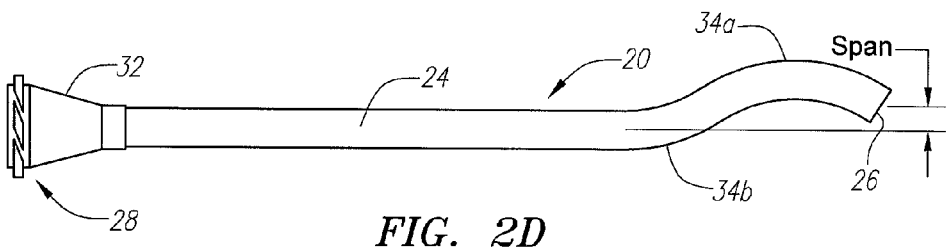
Figure 2E:
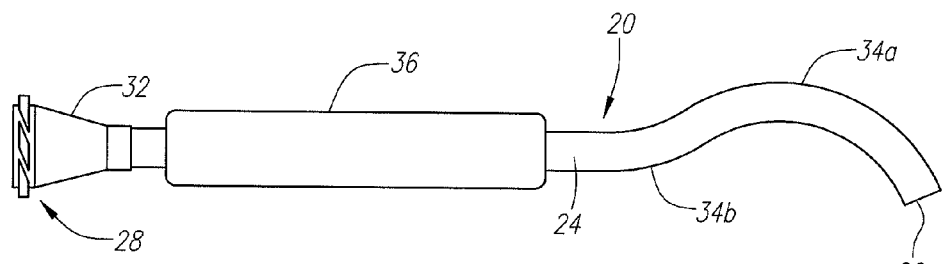
Figure 2F:
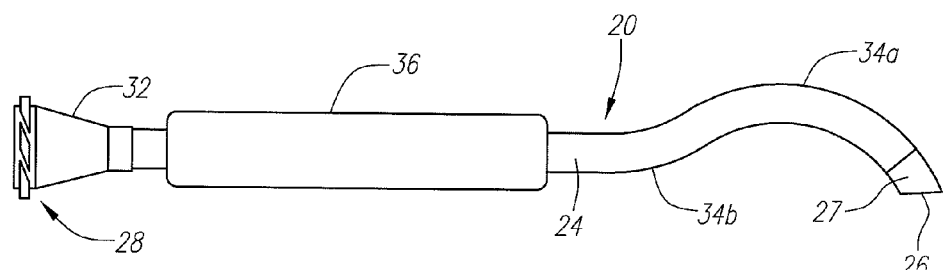
Figure 2G:
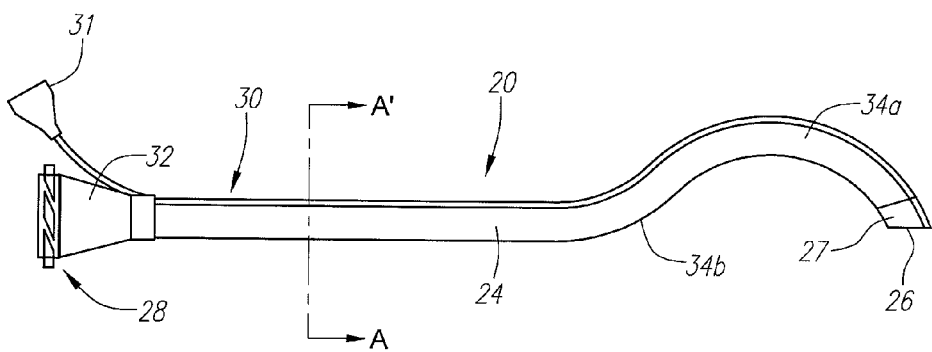
Figure 2H:
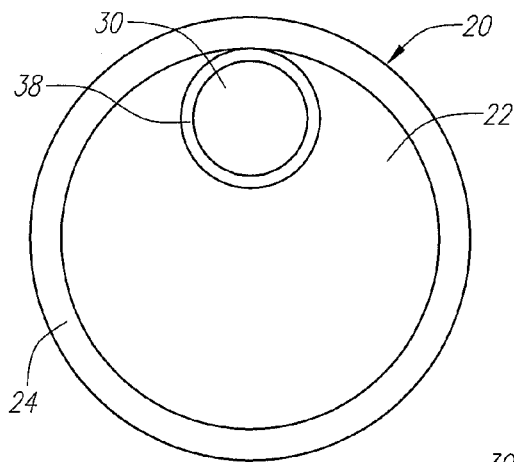
FIGS. 2H-2O illustrate cross-sectional views of the shaft of a cannula according to various embodiments.
Figure 2I:
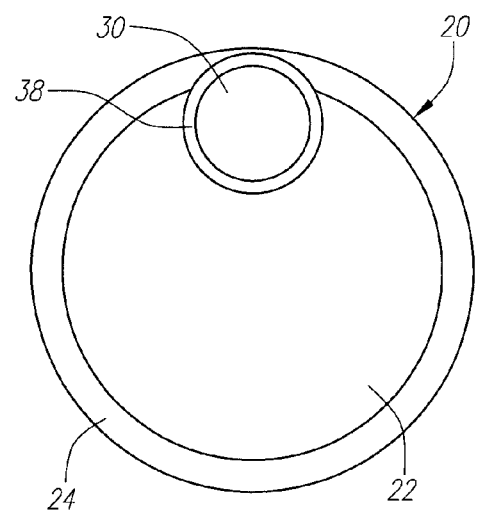
Figure 2J:
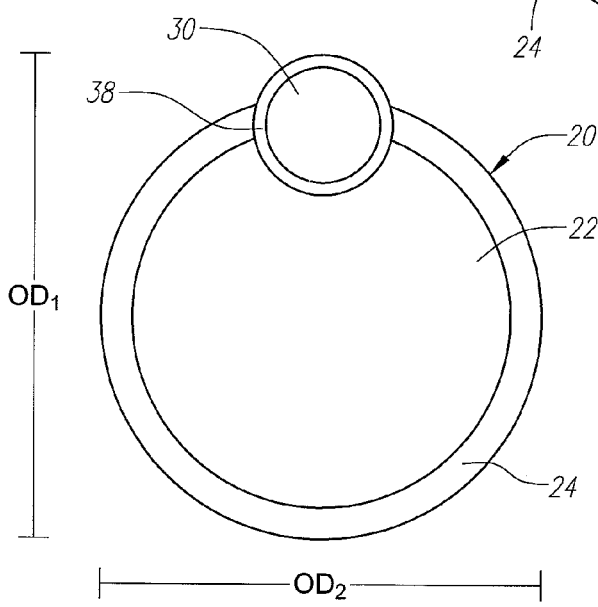
Figure 2K:
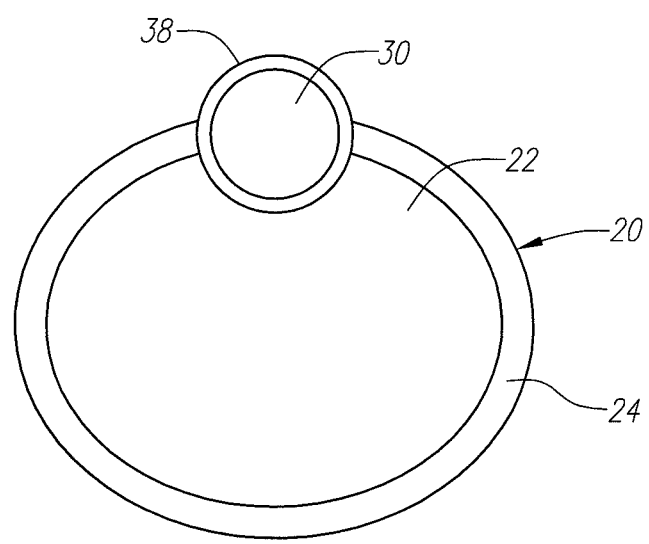
Figure 2L:
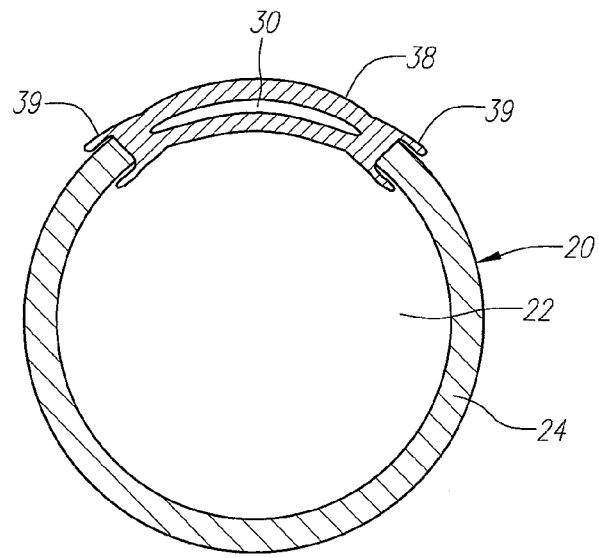
Figure 2M:
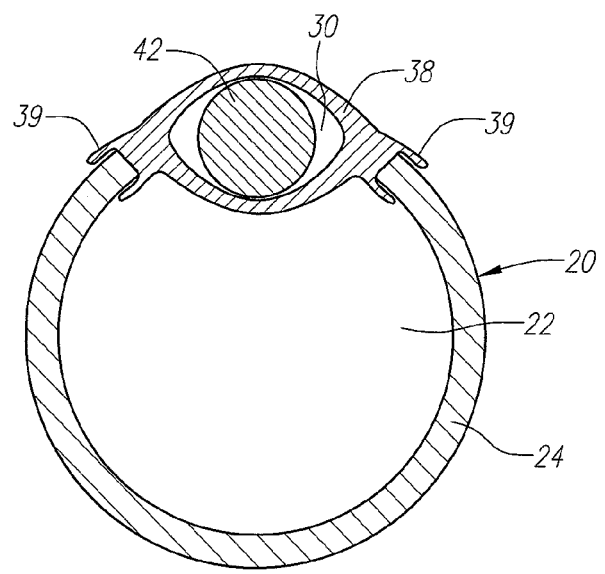
Figure 2N:
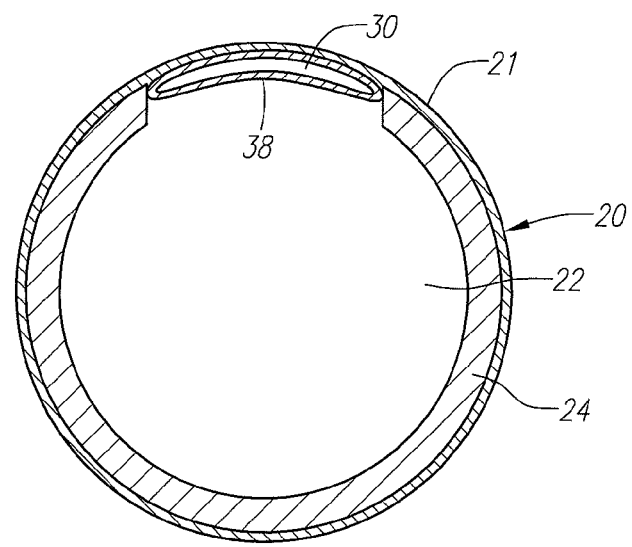
Figure 2O:
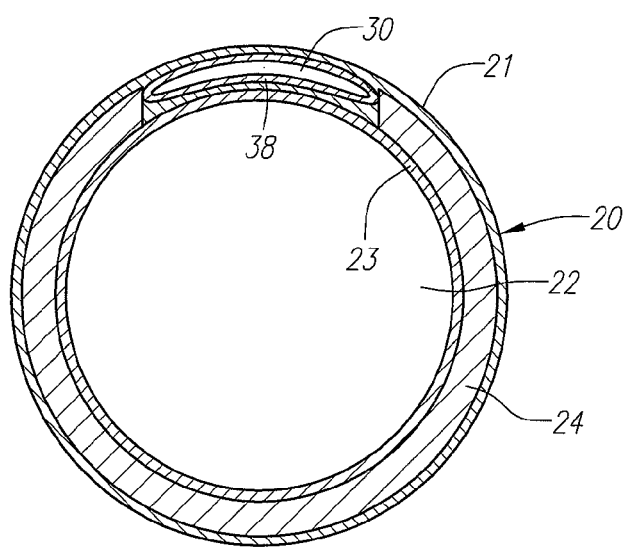
Figure 2P:
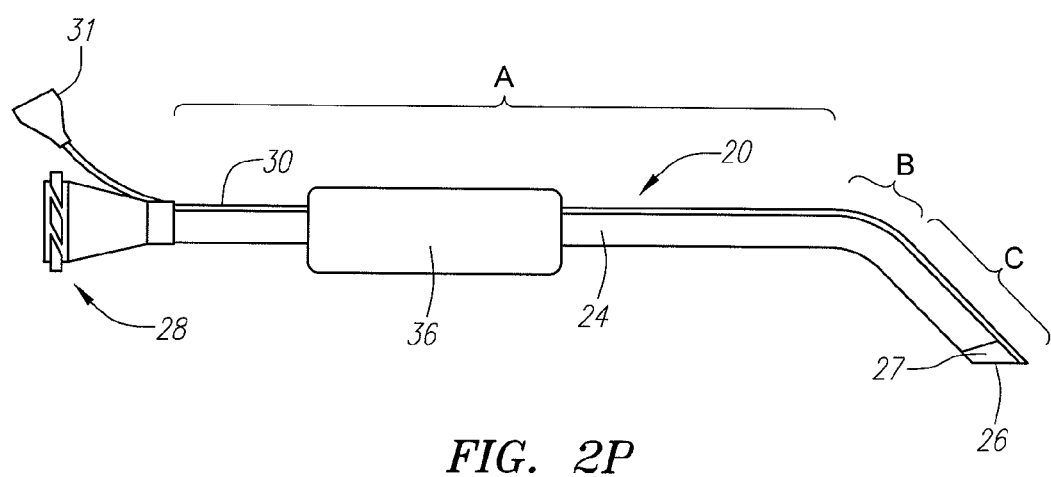
FIG. 2P illustrates a side view of a cannula according to another embodiment. The cannula includes a handle, a secondary lumen, and a bent or curved tip.
Figure 2Q:
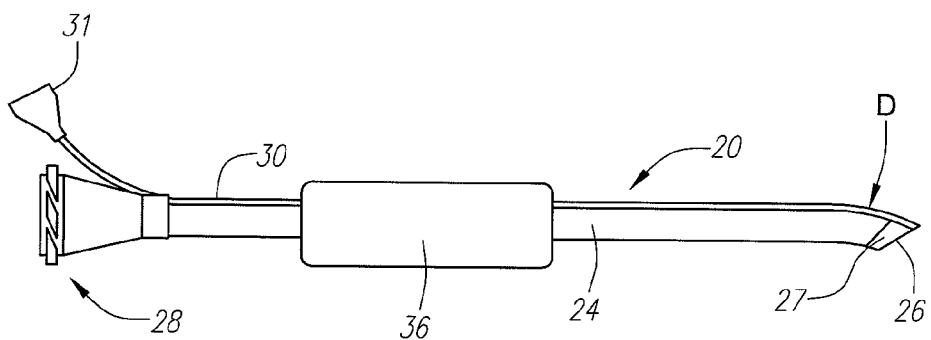
FIG. 2Q illustrates a side view of another embodiment of a cannula.
Figure 2R:
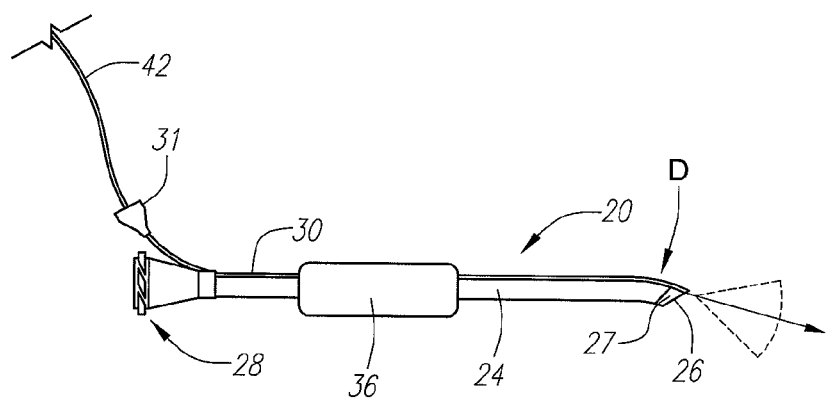
FIG. 2R illustrates a side view of cannula of the type shown in FIG. 2Q with an endoscope slidably disposed inside the secondary lumen. The field of view of the endoscope is shown at the distal end of the secondary lumen.
Figure 2S:
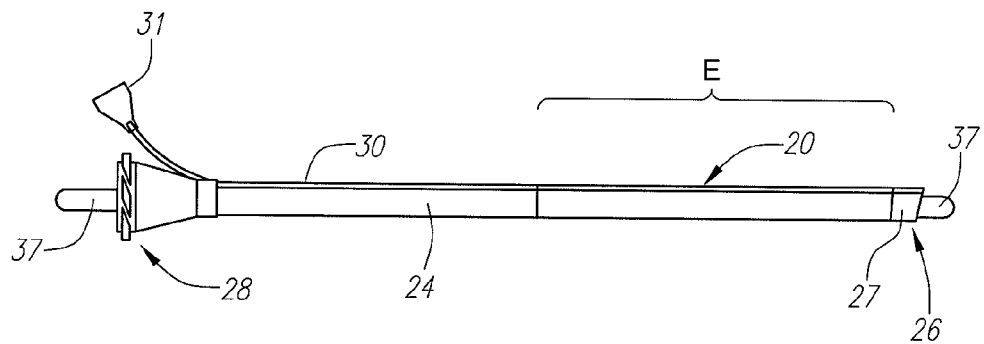
FIG. 2S illustrates still another embodiment of a cannula. The cannula is shown in a straight configuration after a rigid obturator is passed through a central lumen or passage.
Figure 2T:
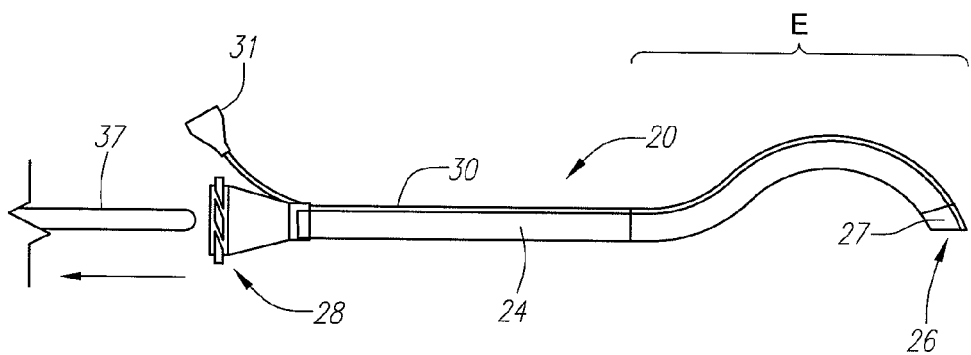
FIG. 2T illustrates the cannula of FIG. 2S with the obturator removed.

FIGS. 2A-2T illustrate various embodiments of the cannula 20 that may be used in connection with the apparatus 10. The various features shown may be used individually or in combination. FIG. 2A illustrates a cannula 20 having a substantially straight shaft 24 and an optional Luer fitting on a proximal hub 32 located at the proximal end 28 of the cannula 20. As shown in FIG. 2A, the shaft 24 is made from a rigid material such as, for instance, stainless steel tube. FIG. 2B illustrates a cannula having a single curved portion at the distal tip 26. The curve or arc created at the distal tip 26 subtends an angle α. The sharpness of the curve is defined by either the inner radius $R_i$, the outer radius $R_o$, or the midline radius R. The span illustrated in FIG. 2B is the lateral offset of the tip 26 from the centerline of the cannula 20 along the shaft 24 (proximal to tip 26) and is a function of the angle α and the radius of curvature R. In one preferred embodiment, the cannula has an angle α from about 1° to about 90° with a radius of curvature R of about 5 mm to about 30 mm. The curved tip 26 may be directed or "pointed" in any direction within the sinus cavity by rotation of the proximal end 28 of the cannula 20. The shaft 24 may be formed from a rigid material such as, for instance, stainless steel tubing.

FIGS. 2C and 2D illustrate a cannula 20 with two curves 34*a*, 34*b* in the shape of a "question mark." In this embodiment, the distal curve 34*a* subtends an angle α1 and has a radius of curvature R1. The second or more proximal curve 34*b* subtends an angle α2 and has a radius of curvature R2. Having two curves 34*a*, 34*b* as such allows for additional degrees of freedom to alter the tangent direction (as shown in the arrow A of FIG. 2C) of the distal end 26 of the cannula 20 and the span. It should be understood that the multiple curves may have a sinusoidal shape such as an "S" shape. In FIG. 2D, the span can even be a negative number. Preferred embodiments making use of multiple (e.g., two) curves result in a tangent direction of preferably about 5° to about 90° (relative to the main shaft axis) and a span of about −0.5 cm to about +1.0 cm. Such a curve shape can be especially useful in certain anatomical configurations of a patient's nasal and paranasal spaces, for example if the patient has a pronounced "barrel" shape of their nasal walls.

FIG. 2E illustrates an embodiment of a cannula 20 with an optional handle 36. It should be understood that the handle 36 is contemplated as an option on all embodiments of the cannula 20. The handle 36 is preferably of a larger diameter than the diameter of the shaft 24, such as 1 mm to 10 mm or larger. The handle 36 also may have a circular or non-circular cross section for some or all of its length. Additional features such as finger grips, bumps, texturing, or ridges are also contemplated to improve the ergonomic feel of the handle 36. When used in the canine fossa application, it is preferable to position the handle 36 proximally on the shaft 24 so as not to interfere with either the access hole of the canine fossa, or other structures such as the teeth. The distance from the tip 26 of the cannula 20 to the handle 36 is about 3 cm to about 10 cm, and most preferably about 5 cm to about 7 cm.

FIG. 2F shows an embodiment of a cannula 20 that includes a soft distal tip 27. Whereas the shaft 24 of the cannula 20 is preferably relatively rigid, e.g. formed from stainless steel, the soft distal tip 27 in this embodiment is preferably made of a more flexible polymer, such as Pebax, Nylon, Pellethane, PTFE, polyethylene, or a combination thereof. The soft tip 27 makes the distal end 26 of the cannula 20 more atraumatic to tissue. Furthermore, the soft tip 27 facilitates the removal of the balloon dilation catheter 80, after the balloon 86 has been inflated and subsequently deflated. The deflated balloon 86 often forms "wings" which can be difficult to withdraw back inside the catheter lumen 22, particularly if the lumen 22 is defined by a rigid material such as stainless steel. A soft tip 27 can partially or temporarily deform and diametrically expand to help ease during retraction of the deflated balloon 86. Enhancements to the lubricity and/or radiopacity can also be incorporated or added, such as oxidized polyethylene, paralene, PTFE, hydrophilic coatings, barium sulfate, bismuth subcarbonate, or bismuth trioxide. The soft tip 27 may be attached to the distal end of the shaft 24 by suitable means such as thermal or adhesive bonding. Additionally, the distal end 26 of the cannula 20 can have an angled or canted end as shown. The canted end further enhances the ability to withdraw a deflated balloon 86 back into the distal end 26 of the cannula 20.

FIG. 2G illustrates another embodiment of a cannula 20 that includes an additional or secondary lumen 30. The secondary lumen 30 may be used to position an imaging tool 40 such as a flexible endoscope 42 within it, and extend to the distal tip 26 of the cannula 20. The cannula 20 may include one or more optional curved portions 34a, 34b as described herein. Alternatively, the cannula 20 may be substantially straight as is shown, for instance in FIG. 1B. As shown in FIG. 2G, the cannula 20 includes a soft distal tip 27.

FIGS. 2H through 2O further illustrate various configurations for the secondary lumen 30, which will be described in further detail below. The secondary lumen 30 may take the form of a lumen or channel through which an imaging tool 40 passes. In the cannula embodiments incorporating a lumen for the imaging tool 40, these are preferably utilized in the placement of balloon dilation catheters 80 that do not have a lumen that can pass an imaging tool 40. Generally, the secondary lumen 30 is sized to contain a relatively small flexible endoscope 42. For example, in one embodiment, the secondary lumen 30 is sized to slidably receive a 0.5 mm flexible endoscope (falloposcope model 11565) made by Karl Storz Endoscopy—America Inc. (Culver City, Calif.). This endoscope 42 has a flexible main portion that has an outer diameter of about 0.5 mm and is about 100 cm in length.

FIGS. 2H-2O illustrates various cross-sectional views of a cannula 20 with a secondary lumen 30 for positioning an imaging tool 40 such as an endoscope 42. The cross-sectional views are taken along the line A-A' of FIG. 2G. As seen in FIG. 2H, the secondary lumen 30 (e.g., lumen or channel for endoscope 42) is defined by a tube 38 that is positioned inside the main body of the cannula 20. The tube 38 is preferably bonded to the inside surface of the main shaft 24 of the cannula 20 by suitable means such as thermal or adhesive bonding. The tube 38 is preferably formed of a polymer or a metallic tube, and as mentioned prior, the main tube is preferably relatively rigid, e.g. stainless steel. The inside of the tube 38 may be coated with a lubricious coating or the like to ease slidability of the endoscope 42 through the secondary lumen 30.

FIG. 2I illustrates an alternative arrangement whereby a portion of the wall of the main shaft or tube 24 of the cannula 20 is removed, and the tube 38 used to form the secondary lumen 30 is "nested" into the wall of the main tube 24. This provides for the ability to maintain a larger lumen 22 through the main body of the cannula 20. An even larger lumen 22 through the cannula 20 can be provided, as shown in the embodiment of FIG. 2J. In this embodiment, the entire wall thickness of a portion of the main tube of the cannula 20 is removed, and the tube 38 is positioned within the slot created therein. As seen in FIG. 2J, the outer diameter $OD_1$ is greater than the outer diameter $OD_2$. Preferably the slot that is created to make room for the tube 38 extends from the distal tip 26 proximally for at least a portion of the length of the cannula 20 that is at least as long as the desired length to be positioned into and beyond the canine fossa. Proximal of that point, it may be desirable to position the tube 38 on the outer surface of the cannula. The tube 38 thus forming the secondary lumen 30 transitions from being at least partially within the main lumen 22 to being completely external to the main lumen 22 at a proximally located transition point.

FIG. 2K illustrates a similar embodiment to that shown in FIG. 2J except that the main tube or shaft 24 of the cannula 20 is formed in a generally oval or elliptical cross-sectional shape such that the two diameters are closer in value. This embodiment provides for a relatively large cross-sectional area of the lumen 22 of the main shaft 24 of the cannula 20, while keeping the two diameters equal or relatively similar.

FIGS. 2L and 2M illustrate additional embodiments where the tube 38 used for the secondary lumen 30 is capable of transitioning between a collapsed configuration (FIG. 2L) and an expanded configuration (FIG. 2M). For example, in the absence of an imaging tool 40 within the lumen 30 of the tube 38, the tube 38 is in the collapsed configuration, which helps minimize the outer diameter of the cannula 20 while also helping to maximize the inner diameter of the main lumen 22. In this embodiment, the tube 38 is positioned and secured within a slot in the wall of the main shaft 24. Optional flanges 39 on each side of the tube 38, as shown in FIGS. 2L and 2M, may assist in securing the tube 38 to the main shaft 24. The tube 38 for the secondary lumen 30 is preferably formed of a relatively flexible and resilient material such as Pebax, Nylon, or PTFE, or a combination thereof. When an endoscope 42 is passed into the tube 38, the tube 38 expands (FIG. 2M). If the endoscope 42 is withdrawn, the tube 38 preferably re-collapses entirely or, alternatively, at least partially. When a device such as a balloon dilation catheter 80 is advanced or withdrawn through the main lumen 22, the flexible nature of the tube 38 allows itself to "make room" for the device, particularly given the relatively larger profile of the balloon portion 86 of the balloon dilation catheter 80, and especially after it has been inflated and is desired to be withdrawn back into the cannula 20. The extra room for the balloon dilation catheter 80 is present both when the endoscope 42 is disposed in the secondary lumen 30 and also when it is withdrawn from the secondary lumen 30. However there will naturally be more room for devices such as a balloon dilation catheter 80 in the main lumen 22 if the endoscope 42 is not present in the secondary lumen 30.

FIG. 2N illustrates yet another alternative embodiment of a cannula 20 with a collapsible tube 38 forming a secondary lumen 30. In this embodiment, the tube 38 is a relatively thin walled tube, preferably formed of PTFE or FEP. Flexible tubes of this material can be formed very thin, with a preferred wall thickness of from around 0.0005 inches to around 0.0025 inches (more preferably about 0.0015 inch). The tube 38 is positioned in a formed slot in the wall of the main shaft 24, and may be secured by heat or adhesive bonding to a thin tube or jacket 21 of polymer that preferably extends around the entire circumference of the main shaft 24. This outer tube or jacket 21 is preferably formed of a heat-shrinkable or heat-formable tube such as Pebax or Nylon. Chemical etching of the outer surface of the tube 38 forming the secondary lumen 30 can further facilitate attachment to the outer tube 21.

A further refinement of this embodiment is shown in FIG. 2O. Here, an additional thin walled inner tube 23, preferably of PTFE or other highly lubricious polymer, is positioned inside the main shaft or tube 24 to serve as an inner liner. This inner tube 23 preferably extends through the entire length of the main shaft 24. In this embodiment, if a soft tip 27 is provided, the inner tube 23 can serve as a substrate upon which to secure the soft tip 27. Consequently, in a preferred embodiment, the thin inner tube 23 extends distally beyond the distal end of the main shaft 24, and a soft tip 27 is secured to the outside of the thin inner tube 23, and completely embeds the tube 38 forming the secondary lumen 30. The distal extension is preferably about 0.5 mm to about 3 mm and more preferably about 1 mm beyond the distal end of the main shaft or tube 24.

FIG. 2P illustrates still another embodiment of a cannula 20. In this embodiment, the cannula 20 has a proximal straight portion A, a curved or elbow portion B, and a relatively straight distal portion C. With this embodiment, when used through the canine fossa, the elbow B is preferably positioned right at the hole created through the bony portion. The straight distal segment C then extends within the sinus towards the ostium, while the proximal portion A extends out from the canine fossa opening in a direction further away from the teeth. This embodiment may be more suitable in patients where the maxillary sinus ostium is disposed more anterior vs. posterior in the sinus cavity.

FIG. 2Q illustrates an embodiment of a cannula 20 with a relatively short curved portion D located on the distal end 26 of the cannula 20 and also incorporated into the tube 38 forming the secondary lumen 30. Preferably the secondary lumen 30 is sized close to the diameter of the endoscope 42 (not shown in FIG. 2Q). When the endoscope 42 is positioned at the end of the secondary lumen 30, the direction of view is influenced by the degree of curve in the cannula 20. The main lumen 22 (through which a balloon dilation catheter 80 would be placed) is preferably relatively larger than the shaft size of the balloon dilation catheter 80. Therefore, the trajectory or direction that the balloon dilation catheter 80 takes is less impacted by the curve in the cannula 20. In this fashion, the cannula 20 behaves more like a straight cannula vis-à-vis balloon catheter 88 delivery but performs like a curved cannula 20 with respect to viewing through the endoscope 42. By altering the viewing direction, the endoscope 42 behaves more like a conventional angled endoscope, which can be useful for being able to view more of the sinus cavity if the cannula 20 and endoscope 42 are rotated. FIG. 2R illustrates a cannula 20 with a flexible endoscope 42 positioned in the secondary lumen 30 and emerging at the distal tip 26 of the cannula 20. The solid arrow represents the centerline of the field of view of the endoscope 42 while the dashed cone represents the field of view of the endoscope 42.

FIGS. 2S and 2T illustrate still another embodiment of a cannula 20. In this embodiment, the cannula 20 includes a biased portion E that is pre-formed and, in its natural state, forms a curved or sinusoidal shape (e.g., FIG. 2T). The biased portion E is formed from a relatively flexible material (e.g., polymeric) such that placement of a relatively rigid obturator 37 or other device within a lumen (not shown) of the biased portion E, it causes the curved, biased portion E to straighten out (e.g., FIG. 2S) prior to placement. After positioning the "straight" cannula 20 into the desired location (e.g. in the sinus cavity), the biased portion E re-curves upon retraction of the obturator 37 from the lumen 22 of the cannula 20. Preferably, the biased portion E is stiff enough such that other devices placed within it, such as a balloon dilation catheter 80 or flexible endoscope 42, do not cause the biased portion E to straighten out (i.e., the state of FIG. 2S). This embodiment of the cannula 20 is particularly useful if there are anatomic features that can not be easily negotiated upon advancement of a curved cannula, but can be negotiated if the cannula 20 is initially in a straight configuration.

It should be understood that any combination of the features described in connection with the cannulas 20 described herein may be contemplated. For example, any of the various curve, sinusoidal shapes, soft tips, canted ends, secondary tube lumens, Luer fittings, handles, linings, materials, etc. described herein may be substituted or mixed and matched as appropriate into the final structure of the cannula 20.

The endoscope 42 or other imaging tool 40 contemplated herein typically have optical components such as lenses or the like that are located on the distal end thereof. Because of this, when using an endoscope 42 with a cannula 20 in a sinus cavity such as the maxillary sinus or anywhere else in the nasal or paranasal space, there is a risk of getting the distal end (and thus optics) of the endoscope dirty. For example, if the endoscope 42 inadvertently touches the mucosa or other tissue it can get smudged with fluid such as mucous or blood. This can impede or prevent visualization of the anatomical space. If this happens, the entire cannula 20 may need to be removed from the patient and the distal end of the endoscope 42 can be wiped clean. Alternatively, the endoscope 42 can be removed from the cannula 20, wiped clean, and repositioned in the cannula 20.

Figure 3A:
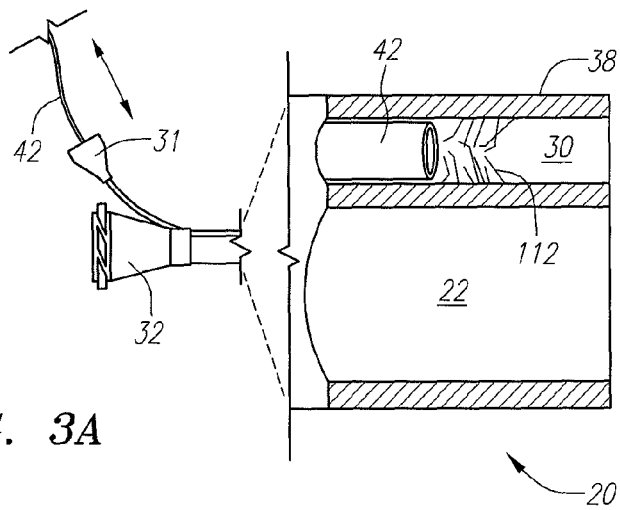
FIG. 3A illustrates a magnified, partial cross-sectional view of a cannula according to one embodiment. A cleaning structure is present in the secondary lumen.
Figure 3B:
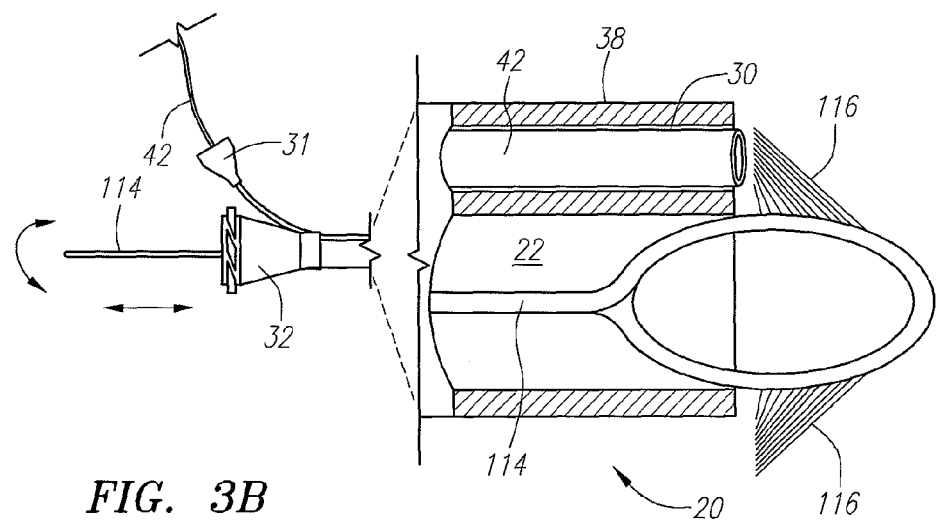
FIG. 3B illustrates another magnified, partial cross-sectional view of a cannula according to one embodiment. A cleaning tool is shown disposed in the main lumen or channel of the cannula.

FIGS. 3A and 3B illustrate two alternative cleaning structures that can be used to avoid having to retract and manually clean the distal end of the endoscope 42. FIG. 3A illustrates a partial, magnified cross-sectional view of the cannula 20 showing the main lumen 22 along with the secondary lumen 30 containing an endoscope. A cleaning structure 112 is provided in the secondary lumen 30 near the distal end. The cleaning structure 112 serves to wipe the face of the endoscope 42 clean each time it is passed through it. The cleaning structure 112 can be one or more "squeegee" portions such as bristles (as shown), absorbent material, or the like. Multiple bristles are preferred, as they can be directed in a retrograde fashion to brush across the front surface of the endoscope 42, assuring that any material on the optics of the endoscope 42 gets pushed aside or otherwise removed.

Alternatively, as shown in FIG. 3B, a cleaning tool 114 can be positioned in the main lumen 22 of the cannula 20. The cleaning tool 114 has one or more cleaning members 116, such as a "squeegee", absorbent material, or bristles located on a portion thereof. The cleaning tool 114 shown in FIG. 3B has multiple sets of deformable bristles 116 attached that can be swept across the face of the scope by rotation of the cleaning tool 114. The bristles 116 preferably have a retrograde orientation from the points of attachment. Also, the bristles 116 preferably expand out to an overall diameter greater than the main lumen 22, such that the bristles 116 can extend across the full diametric face of the endoscope 42.

The cleaning structure 112 and cleaning tool 114 illustrated in FIGS. 3A and 3B may be omitted if a sheath 108 is used to maintain or support the artificially created hole or passageway created in the patient's tissue/boney structure. The sheath 108 generally creates a clean, unobstructed passageway through which the various devices (including endoscope 42) may pass.

With reference now to FIGS. 4A through 4D, FIGS. 5, 6A-6C, 7A-7D, 8A-8F, 9A-9B, 10A-10F, 11A-11F, and 12A-12F, various embodiments of a balloon dilation catheter 80 are illustrated. As explained with respect to FIG. 1A, in certain embodiments the balloon dilation catheter 80 may have a distal tip 88 that projects some distance from the balloon 86. FIG. 4A illustrates one embodiment of a balloon catheter 88. In this embodiment, the balloon catheter 88 incorporates a soft distal tip 88 extending distally of the balloon 86. The elongate tubular member or catheter shaft 82 as well as the tip 88 includes a lumen 96 (best seen in FIGS. 4B, 4C, 4C) through which a flexible endoscope 42 can be positioned. In use, the distal end of the endoscope 42 is positioned at or near the distal end of the balloon catheter tip 88, which allows for viewing from the balloon catheter tip 88. FIG. 4A illustrates a cone (dashed lines) illustrating the field of view from an endoscope 42 distally advanced through the balloon catheter 88. The balloon catheter 88 also includes an inflation lumen 90 for inflating and deflating the expandable member 86 (e.g., balloon). FIG. 4B illustrates a cross-sectional view taken along the line B-B' of FIG. 4A showing the endoscope 42 positioned with the lumen 96 in the elongate shaft 82 of the balloon dilation catheter 80. FIG. 4B also shows the inflation lumen 90 that is used to carry the inflation medium (e.g., saline fluid or the like). FIG. 4C illustrates a cross-sectional view taken along the line of C-C' of FIG. 4A. The balloon 86 in an expanded state is shown about the periphery of the elongate shaft 82 contained within the balloon 86 (obscured from view in FIG. 4A). FIG. 4D illustrates a cross-sectional view taken along the distal tip 88 of the balloon dilation catheter 80 along the line D-D' of FIG. 4A. As best seen in FIGS. 4A and 4D, the distal tip 88 includes a lumen 96 for the passage of the endoscope 42. The distal tip 88 may be substantially straight as is shown in phantom in FIG. 4A or, alternatively, the distal tip 88 may be curved as shown in FIG. 4A. The curvature of the distal tip 88 may be formed using a biasing member 98 that may be positioned within the distal tip 88. The biasing member 98 may be formed as a wire or the like. The curved distal tip 88 allows for the catheter tip to naturally be directed away from the ethmoid bulla to aid in positioning of the distal portion of the balloon catheter within the nasal cavity. The biasing member 98 may be bent or preformed prior to placement by the physician. In addition, as shown in FIG. 4A, the distal end of the distal tip 88 may include a bulbous end 88a as shown in phantom in FIG. 4A.

Placement of the endoscope 42 within the balloon dilation catheter 80 enables the balloon dilation catheter 80 to be positioned across the ostium and into the anatomy of the nasal cavity under direct visualization. The distal tip 88 of the balloon dilation catheter 80 is essentially "flown" through the anatomy in this embodiment, while the endoscopic image is being viewed by the operator. The distal tip 88 preferably transitions from a soft distal end and gets progressively stiffer towards the balloon 86, enabling the relatively stiffer balloon 86 to be advanced and tracked through the anatomy of the nasal cavity beyond the ostium in an atraumatic manner.

In one embodiment, as shown in FIG. 5, the shaft of the balloon dilation catheter 80 further incorporates a torsionally rigid structure such as braid 81 embedded into a polymeric tubular shaft 82. Such a structure allows the distal tip 88 of the catheter 80 to be rotationally directed via rotational movements of the catheter shaft 82 at the proximal region or end. If the tip 88 of the catheter 80 has a bend formed in it, such as shown in FIG. 4A, then the tip 88 can be rotated to facilitate passage through various anatomic structures in the nasal and paranasal region, such as through the ostium of a sinus.

FIG. 4B also illustrates a balloon dilation catheter 80 that incorporates a relatively large main lumen 96 large enough for a flexible endoscope 42 and an optional support tube 41 (as shown in FIGS. 4B, 6A, and 7B) to surround a portion of the flexible endoscope 42. In this embodiment, the tip of the endoscope 42 can be positioned at or near the tip 88. An optional guide wire 60 (seen in FIGS. 6A, 6B, and 6C) can be separately advanced ahead of the balloon dilation catheter 80 ahead of the catheter tip 88. FIGS. 6A, 6B, and 6C illustrate cross-sectional views of a catheter 80 taken along the lines B-B', C-C', and D-D', respectively showing a guide wire 60 positioned within a larger main lumen 96. The main lumen 96 may include a single large lumen 96 like that in FIG. 5 or it may include two, merged lumens like that shown in FIGS. 6A, 6B, and 6C.

However, in other instances it is desirable to provide a balloon dilation catheter 80 with a shorter tip or no tip 88. FIG. 7A illustrates one such embodiment where the distal tip 88 is relatively short, preferably about 1-3 mm in length, extending from the balloon cone portion (described below). In addition, the distal balloon "cone" region 94 is also relatively short, by virtue of having a relatively steep cone angle, preferably from about 45 degrees to about 90 degrees, and most preferably about 60 degrees. As used herein, the cone angle is the angle between the cone and the longitudinal axis of the catheter 80. A lumen 96 (best seen in FIGS. 7B and 7C) may extend through the balloon catheter 88 for passage of a flexible endoscope 42 and/or a wire guide 60 (not shown in FIGS. 7B and 7C). FIG. 7A illustrates in phantom (cone shaped) the field of view from the endoscope 42 located in the distal tip 88 of the balloon dilation catheter 80.

FIG. 7D illustrates another embodiment of a balloon dilation catheter 80 with no distal tip extending beyond the expandable balloon 86. In this embodiment, the balloon 86 preferably incorporates a "reverse" distal cone 95 where it is secured to the shaft 82 of the balloon dilation catheter 80. This embodiment may be useful in instances where dilation from the balloon 86 is preferred to extend as distally as possible within an anatomic structure. In this regard, the distal most portion of the balloon 86 is able to expand to substantially the maximum diameter of the balloon 86. For example, if the ostium of a sinus to be dilated is immediately adjacent to another structure just beyond it (e.g., the ethmoid bulla in the instance of a trans-canine fossa dilation of a maxillary sinus ostium), then it may be difficult to position the tip of the balloon dilation catheter 80 into that anatomy beyond the ostium. Therefore, a balloon dilation catheter 80 of the embodiment shown in FIG. 7D could be placed completely through the ostium, without needing to find a place to position a distal tip.

FIGS. 8A through 8F illustrate a balloon dilation catheter 80 having a relatively short curved distal tip 88 extending distally from the dilation balloon 86. The distal tip 88 may terminate in an optional bulbous end 88a as illustrated in FIGS. 8A and 8D. FIG. 8A illustrates the expandable balloon 86 in a deflated, folded, and wrapped condition. Cross-sectional images taken along the lines B-B' and C-C' are illustrated, respectively, in FIGS. 8B and 8C. In one aspect of the embodiment, the balloon 86 has at least two wings or appendages 86a when in a deflated condition (best seen in FIG. 8C). In the embodiment shown in FIG. 8A, four (4) such wings 86a are shown. Other numbers of wings 86a are contemplated, e.g., three, five, or more.

FIGS. 8D through 8F illustrate the balloon 86 in an inflated state, where the wings 86a unfold and the balloon 86 takes on a substantially cylindrical configuration. Cross-sectional views taken along the lines E-E' and F-F', respectively, are shown in FIGS. 8E and 8F. Preferably folds 86b (shown in FIG. 8F) are formed in the balloon 86 (e.g., by heat setting, crimping or the like) such that when the balloon 86 is deflated after an inflation, the folded wings 86a re-establish themselves, and the deflated balloon resumes a folded configuration (as shown in FIG. 8C). Re-establishing a folded configuration with multiple wings 86a on the balloon 86 as shown in FIG. 8C is helpful if the same balloon dilation catheter 80 is intended to be used to dilate an additional, e.g. second, sinus ostium.

Figure 9A:
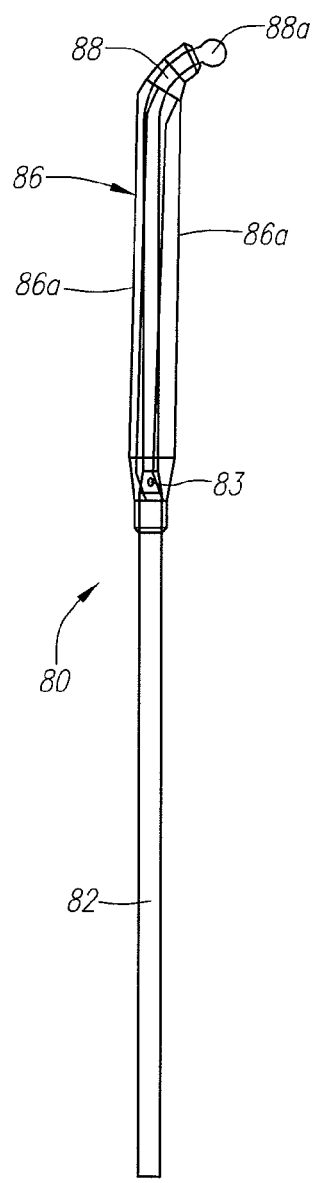
FIG. 9A illustrates a plan view of a balloon dilation catheter according to another embodiment.
Figure 9B:
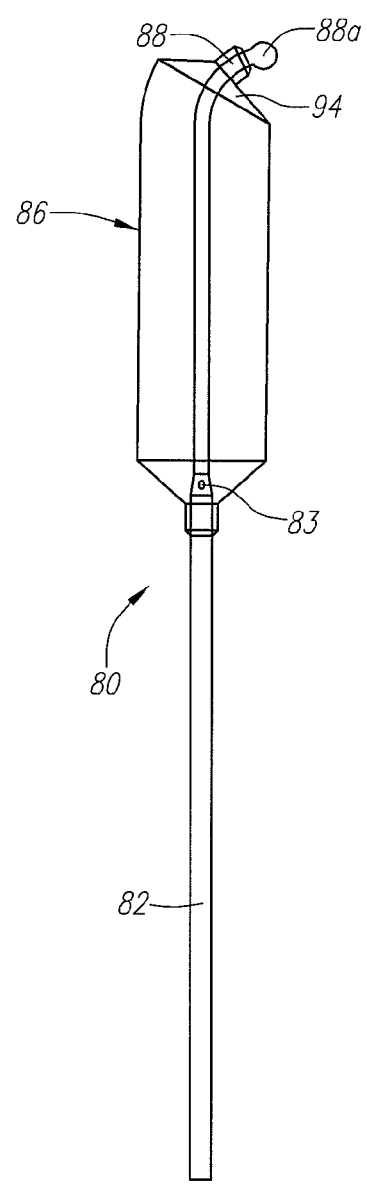
FIG. 9B illustrates a plan view of a balloon dilation catheter of FIG. 9A with the balloon in an expanded state.

FIGS. 9A and 9B illustrate another embodiment of a balloon dilation catheter 80 in which the distal region of the balloon 86 extends over a portion of a curved distal tip 88 disposed on the distal end of the shaft 82. As seen in FIG. 9A, the expandable balloon 86 includes a plurality of wings 86a although the wings 86a may be omitted in other embodiments. FIG. 9A shows the balloon 86 in a deflated state while FIG. 9B illustrates the balloon 86 in an inflated state. This embodiment allows for the balloon dilation catheter 80 to have a curved distal tip 88 while at the same time minimizing any added length that projects distally to the main body of the expandable balloon 86.

FIGS. 10A through 12F illustrate multiple embodiments of a balloon dilation catheter 80 having curved distal tips 88 and a shaft 82 which enables the curved tip 88 to be rotationally controlled via one or more manipulations on the proximal end (e.g., proximal hub 84) of the balloon dilation catheter 80 to facilitate navigation through the anatomy of the nasal and paranasal spaces, such as the ostia of the sinuses. Preferably, in both embodiments, the construction of the shaft 82 permits the distal tip 88 to be rotated in a substantially 1:1 relationship with rotational movement of the proximal end of the catheter 80. That is to say, if the proximal end of the balloon dilation catheter 80 is rotated through an angle of about 90°, the distal tip 88 is also rotated through an angle of about 90°. The embodiments illustrated in FIGS. 10A through 12F may include a lumen 96 for placement of a flexible endoscope, or they may not have such a lumen. If no such lumen is provided in the balloon dilation catheter 80, a flexible endoscope 42 may still be utilized to guide the positioning of the balloon dilation catheter 80, but will reside in a different component, as will be described later.

Figures 10A, 10D:
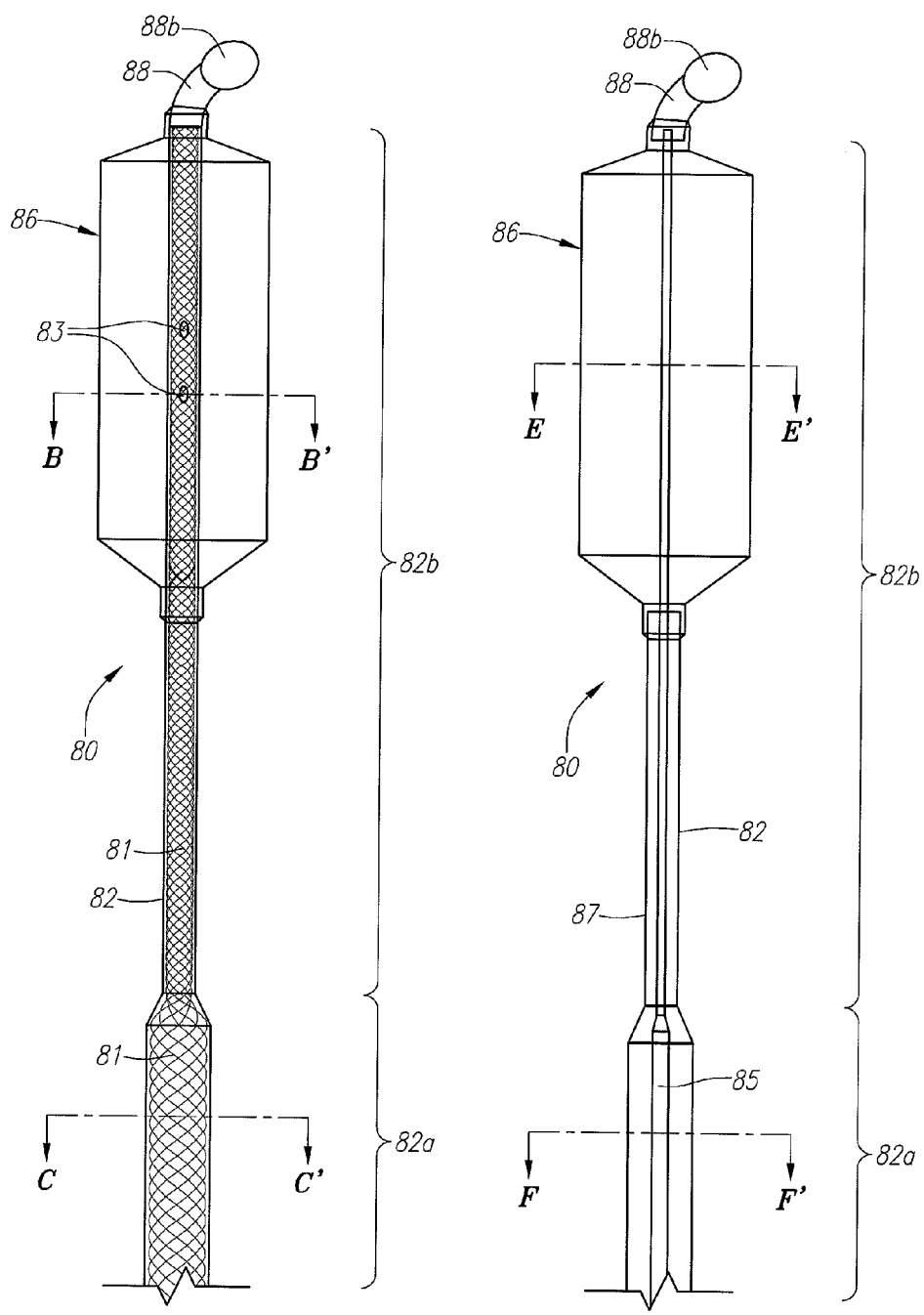
FIG. 10A illustrates a plan view of a balloon dilation catheter according to another embodiment. The shaft of the balloon dilation catheter is partially transparent illustrating a braid structure.
FIG. 10D illustrates a plan view of a balloon dilation catheter according to another embodiment. The shaft of the balloon dilation catheter is partially transparent illustrating an internal core wire.

FIG. 10A illustrates a balloon dilation catheter 80 having a shaft 82 having multiple regions (two as shown in FIGS. 9A-9C) which includes a proximal region 82a and a distal region 82b. It is contemplated that further additional regions (e.g., beyond two) could also be incorporated. In this embodiment, the proximal region 82a is a polymeric tube with an incorporated braid 81. Incorporation of a braid 81 significantly increases the torsional rigidity of the shaft 82. A lumen 90 (seen in FIGS. 10B and 10C) extends inside the shaft 82 for inflation and deflation of the expandable balloon 86. The distal region 82b of the shaft 82 is an extension of the proximal tubular member and may be formed by necking or shrinking the diameter of the tubing utilizing, for example, a heat forming process. The distal region 82b still includes the braid 81 albeit it at a reduced diameter. By reducing the diameter of the distal region 82b, the distal region 82b becomes more flexible, which facilitates its ability to navigate tortuous pathways within the nasal and paranasal spaces. One or more ports or passageways 83 (seen, for example, in FIGS. 8A, 8D, 9A, 9B, 10A and 10B) are disposed in the side wall of the distal region 82b within the balloon 86 to allow for fluid communication between the inflation lumen 90 and the balloon 86. As seen in FIG. 10A, the curved distal tip 88 is secured to the distal end of the braid-incorporated shaft 82 in the distal region 82b, however the curved distal tip 88 could also be formed as an extension of the braid-incorporated shaft 82. An optional bulbous tip 88b which may have an oval or olive-shape, (e.g., "olive tip") may also be incorporated to make the tip relatively atraumatic to the tissues it may encounter in the nasal and paranasal spaces. The curved distal tip 88 can be attached or formed by suitable means such as thermal bonding, adhesive bonding or thermal forming.

Figure 10B:
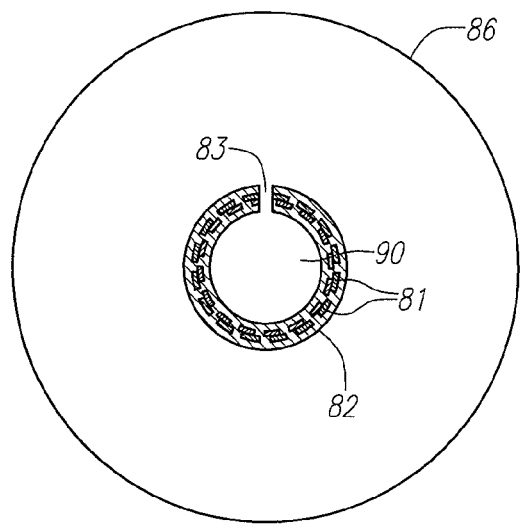
FIG. 10B illustrates a cross-sectional view the balloon dilation catheter of FIG. 10A taken along the line B-B'.
Figure 10C:
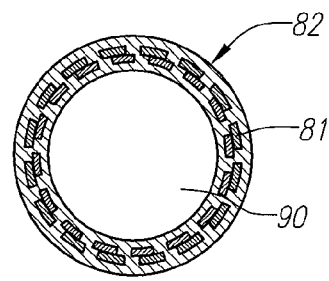
FIG. 10C illustrates a cross-sectional view the balloon dilation catheter of FIG. 10A taken along the line C-C'.
Figure 10E:
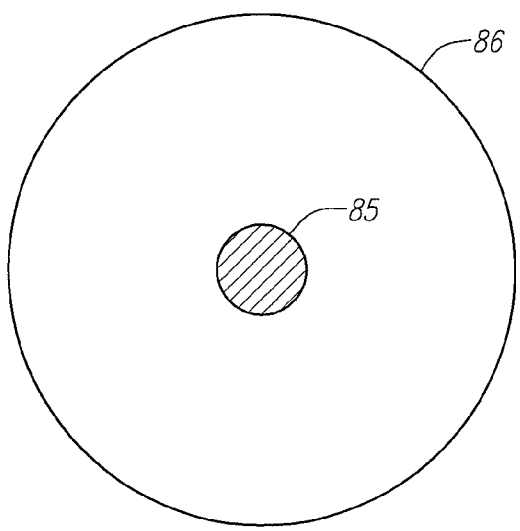
FIG. 10E illustrates a cross-sectional view the balloon dilation catheter of FIG. 10D taken along the line E-E'.
Figure 10F:
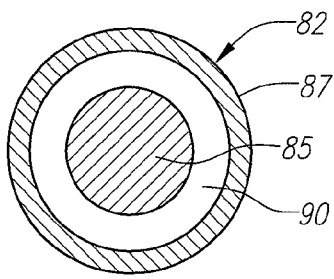
FIG. 10F illustrates a cross-sectional view the balloon dilation catheter of FIG. 10D taken along the line F-F'.

FIGS. 10D through 10F illustrate an embodiment wherein the torque is transmitted to the distal tip 88 via an internal core wire 85. A tubular outer jacket 87 surrounds the core wire 85 and defines the inflation lumen 90 there between (best seen in FIG. 10F). The tubular outer jacket 87 is preferably formed of a lubricious material such as high-density polyethylene, Nylon, or Pebax, and is secured to the proximal end of the balloon 86 by thermal or adhesive bonding. In this embodiment, the proximal end of the core wire 85 and the proximal end of the outer jacket 87 are preferably connected to a Luer fitting (not shown). The distal end of the core wire 85 is connected to the curved distal tip 88.

Rotation of the proximal end (e.g., Luer fitting) transmits rotation to the core wire 85, which in turn, transmits rotation to the distal tip 88. The core wire 85 may have a varying diameter along its length, being larger in the proximal region 82a and smaller in the distal region 82b. The core wire 85 could have one "step" as shown between the proximal region 82a and the distal region 82b, or the core wire 85 could have multiple steps in diameter or gradual changes in diameter. Alternatively, the transition may be smooth from the larger diameter of the proximal region 82a to the smaller diameter of the distal region 82b. A preferred core wire 85 may be formed of highly cold-worked stainless steel and may have a diameter in the proximal region 82a of around 0.018 inches to around 0.030 inches, and a diameter in the distal region 82b of around 0.005 to around 0.015 inches. Both the proximal region 82a and the distal region 82b could have multiple steps, or a gradually changing diameter between the above ranges.

Figure 11B:
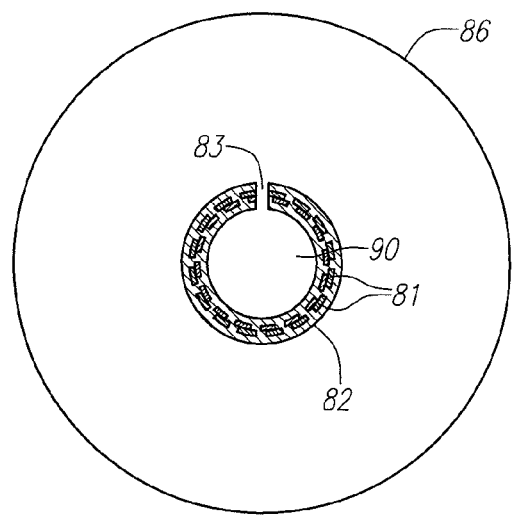
FIG. 11B illustrates a cross-sectional view the balloon dilation catheter of FIG. 11A taken along the line B-B'.
Figure 11C:
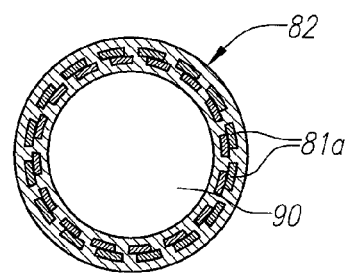
FIG. 11C illustrates a cross-sectional view the balloon dilation catheter of FIG. 11A taken along the line C-C'.

FIGS. 11A through 11C shows an embodiment of a balloon dilation catheter 80 having multiple, separate braided shaft components 81a, 81b connected together, rather than reforming a single braided shaft 81 configuration into multiple regions having differing characteristics, as illustrated in the embodiment of FIGS. 10A-10C. As best seen in FIG. 11A, the balloon dilation catheter 80 includes a proximal braided tubular shafts 81a and a distal braided tubular shaft 81b. Preferably, the outer diameter (OD) of the distal shaft 81b is small enough to be inserted into the internal diameter (ID) of the proximal shaft 81b to allow for some overlap between the two braided structures. The two braided segments 81a, 81b may be secured to each other by any suitable means such as the use of an adhesive or thermal bonding the two segments 81a, 81b. Additional polymeric material 103 (shown in FIG. 11A) may be optionally added to "backfill" the junction between the two segments 81a, 81b. The backfill material 103 may be additional adhesive or an addition thermoplastic polymer.

Figure 11E:
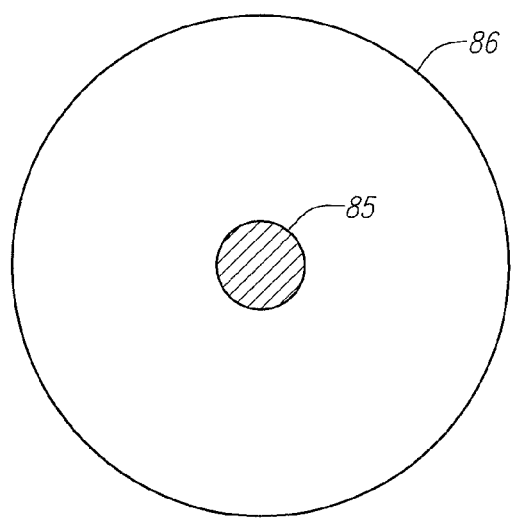
FIG. 11E illustrates a cross-sectional view the balloon dilation catheter of FIG. 11D taken along the line E-E'.
Figure 11F:
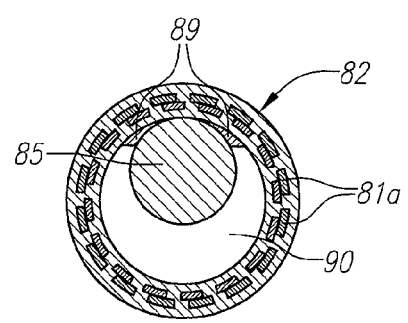
FIG. 11F illustrates a cross-sectional view the balloon dilation catheter of FIG. 11D taken along the line F-F'.

FIGS. 11D through 11F illustrate still another alternative embodiment of a balloon dilation catheter 80. The embodiment of FIGS. 11D through 11F makes use of a tubular braided shaft 81a for the proximal portion 82a of the catheter shaft 82 and a core wire 85 surrounded by a tube or jacket 87 for the distal portion 82b of the catheter shaft 82. The proximal end of the core wire 85 is secured to the distal end of the braided shaft 81a by suitable means such as adhesive 89, while the distal end of the core wire 85 is secured to the distal tip 88. Rotation of the proximal braided shaft portion 82a transfers rotation to the core wire 85 and, consequently, to the distal tip 88. In this embodiment, it is also contemplated that the proximal tubular braided shaft 81a could also be a solid-walled metal tube such as a stainless steel hypotube (or other material). The core wire 85 could then be secured to the distal end of the hypotube component by use of a weld, braze, solder, or adhesive 89.

Figure 12A:
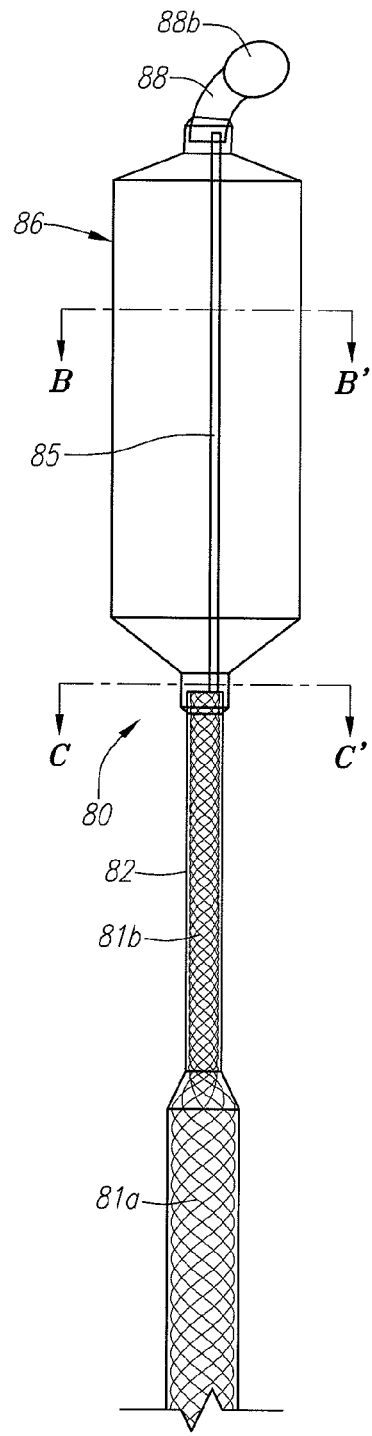
FIG. 12A illustrates a plan view of a balloon dilation catheter according to another embodiment. The shaft of the balloon dilation catheter is partially transparent illustrating a braid structure.
Figure 12D:
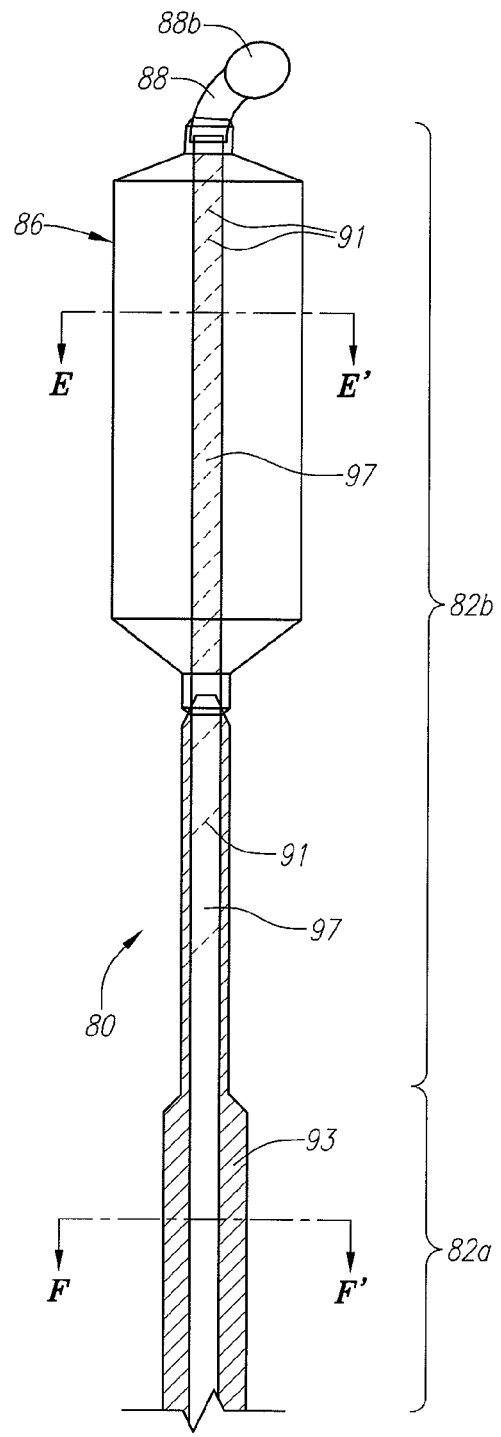
FIG. 12D illustrates a plan view of a balloon dilation catheter according to another embodiment. The shaft of the balloon dilation catheter is partially transparent illustrating a tubular (e.g., hypotube) shaft.
Figure 12B:
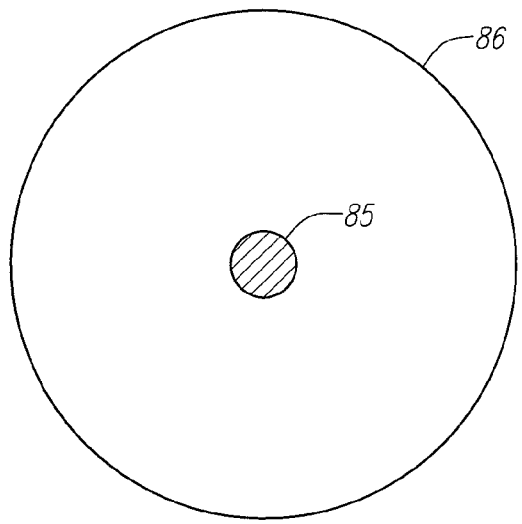
FIG. 12B illustrates a cross-sectional view the balloon dilation catheter of FIG. 12A taken along the line B-B'.
Figure 12C:
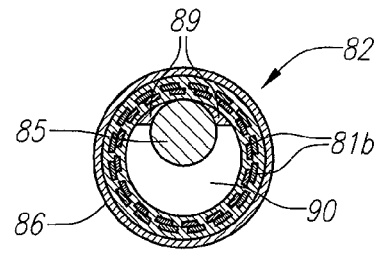
FIG. 12C illustrates a cross-sectional view the balloon dilation catheter of FIG. 12A taken along the line C-C'.

FIGS. 12A through 12C illustrate another alternative embodiment of a balloon dilation catheter 80. In the embodiment of FIGS. 12A-12C, the shaft 82 uses one or more tubular braided shaft components 81a, 81b (either separately formed and secured, or "reformed" form a single braided tubular shaft component 81) and a core wire 85, which extends from the distal end of the distal-most braided shaft 81b structure through the balloon 86 to the distal tip 88. In this embodiment, rotational movement of the proximal portion of the catheter shaft 86 is transmitted via the braided shaft region(s) (81 or 81a and 81b) to the core wire 85 and onto the distal tip 88. This embodiment is different from that disclosed in FIGS. 11D-11F in that the braided portion 81 extends further along the catheter shaft 86 until the proximal end of the balloon 86. Further, the core wire 85 is shorter, traversing across the interior of the balloon 86 until the distal tip 88. Bonding between the core wire 85 and braided shaft (e.g., 81 or 81b) may be as described above with respect to the embodiment of FIGS. 11D-11F.

Figure 12E:
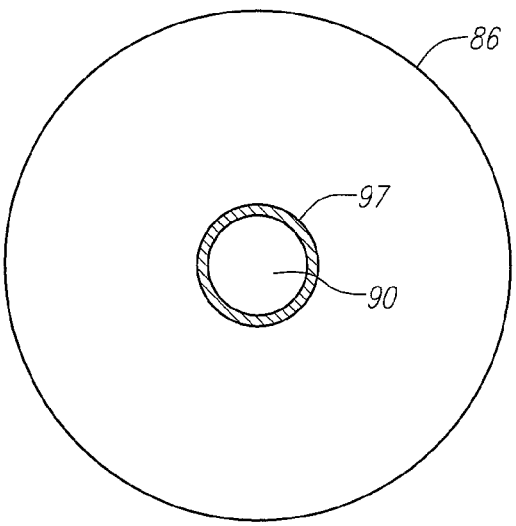
FIG. 12E illustrates a cross-sectional view the balloon dilation catheter of FIG. 12D taken along the line E-E'.
Figure 12F:
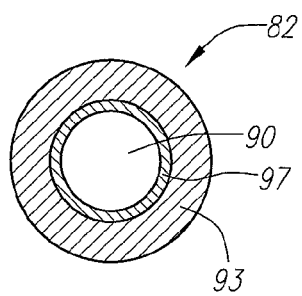
FIG. 12F illustrates a cross-sectional view the balloon dilation catheter of FIG. 12D taken along the line F-F'.

FIGS. 12D-12F illustrates still another alternative embodiment for a balloon dilation catheter 80. The embodiment of FIGS. 12D-12F uses a hypotube 97 for the shaft 82. The hypotube 97 of the proximal shaft region 82a is solid-walled, whereas the distal shaft region 82b has a pattern 91 cut into the wall which greatly increases the flexibility of the distal region, while maintaining significant torsional stiffness to facilitate torquing/rotation of the distal tip 88 which may optionally be curved and include a bulbous end 88b. There are numerous slot configurations which can accomplish this, including an "interrupted spiral" pattern 91 (as illustrated in FIG. 12D), or a series of interconnected rings. The pattern 91 may be formed in any number of ways known to those skilled in the art. This may include, for example, using a laser to cut such slots 91 within a tubular component such as metallic hypotube 97. The hypotube 97 may end at the connection with the distal tip 88 or, alternatively, the hypotube 97 can extend within a polymeric structure to create or form the curved distal tip 88. The slot pattern 91 may be uniform along the length of the distal shaft region 82b, or it can vary. Preferably the slot pattern 91 imparts greater flexibility in a distal direction along the distal shaft portion 82b. This may be accomplished, for example, by beginning with a coiled slot of a longer pitch proximally and becoming shorter in the distal direction. The proximal portion of the shaft 82a is preferably covered with a polymeric tube or jacket 93 to build up the diameter to facilitate hand manipulations. The polymeric tube 93 preferably extends to the balloon 86 as is shown in FIG. 12D, but is thinner in the distal portion 82b to facilitate higher flexibility. The polymeric tube 93 also serves to seal the slots 91 contained in the hypotube 97 that are located proximal with respect to the balloon 86. The slots in the hypotube 97 within the balloon 86 serve to conduct the inflation fluid to the balloon 86 for inflation and/or deflation.

In the embodiments of the balloon dilation catheter 80 described in FIGS. 10A through 12F, for use in dilating the maxillary sinus ostium/infundibulum via the canine fossa, the proximal region 82a may have an ID of around 0.025 inches and an OD of around 0.055 inches. The distal region 82b may have an ID of around 0.010 inches and an OD of around 0.030 inches. The length of the distal tip 88 may be about 3 mm to about 12 mm beyond the body of the balloon 86, and more preferably from about 7 mm to 10 mm beyond the body of the balloon 86 and may have between about 25-90° of curvature. If the optional bulbous or "olive tip" end 88b is used, it may have an OD of around 0.035 inches. The expandable balloon 86 may have a number of sizes depending on the application and anatomical peculiarities of the patient. For example, the balloon 86, when inflated, may have ODs of around 3, 5, and 7 mm.

If a braid 81 structure is employed, the braid 81 may have between 50-100 picks per inch and sixteen (16) or thirty-two (32) wires. The braid wire may be around 0.0005×0.002 up to 0.0015×0.005 ribbon (all in inches), and formed form stainless steel. Tubular materials such as that used for jackets 87, 93 may be formed from a polymeric material such as Nylon and Pebax 35D to 72D. The length of the body of the balloon 86 may vary from about 15 mm to about 25 mm but is preferably about 20 mm in length. The balloon 86 may be formed from a number of polymeric materials including, for example, PET, Nylon 12, Pebax, and may be blow molded. Bonding between the balloon 86 and the shaft 82 of the balloon dilation catheter 80 may be accomplished using heat bonding or adhesive bonding.

The total length of the balloon dilation catheter 80 may vary, in part because of the length of the cannula 20, but the balloon dilation catheter 80 generally has a length within the range of about 20 to about 40 cm. If a distal shaft portion 82b is used, it is at least as long as the balloon 86 an may extend proximally, distally, or both with respect to the ends of the balloon 86.

It should be understood that the dimensions and materials discussed above are exemplary and meant to be illustrative of the dimensions and materials contemplated to be used in connection of the apparatus 10. Dimensions and materials falling outside of the list and ranges mentioned above may still fall within the scope of the invention.

Figure 13A:
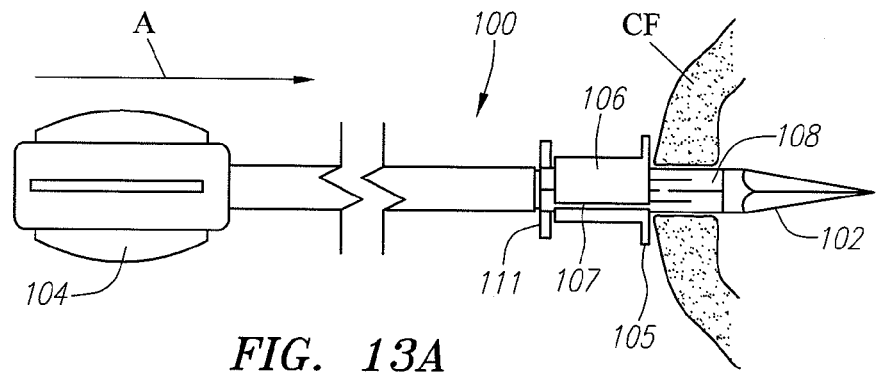
FIGS. 13A-C illustrate a piercing tool such as a trocar along with a sheath and stop being used to form an artificial opening or passageway into a sinus cavity via the canine fossa.
Figure 13B:
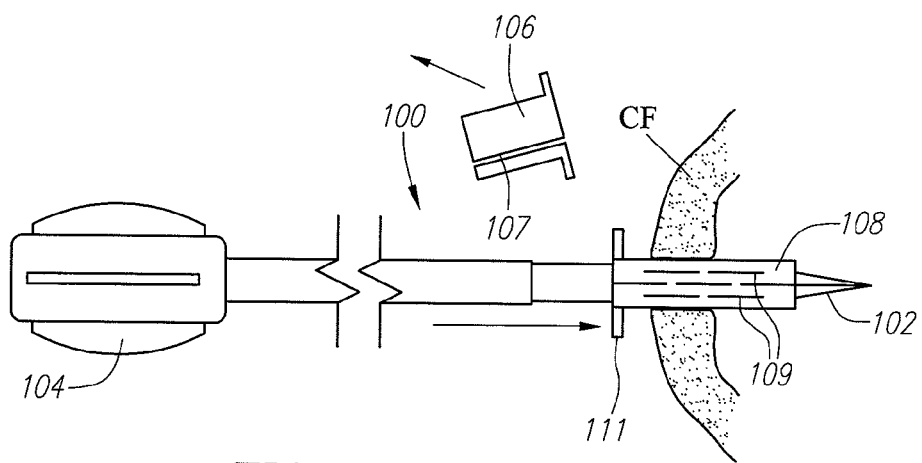
Figure 13C:
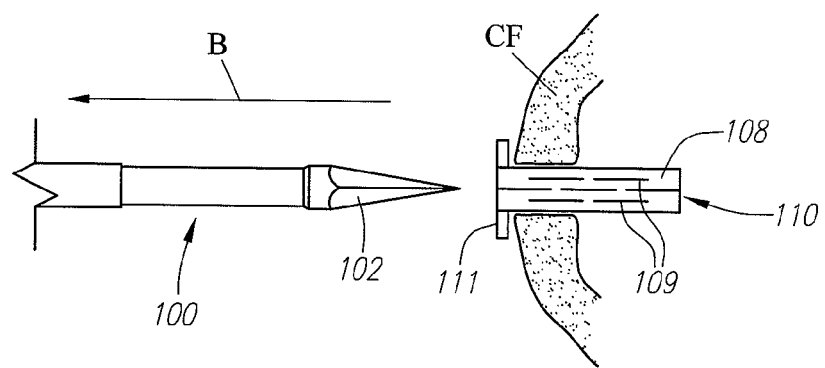
Figure 14:
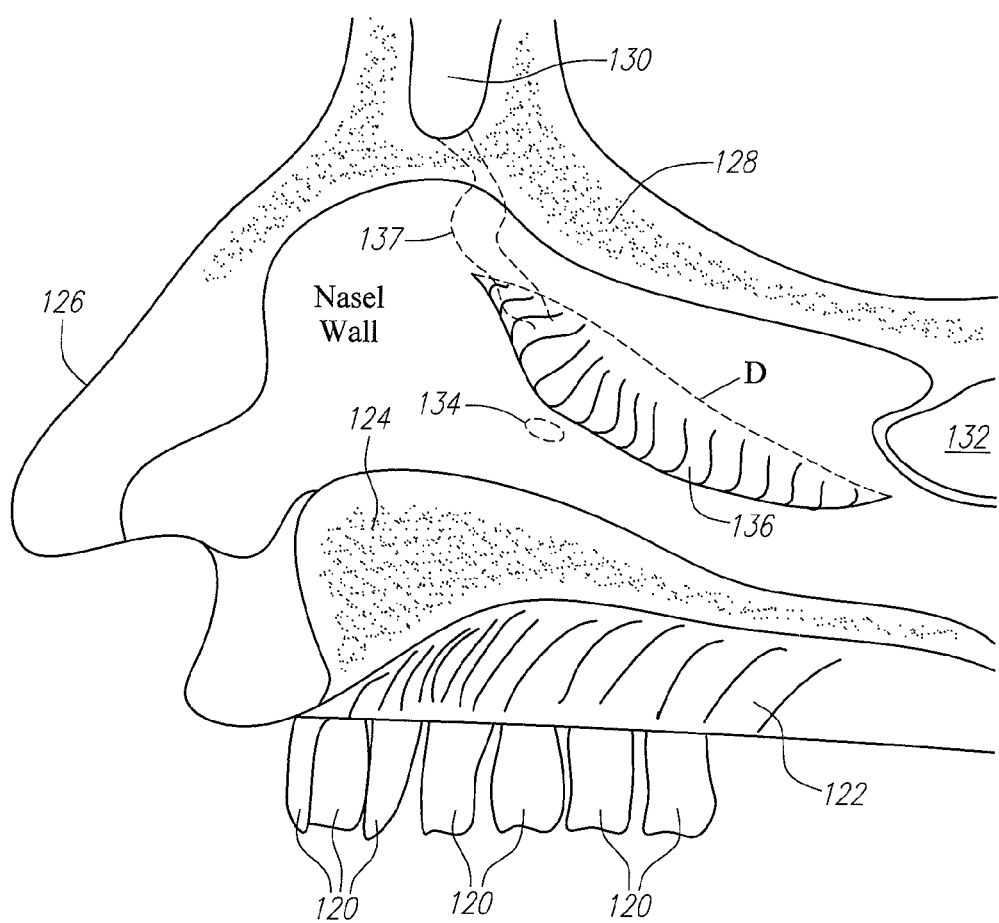
FIG. 14 illustrates a sagittal cross-sectional view of a portion of a patient's skull illustrating various anatomical features of the nasal cavity.

FIGS. 13A through 13C illustrate a method of forming and maintaining an access passageway to the maxillary sinus via the canine fossa (CF) region of a patient. FIG. 13A illustrates a piercing tool 100 such as a trocar loaded with the sheath 108 as well as the stop 106. The piercing tool 100 may be made of a metallic material such as stainless steel and may have a diameter at least as large as the cannula 20 that will then be used to access the anatomy of interest. In FIG. 13A, the sheath 108 is partially obstructed from view by the stop 106. The piercing tool 100 includes a proximal handle 104 that is grasped by the physician or other health professional that performs the operation. The piercing tool 100 further includes a sharpened distal tip 102 that will be used to tissue the soft tissue/bony structure of the canine fossa CF region (or other soft tissue/bony structure). The sharpened distal tip 102 may be a multi-faceted type (e.g., three facets) as illustrated in FIG. 13A. A multi-faceted tip 102 allows for the trocar 100 to be introduced into the soft tissue of the gums until in encounters the bony structure defining the sinus cavity.

As seen in FIG. 13A, the piercing tool 100 is advanced in the direction of arrow A to initially pierce or puncture the gum of the patient. Once the bony structure of the sinus cavity is reached, the trocar 100 may be rotated back and forth (e.g., clockwise then counter-clockwise or vice versa) while light pressure in the direction of arrow A is applied. The trocar 100 essentially drills into the bone until it enters the sinus cavity. As seen in FIG. 13A, the removable stop 106 prevents the trocar 100 from penetrating too deep into the sinus cavity which could inadvertently puncture the other side of the cavity or other anatomical spaces. The stop 106 mechanically interacts with the trocar 100 such that it is prevented from moving proximally along the trocar 100, as will become clear below. The stop 106 may include a flange 105 located at one end of the stop 106 that is large enough to atraumatically prevent the trocar 100 from advancing too far. For example, the flange 105 may extend about the periphery of the stop 106 and have an outer diameter that is about 1 mm to about 5 mm larger than the OD of the trocar 100. After access is made to the sinus cavity, the removable stop 106 may be removed from the trocar 100 as is shown in FIG. 13B. The longitudinal slit 107 in the stop 106 permits the stop 106 to be "peeled off" the trocar 100.

With reference now to FIG. 13B, once the stop 106 is removed, the sheath 108 (which is mounted on the shaft of the trocar 100) is advanced into the access passageway formed in the canine fossa CF region until a flange 111 on the proximal end of the sheath 108 abuts the external tissue. The sheath 108 is preferably formed from a thin-walled tube, which may be polymeric or metallic. For example, the sheath 108 may be stainless steel or a nickel titanium alloy (e.g., NITINOL), with a series of slots 109 cut into it to allow for diametric and lateral flexibility. The sheath 108 may be between 0.002 inches and 0.006 inches thick and between about 1 cm and about 3 cm long, with an initial outer diameter equal to or slightly smaller than the outer diameter of the trocar tip 102. Initially the sheath 108 sits in a recess on the shaft of the trocar 100. This enables the sheath 108 to be advanced into the soft tissue and the bone without catching or hanging on the tissue. The recess is preferably at least as deep as the wall thickness of the sheath 108, but may also be deeper, such that when assembled, the outer diameter of the trocar tip 102 is larger than the outer diameter of the sheath 108. In this manner, the hole formed by the trocar tip 102 is somewhat larger than the sheath 108. This diameter difference enables the sheath 108 and subsequent tools such as the cannula 20 to be more easily manipulated within the sinus cavity. Also, the proximal ledge of the recess prevents proximal movement of the sheath 108. The flange 111 on the sheath prevents proximal movement of the stop 106. Once the sheath 108 is fully inserted, the tip 102 of the trocar 100 is pulled back from the sheath 100 in the direction of arrow B, as depicted in FIG. 13C. The sheath 108 is now positioned within the access passageway and is used to maintain a lumen 110 through which the various devices may pass during the remainder of the procedure.

FIGS. 14-18 illustrate various cross-sectional representations of the right nasal cavity of a subject. The right nasal cavity is shown but the description applies equally to the left side as well. FIGS. 14-18 generally illustrate the teeth 120, roof of the mouth 122, the palate 124, the nose 126, portions of the skull 128, the lower part of the right frontal sinus cavity 130, and a portion of the right sphenoid sinus cavity 132. The dotted circular line 134 is the ostium of the right maxillary sinus, which sits in a structure lateral to the nasal wall. The flap-like structure 136 is the middle turbinate. The channel 137 (shown as a dashed line going in the superior or vertical direction) going up to the right frontal 130 sinus is also depicted, as it is lateral to the nasal wall. The dashed line D just above the middle turbinate 136 depicts the site of attachment (shown as attached to the nasal wall but this can vary in different patients).

Figure 15:
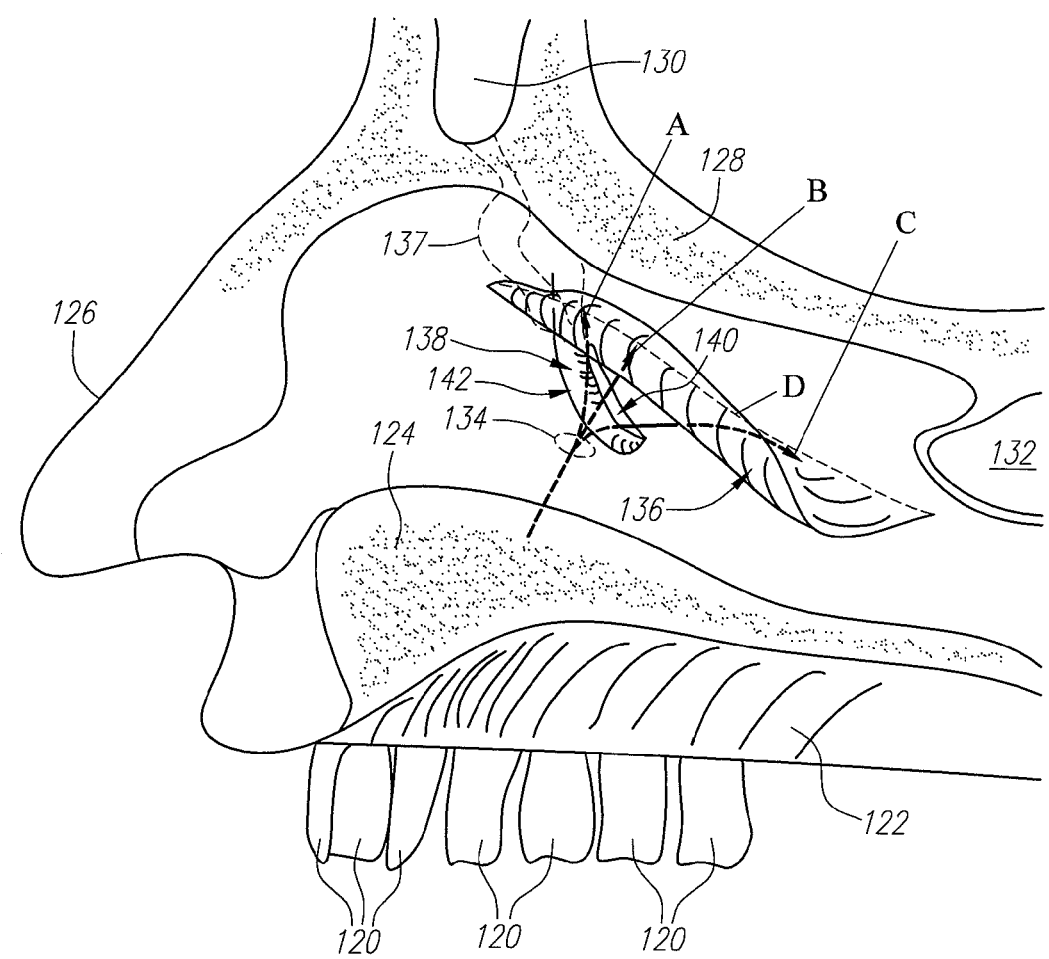
FIG. 15 illustrates a sagittal cross-sectional view of a portion of a patient's skull illustrating various anatomical features of the nasal cavity. The middle turbinate is lifted to reveal, among other structures, the uncinate process. Also shown are three different directions extending from the maxillary sinus cavity through the ostium infundibulum and nasal cavity.

FIG. 15 illustrates various anatomical structures of the nasal cavity that are located "underneath" or lateral to the middle turbinate 136. For illustration purposes, the middle turbinate 136 in FIG. 15 has been lifted up to reveal the uncinate process 138 which is a rim of mucosa covered bone extending medially from the lateral nasal wall and it is anterior to the hiatus semilunaris 140, the opening between the edge of the uncinate process 138 and the more posterior ethmoid bulla (not shown). The "pocket" underneath or lateral to the uncinate process is the ethmoid infundibulum 142. The ethmoid infundibulum 142 as well as the ostium 134 and the hiatus semilunaris 140 associated with the maxillary sinus can all be quite narrowed in a patient with suspected sinusitis. This narrowing can be a combination of inflammation of the mucosa, scar tissue, mucous, pus, polypoid tissue, narrowed underlying bony structure, or other pathology. The three arrows A, B, C in FIG. 15 indicate the three general directions extending from the maxillary sinus cavity through the ostium 134 and nasal cavity. The first direction, represented by arrow A, is a generally superior direction, towards the frontal recess and frontal sinus. The second direction, represented by arrow B in FIG. 15, is a "straight shot" out of the ostium 134 to and across the ethmoid bulla and towards the attachment point A of the middle turbinate 136. The third direction, represented by arrow C in FIG. 15 is posterior, generally running parallel to the attachment ridge or line of the middle turbinate 136.

Figure 16:
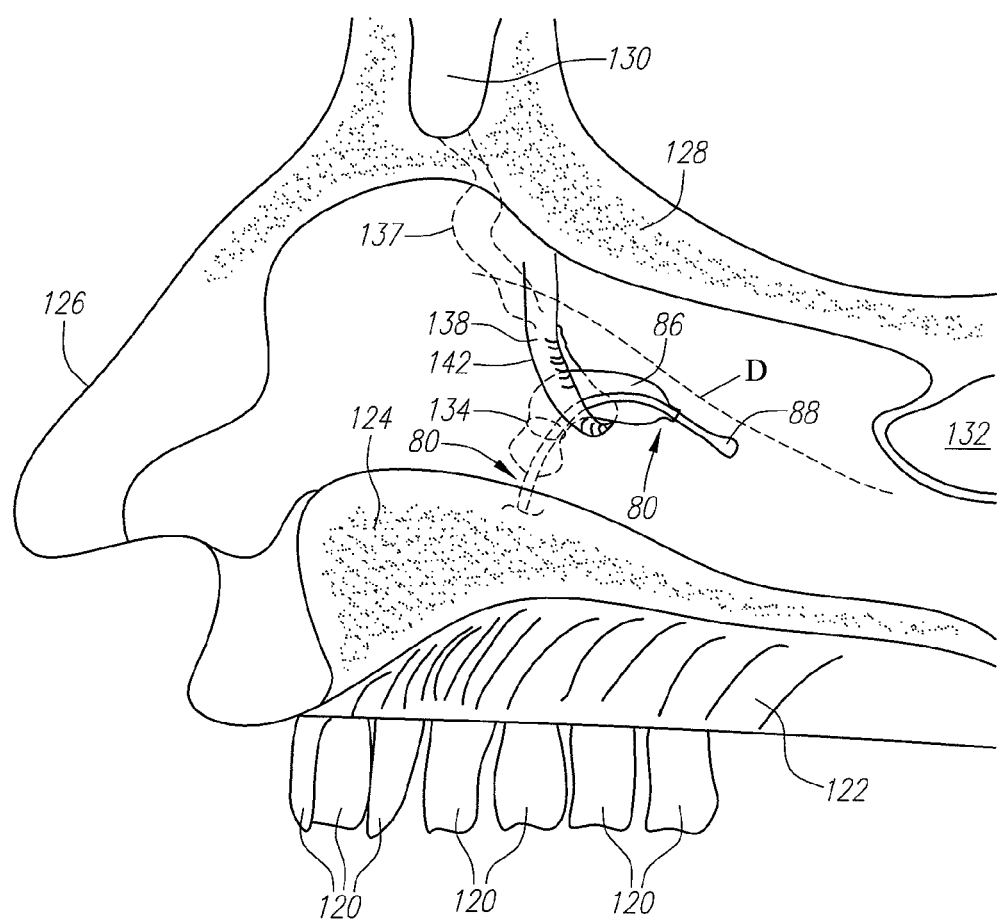
FIGS. 16 and 17 illustrates a sagittal cross-sectional view of a portion of a patient's skull like that shown in FIG. 15 with the middle turbinate removed. Also illustrated is a balloon dilation catheter being positioned across the ostium and other anatomical features for dilation.

FIG. 16 illustrates in partial phantom the distal end of a balloon dilation catheter 80 positioned in the maxillary sinus ostium 134. As shown, the distal tip 88 and the expandable balloon 86 are shown passing through the infundibulum 142, lateral to the uncinate process 138, and curving in a posterior direction (e.g., along path C in FIG. 15). For illustration purposes, the middle turbinate 136 is shown removed to allow better viewing of the balloon 86. The posterior placement of the balloon dilation catheter 80 is a preferred position for purposes of dilating the maxillary sinus ostium 134, infundibulum 142, and uncinate process 138. The balloon dilation catheter 80 shown here has a distal tip 88 to help facilitate placement of the balloon 86 in the posterior direction. The previously described embodiments of balloon dilation catheters 80 with distal tips 88 are preferred for such placement, and would facilitate such placement.

Figure 17:
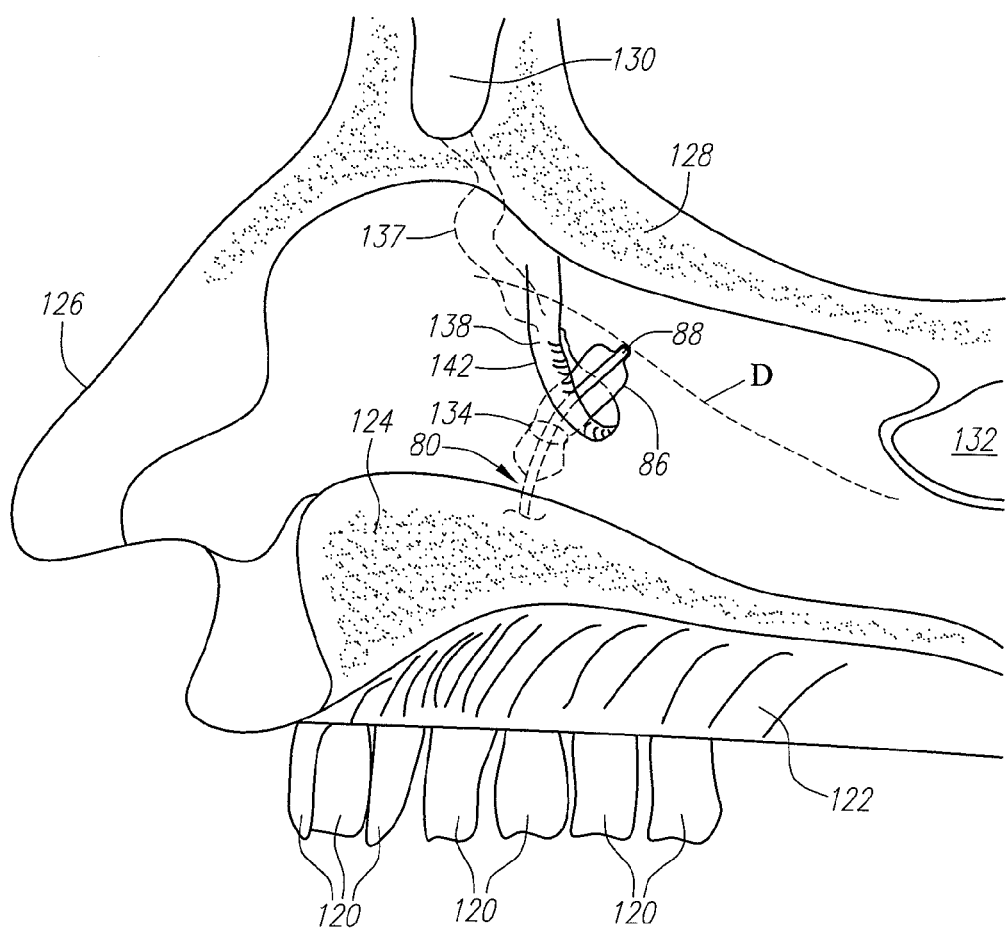
Figure 18:
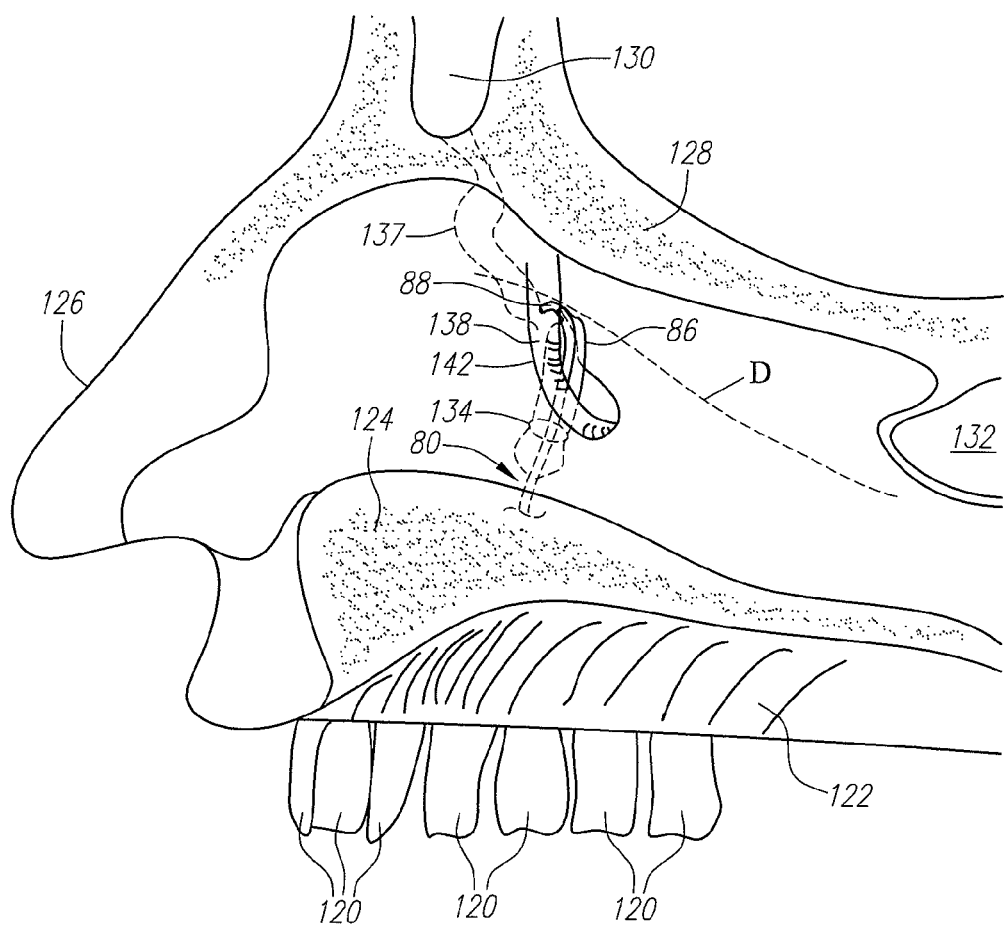
FIG. 18 illustrates a sagittal cross-sectional view of a portion of a patient's skull like that shown in FIG. 15 with the middle turbinate removed. Another embodiment of a balloon dilation catheter is shown crossing the ostium and other anatomical features.

FIG. 17 illustrates a balloon dilation catheter 80 positioned in the "straight shot" direction (i.e., direction of arrow B in FIG. 15) as the balloon 86 emerges from the ostium 134 and infundibulum 142. To facilitate the balloon 86 being positioned in this direction, it is preferred to utilize a balloon 86 with a short distal tip 88 (as shown), or no tip. FIG. 18 illustrates a balloon dilation catheter 80 with the balloon 86 positioned in a superior direction (i.e., in the direction of arrow A of FIG. 15) as the balloon 86 emerges from the ostium 134 and infundibulum 138. To place a balloon dilation catheter 80 in this position, it is preferred to make use of a balloon dilation catheter 80 with a curved distal tip 88 as shown in FIG. 18 and described in more detail herein. More preferably, a balloon dilation catheter 80 is used that has a "torqueable" curved distal tip 88 that can be controllably rotated. For example, rotation of the proximal end or region of the balloon dilation catheter 80 translates into a rotating or torquing movement of the curved distal tip 88.

In one aspect, the balloon dilation catheter 80 is initially placed inside the ostium 134 in the posterior direction. The distal tip 88 can then be re-oriented by a rotational movement of the distal tip 88 (e.g., by rotation of the proximal end or region of the balloon dilation catheter 80) and further advanced in re-oriented direction (e.g., the medial direction).

Turning now to FIGS. 19-22, a method of treating sinusitis is illustrated using a apparatus 10 in which the imaging tool 40 (e.g., endoscope 42) and balloon dilation catheter 80 are positioned using a guide wire 60. In the method illustrated in FIGS. 19-22, an access passageway has been made in the canine fossa region CF using the piercing tool 100 described in more detail herein (e.g., shown in FIGS. 13A-13C). While access to the maxillary sinus is made through the CF region, access to the maxillary sinus or other sinus cavity may be made through a trephination or the like through which a dilation balloon catheter 80 of the type described herein is placed.

Figure 19:
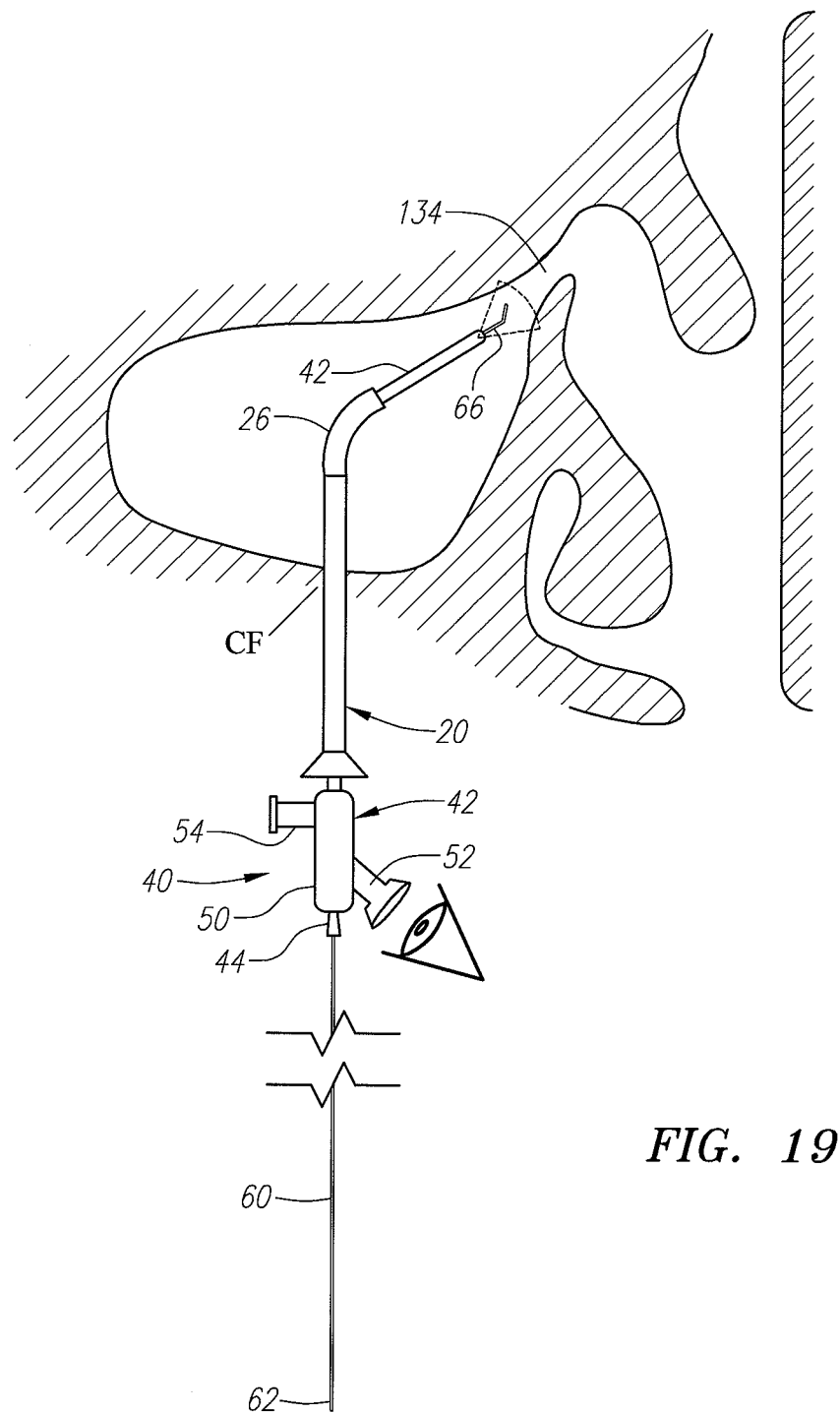
FIG. 19 illustrates a coronal partial cross-sectional view of the maxillary sinus of a patient or subject with a cannula or guide catheter that is positioned at least partially within the maxillary sinus cavity via an access point (e.g., canine fossa). A guide wire and a visualization tool (e.g., endoscope) are shown passing through the cannula or guide catheter to view the ostium.

Initially, FIG. 19 illustrates a cannula 20 positioned within the artificial opening or passageway formed in the canine fossa region CF. FIG. 19 omits the sheath 108 but in other embodiments, the cannula 20 may be passed through a temporary sheath 108 that is placed in the newly formed opening. The cannula 20 is shown having a curved distal tip 26 to better allow access toward the ostium 134 and associated infundibulum. An imaging tool 40 such as a flexible endoscope 42 has been placed within that cannula 20 and over the guide wire 60. In this regard, the endoscope 42 incorporates a guide wire lumen 56 as shown in FIG. 1A (hidden from view in FIG. 19) such that the endoscope can be slide over the guide wire 60.

FIG. 19 illustrates a curved (e.g., "j" bend or the like) distal tip 66 of the guide wire 60 projecting from the distal end of the endoscope 42, the orientation of which can be controlled by manipulating the proximal end 62 of the guide wire. FIG. 19 illustrates a person such as a physician or the like looking through the eyepiece 52 of the endoscope 42 to view the ostium 134 and associated infundibulum. Optionally, the eyepiece 52 could be hooked up to a camera and monitor (not shown). The field of view of the endoscope 42 is shown (dashed conical region) projecting from the distal end 48.

Figure 20:
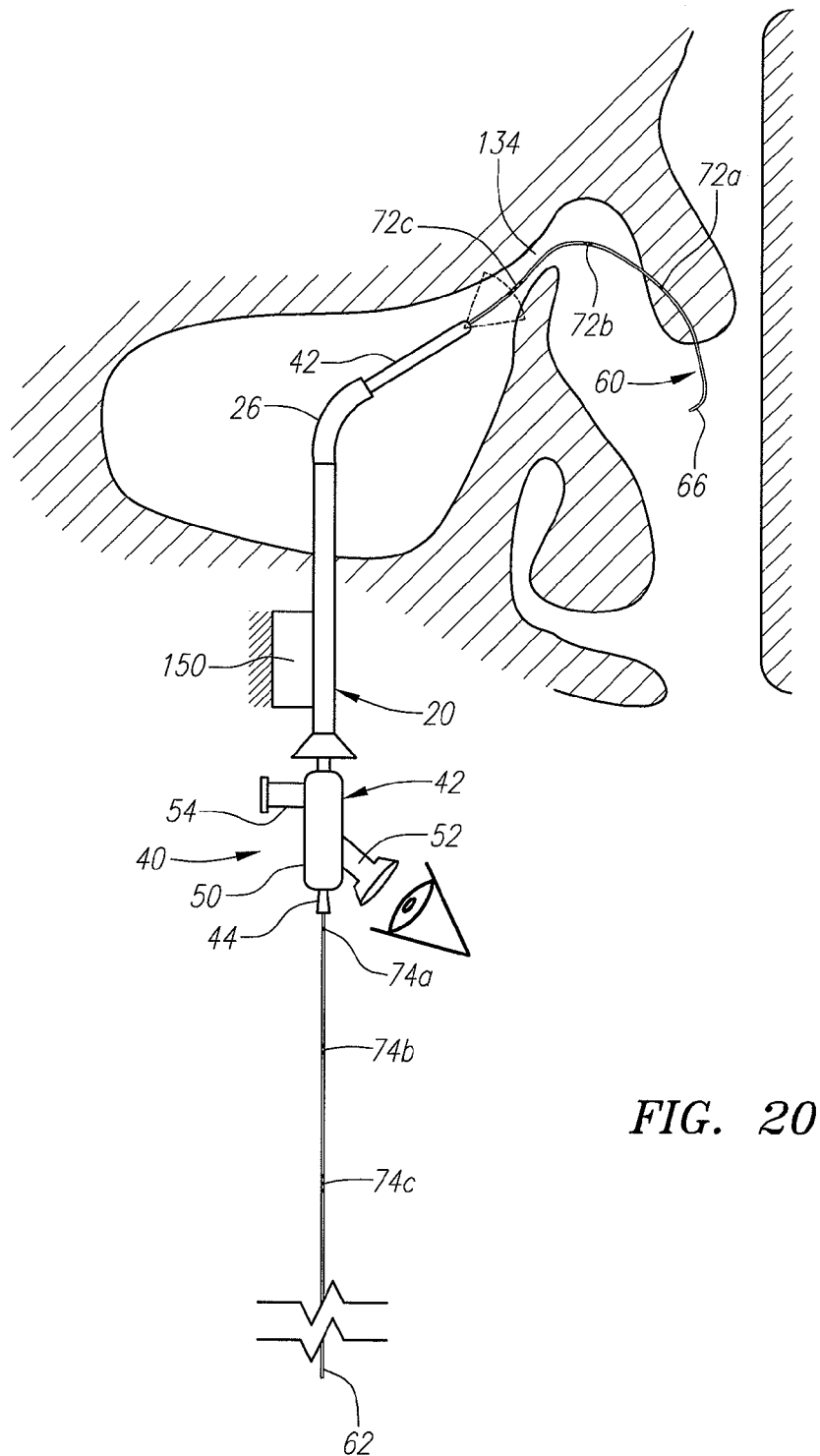
FIG. 20 illustrates the partial cross-sectional view of FIG. 19 wherein the guide catheter is fixed relative to the patient. In addition, the guide wire is shown in an advanced state wherein the guide wire has advanced in the distal direction across the ostium and into the nasal cavity.

Referring now to FIGS. 19 and 20, the cannula 20 is manipulated to aim the guide wire 60 to the ostium 134, using the endoscopic image to guide the manipulation. In FIG. 20, the guide wire 60 is shown being advanced across the ostium 134 and into the nasal cavity. The guide wire 60 preferably incorporates a series of visible markers 72a, 72b, and 72c on the distal portion 66. Corresponding visible markers 74a, 74b, and 74c are located on the proximal portion 62 and are spaced a known distance from the corresponding visible markers 72a, 72b, 72c on the distal end 66. For example the distal markers 72a, 72b, 72c could be different colors. Alternatively, the first mark (e.g., most distal mark) could have one configuration or appearance, e.g. a single mark (as shown in FIG. 20), and the second marker (from the distal tip) could be of a different configuration or appearance (e.g., two marks as shown in FIG. 20). FIG. 20 shows a third marker 72c (from the distal tip) that is formed from three (3) marks. The distance between the first mark 72a on the distal portion 66 and the corresponding first mark 74a on the proximal portion 62 would be predetermined. The distance between the second mark 72b on the distal portion 66 would be the same predetermined distance to the corresponding second mark 74b on the proximal portion 62. Similarly, the distance between the third mark 72c on the distal portion 66 would be the same predetermined distance to the corresponding third mark 74c on the proximal portion 62.

Figure 21:
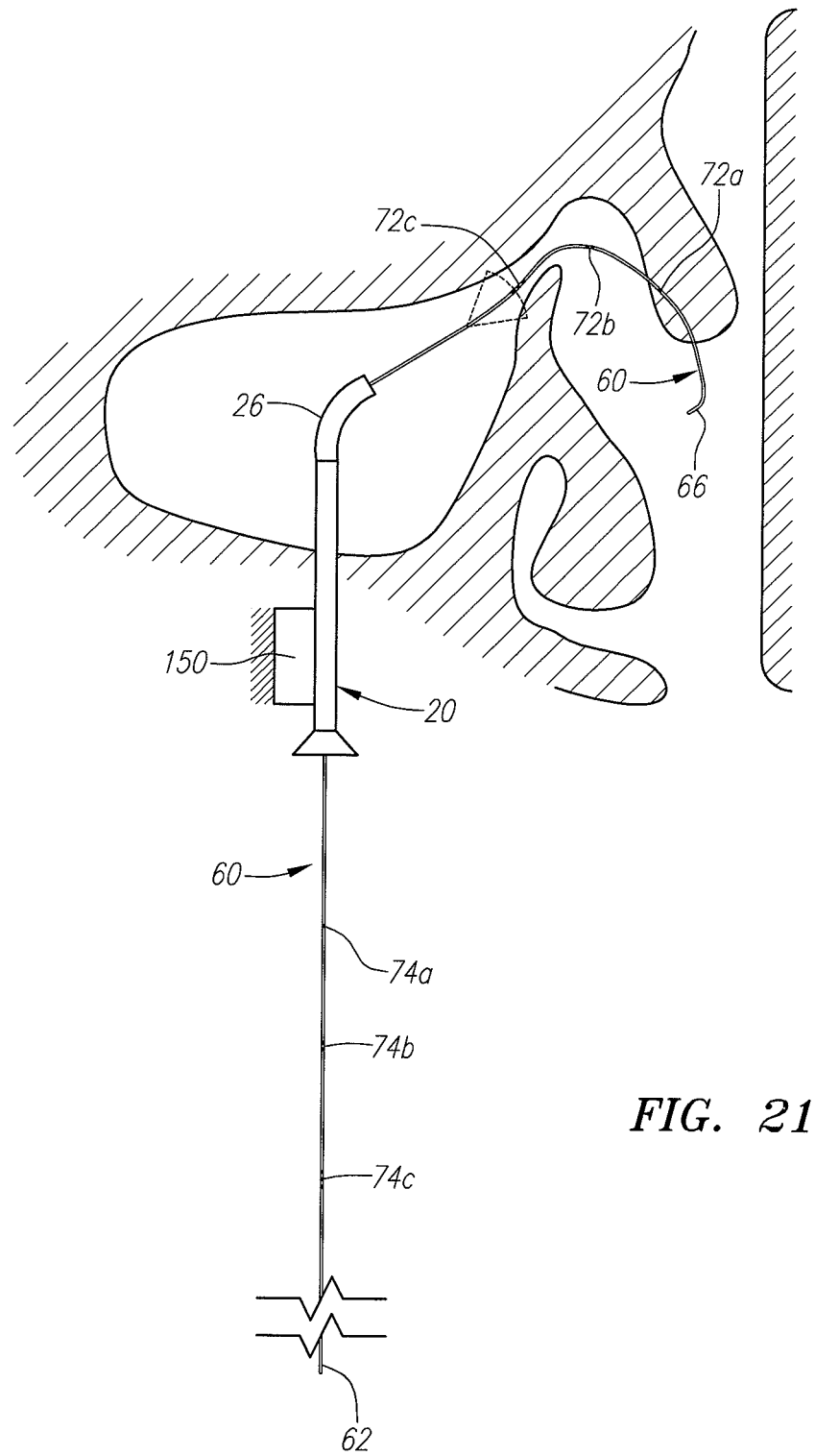
FIG. 21 illustrates the partial cross-sectional view of FIG. 20 wherein the endoscope has been removed.

The particular marker at or near the ostium 134 is noted. The endoscope 42 is then removed from the guide wire 60, as shown in FIG. 21, leaving the guide wire 60 in place through the cannula 20 and positioned across the ostium 134. As shown in FIG. 21, the cannula 20 is kept in a stable position using a stabilizing member 150 to keep its position relative to the ostium 134 constant. For example, a stabilizing member of the type described in U.S. patent application Ser. No. 11/379,691 may be used to stabilize the cannula 20. The '691 Application is incorporated by reference as set forth fully herein. Alternatively, the operator can manually stabilize the position of the cannula 20 with his/her hands.

Figure 22:
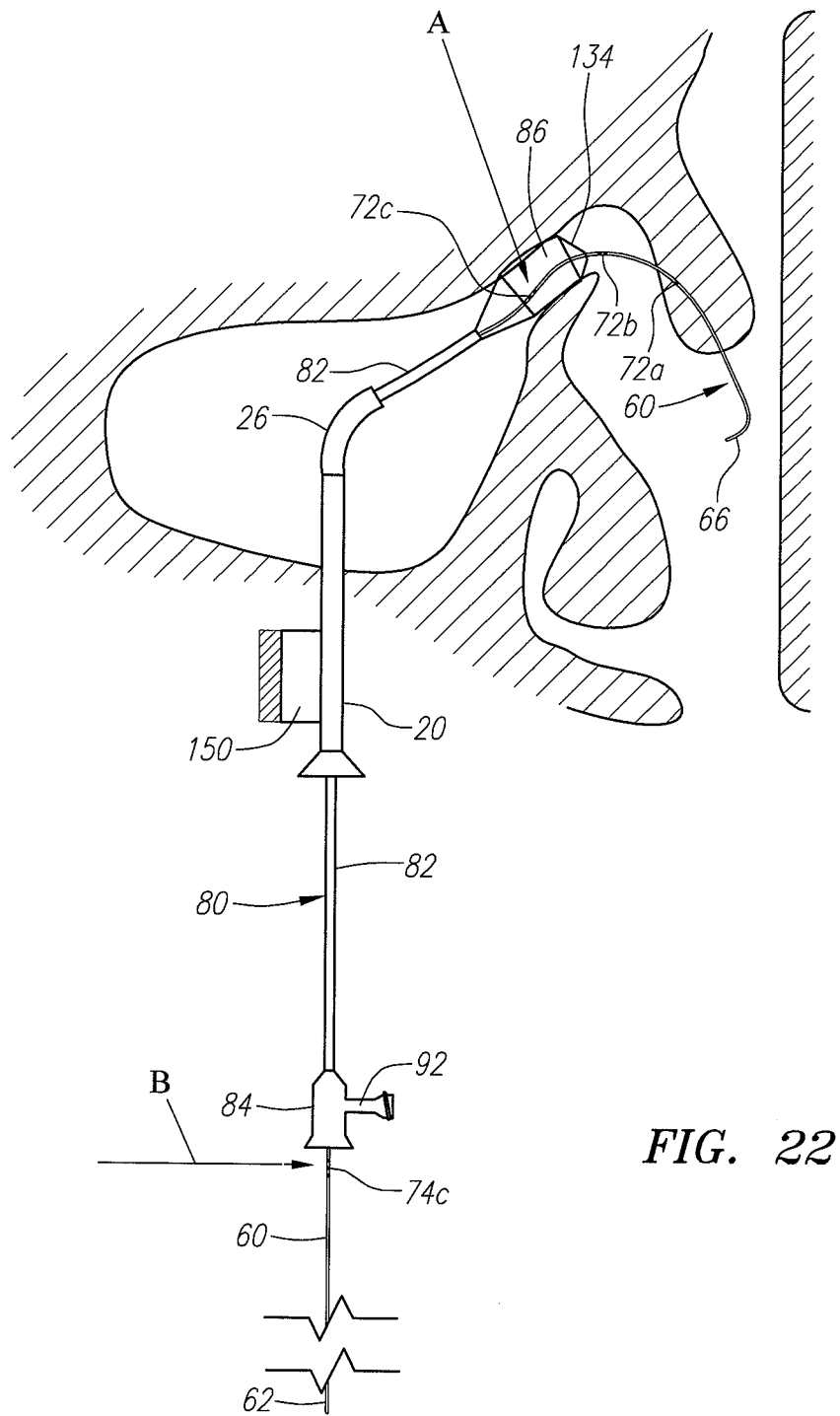
FIG. 22 illustrates the partial cross-sectional view of FIG. 21 wherein a balloon dilation catheter has been advanced over the guide wire and the balloon has been dilated within the ostium.

Next with reference to FIG. 22, a balloon dilation catheter 80 is then positioned over the guide wire 60. A reference length on the balloon dilation catheter 80 corresponds to the distance between the sets of visible markers on the guide wire 60. For example the distance between the corresponding distal mark 72c and proximal mark 74c on the guide wire 60 could be equal to the distance between the midpoint of the balloon 86 and the proximal end 84 of the balloon dilation catheter 80. In this manner, the midpoint of the balloon 86 would be at or near where the previously noted mark 72c (shown by arrow A in FIG. 22) on the guide wire 60 was located, just as the corresponding mark 74c (shown by arrow B in FIG. 22) on the proximal portion comes into view behind the proximal end 84 of the balloon dilation catheter 80.

Figure 23:
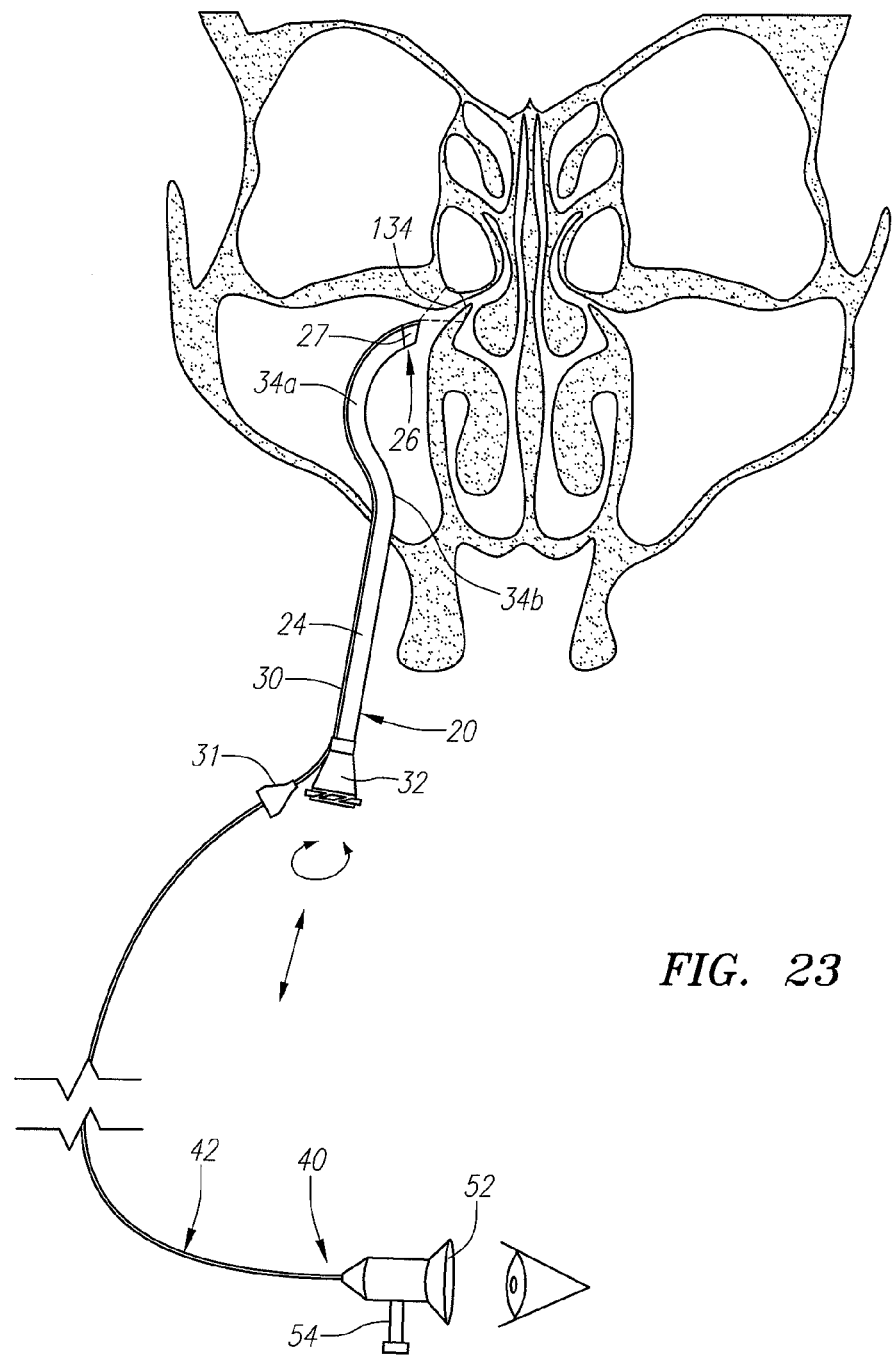
FIG. 23 illustrates a coronal cross-sectional view of the body structure of the skull defining the sinus cavities. A cannula and endoscope are shown accessing the maxillary sinus via the canine fossa region.
Figure 25:
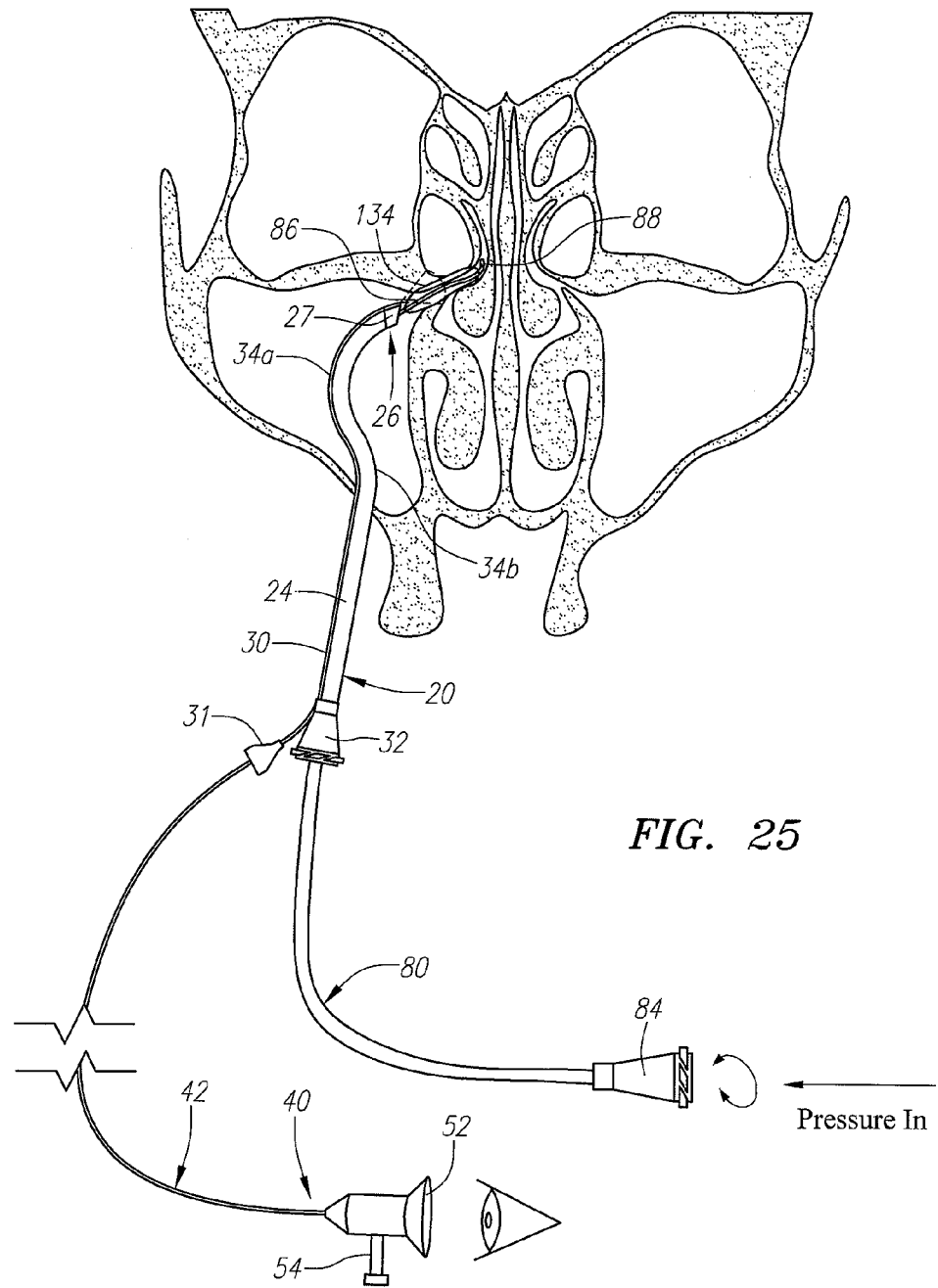
FIG. 25 illustrates the same view of FIG. 24 but with the balloon of the dilation catheter in an inflated state.

FIGS. 23-25 illustrate still other embodiments of treating sinusitis with the apparatus 10 described herein. FIGS. 23-25 illustrate a method of using a balloon dilation catheter 80 to dilate the ostium 134 of the maxillary sinus and the infundibulum space and the uncinate process. Though not illustrated, the same devices and sub-components described herein could be applied to other sinuses beyond the maxillary sinus, such as the frontal sinus, where the access could be made through a trephination of the frontal sinus to gain access to the cavity, and thereafter dilating the frontal sinus ostium and frontal recess area via the trephination access site using a balloon dilation catheter 80 and delivery system of the type described herein.

FIG. 23 illustrates the bony structure of the skull defining the sinus cavities. In this embodiment, a cannula 20 such as the one described with respect to FIG. 2G (or any above described cannula 20 with a secondary channel or lumen 30) is positioned in an access hole or passageway created at or near the canine fossa CF region and advanced into the maxillary sinus. An optional sheath 108 (not shown in FIGS. 23-25) may be used to maintain an open passageway and prevent the distal end of the imaging tool 40 from being obscured from blood or other biological material while it is advanced into the sinus cavity. In one aspect of the procedure, the patient is given a local anesthetic (with or without some sedation) prior to the access and subsequent dilation procedure. This local anesthesia is preferably applied via standard techniques such as a needle injection to the canine fossa (CF) region, as well as at sites near the ostium of interest (preferably via transnasal injections). The patient may be lying or his or her back or, alternatively, the patient may be sitting in a chair much like that found in a dentists office. In yet another aspect, the patient may be under general anesthesia during the entire procedure.

Referring to FIG. 23, the cannula 20 has a secondary channel or lumen 30 through which a flexible endoscope 42 is positioned, with the distal end 48 advanced to the distal end or tip 26 of the cannula 20. The cannula 20 may be manipulated by advancing, rotating and sweeping until the maxillary ostium 134 is in view. In some instances it may be desirable to irrigate and/or aspirate the maxillary sinus cavity(s) prior to the dilation procedure. Such a procedure may be accomplished prior to insertion of the cannula 20, or alternatively, at the same time the cannula 20 is positioned within the sinus cavity of interest. For example, an irrigation and/or aspiration device (not shown) may be advanced through the main lumen 22 or secondary lumen 30 of the cannula 20, or performed as a separate procedure following known techniques.

Next, with reference to FIG. 24, once the ostium 134 is in view, a balloon dilation catheter 80 is positioned within the cannula 20. The balloon dilation catheter 80 may include an embodiment in which the distal tip 88 is curved so that it can be directed by rotation of the proximal portion 84 of the balloon dilation catheter 80. Once the distal tip 88 emerges from the main lumen 22 of the cannula 20, it can be visualized by the operator via the endoscope 42. Optional color patterns (not shown) can be provided on the distal tip 88 to aid in imaging. For example, one or more longitudinal stripes could be provided on the distal tip 88, to help identify it in the field of view of the endoscope 42. Additionally, the balloon 86 could be provided with a color tint or texture to help minimize light reflection in the field of view. Such light reflection may distract from the viewing of the distal tip 88. The distal tip 88 is manipulated across the ostium 134 by a combination of manipulations including advancement, rotation, cannula manipulations, and to-and-fro movements together with rotations. The objective here is to guide the distal tip 88 to and through the ostium 134 and infundibulum, and positioning the balloon 86 across the entire anatomical space (as illustrated in FIG. 24). Preferably the balloon 86 is long enough such that when it is inflated, a portion of the distal end of the balloon 86 is distally positioned past the edge of the uncinate process, and a portion of the proximal end of the balloon 86 proximally positioned relative to the maxillary sinus ostium 134. This positioning can be done via a visible mark placed on the balloon 86 (not shown) which can be placed at a desired location relative to the anatomy.

Once the distal tip 88 and balloon 86 are through the sinus ostium 134, it is preferable to orient the curve of the distal tip 88 in either a posterior or medial direction as opposed to an anterior, lateral, or superior direction. This is done because there are anatomical features in the superior/anterior part of the infundibulum that are desirable to avoid, such as the agger nasi cell or a recessus terminalus. Also, to position the distal tip 88 and some of the distal balloon 86 beyond the edge of the uncinate process often requires that the distal tip 88 be oriented medially to help guide the distal portion of the balloon 86 in the medial direction. The position of the distal tip 88 can optionally be confirmed via trans-nasal endoscopic imaging, using know tools and techniques. Alternatively, one or more radiopaque markers (not shown) on the balloon dilation catheter 80, within the balloon 86 could be utilized in conjunction with fluoroscopy to confirm the positioning of the balloon 86 prior to inflation.

With reference now to FIG. 25, once the balloon 86 is in a desired position, it is inflated by passing an inflation fluid through the inflation lumen 90. For example, a syringe or the like coupled to the proximal hub 84 may be used to forcibly pass inflation fluid into the interior of the balloon 86 to effectuate expansion. The inflation may optionally be witnessed by the endoscope 42. After a sufficient dilation pressure has been applied, for example, up to between about 4 and about 12 atmospheres of pressure, the balloon 86 is deflated and withdrawn back (proximally) into the lumen 22 of the cannula 20. The resulting dilation can then be directly viewed with the endoscope 42 to confirm a successful/unsuccessful dilation of the anatomy of interest. After viewing the site, the balloon 86 may have to be re-deployed across the anatomical site of interest for one or more dilation(s).

Figure 26:
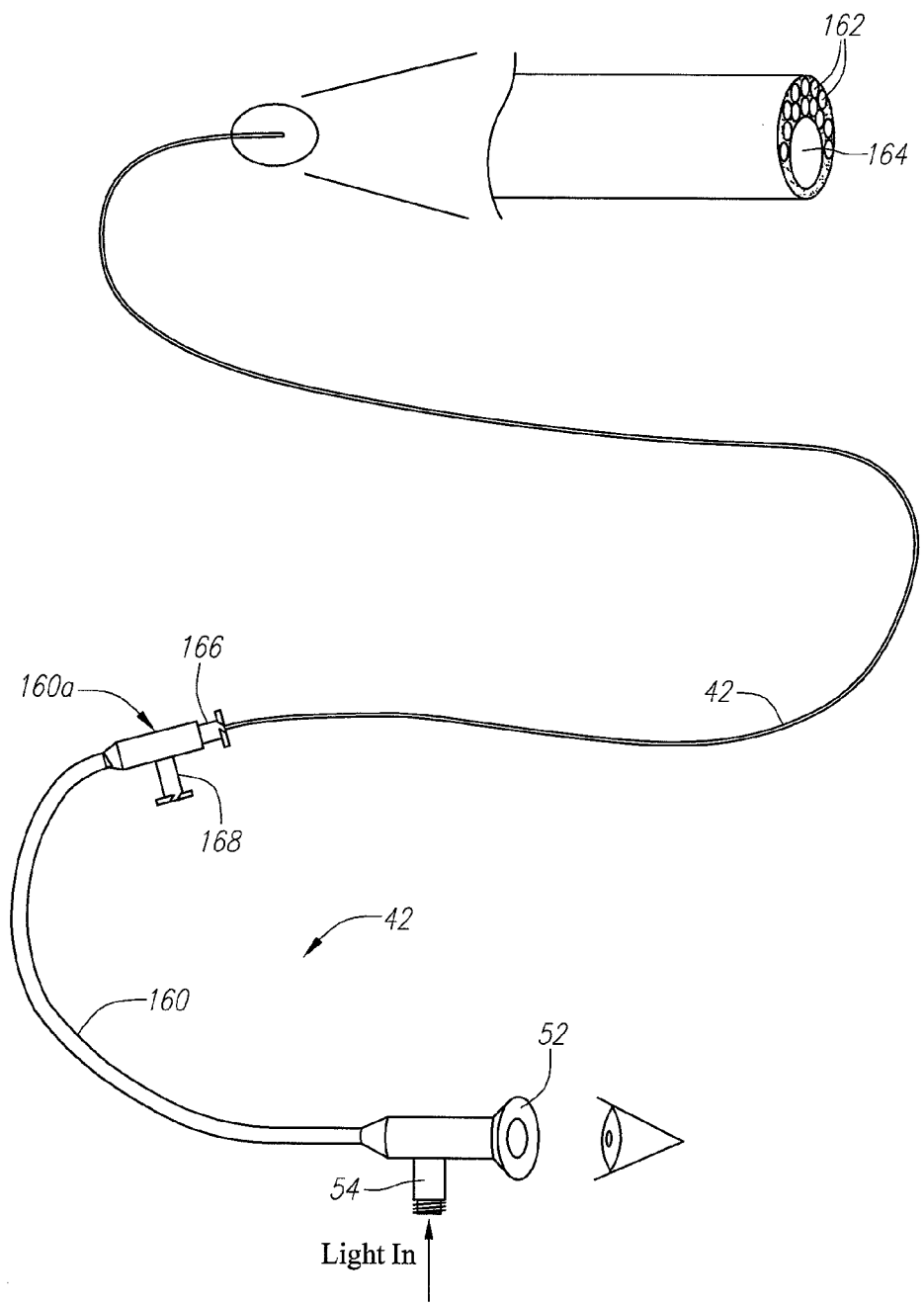
FIG. 26 illustrates one embodiment of an endoscope that is used in connection with one or more dilation procedures described herein.

FIG. 26 illustrates an exemplary flexible endoscope 42 (available from Storz as described herein) that may be used in connection with the dilation methods described herein. The flexible endoscope 42 may be usable in the primary or main lumen 22 of a cannula 20 or, alternatively, the flexible endoscope 42 may be adapted for passage through a secondary lumen 30 contained in or on a cannula 20. In yet another alternative, the flexible endoscope 42 may be adapted for use through a lumen 96 (as shown, for instance, in FIGS. 4A-4D, 5, 6A-6D, 7B and 7C) contained inside a balloon dilation catheter 80. The endoscope 42 may include a connector portion 160 that is flexible yet robust that connects a main portion of the endoscope 42 and a remotely located eyepiece 52. The eyepiece 52 may be viewed directly by a physician or, alternatively, the eyepiece may be coupled to a camera or imaging device for visualization on a separate monitor or the like (not shown in FIG. 26).

Still referring to FIG. 26, the endoscope 42 may include a connector 54 adjacent to the eyepiece 52 for coupling to a light source for illuminating the anatomical site of interest. Multiple light transmission fibers 162 (e.g., fiber optic fibers) may surround a fused quartz imaging bundle 164. The distal end 160a of the connector portion 160 may include a metallic manifold with multiple (e.g., two) Luer fittings 166, 168. One such fitting 166 surrounds the proximal end of the main endoscope portion 42 and the other 168 projections laterally which is fluid communication with the first Luer fitting 166.

FIG. 27 illustrates the endoscope 42 inserted into a cannula 20 that incorporates a secondary lumen 30 through which the endoscope 42 may pass. Since the overall length of the cannula 20 is considerably shorter than the length of the main portion of the endoscope 42, a significant length of "exposed" endoscope 42 extends between the manifold or connector 160 of the endoscope 42 and the proximal end or hub 31 of the secondary lumen 30. The proximal hub 31 may have a funnel shape such as provided by a female Luer fitting and an optional Tuohy Borst valve (not shown). While this arrangement of the endoscope 42 and cannula 20 is useable, the exposed endoscope 42 is somewhat fragile and vulnerable to damage or fracture if it is inadvertently kinked, buckled, or crushed during handling or manipulation.

Consequently, in order to help protect the endoscope 42 during handling and manipulation, a protective sleeve 180 can be provided, as shown in FIG. 27B. The protective sleeve 180 is flexible enough to not interfere with the routine handling of the endoscope 42 and cannula 20 during the procedure, yet is able to prevent the main portion of the endoscope 42 from kinking, buckling, or crushing. The length of the protective sleeve 180 may be tailored to cover the full length of what would have been exposed between the manifold 160a of the endoscope 42 and the proximal hub 31 of the cannula 20, when the endoscope 42 is fully inserted into the secondary lumen 30 during use.

In use, the endoscope 42 would first be inserted into the proximal end 180a of the protective sheath 180. A portion of the endoscope 42 would emerge and extend distally of the distal end 180b of the protective sheath 180. The proximal end 180a of the sheath 180 would then be secured to the manifold 160a of the endoscope, such as via the Luer connector 166 or the like. The distal portion 180b of the endoscope 180 may then be inserted into the secondary lumen 30 of the cannula 20. When the distal end 48 of the endoscope 42 is at the desired position at the distal end of the secondary lumen 30, the distal end 180b of the protective sheath is secured to the proximal hub 31, such as by a Luer connection. In this manner, the full length of the relatively fragile endoscope 42 is protected for the duration of the procedure. When the procedure is complete (e.g., after the patient's sinus ostia have been dilated), the sleeve 180 can be disconnected from the cannula 20. In general, the endoscope 42 is a reusable and re-sterilizable device, while the other devices or sub-components described herein may be disposable, such as the cannula 20 and the balloon dilation catheter 80. The protective sleeve 180 may be left in place to keep the majority of the fragile portion of the endoscope 42 protected during re-sterilization and storage until it is needed for a next procedure. The endoscope 42 can be re-sterilized with the protective sleeve 180 in place. The Luer fitting 168 can be utilized to infuse cold sterilant (such as used in a Steris™ device) through the inside of the protective sleeve 180 and the outside of the endoscope 42.

FIG. 27B also illustrates a version of the protective sleeve 180 in which the sleeve is formed from nesting halves 180a, 180b. As seen in FIG. 27B, the distal half 180b is dimensioned to pass within a lumen or channel of the proximal half 180a. In this regard, the overall length of the protective sleeve 180 may be varied. The two halves 180a, 180b may include telescoping nesting tubes which can be moved axially with respect to one another to adjust the overall length.

As seen in FIG. 28A, the proximal half 180*a* may include an internal detent or rib 182 that engages with a flange 184 on the end of the distal half 180*b* of the protective sleeve 180. The internal detent or rib 182 limits axial movement of the distal half 180*b* within the lumen or channel of the proximal half 180*a*. In addition, if multiple the detents or ribs 182 are used (as shown in FIG. 28A) these can be used to lock the protective sleeve 180 in a collapsed state. In this initial position, the endoscope 42 would be inserted into the sleeve 180, emerging and extending from the distal end 180*b*. Once the endoscope 42 is in a desired position at the distal end of the secondary lumen 30, the distal end of the sleeve 180 is secured to the proximal hub 31 of the endoscope 42. If necessary, the length of the protective sleeve 180 may be extended to facilitate this connection.

At the end of the procedure, the sleeve 180 may be removed from the cannula 20. The sleeve 180 can then be extended to an extended position, which preferably is at least long enough to cover the entire length of the fragile portion of the endoscope 42. One or more detents or ribs 182 on the inner surface at the distal end of the proximal half of the sleeve 180*a* prevent the distal portion of the sleeve 180*b* from completely separating from the proximal half 180*a*. The endoscope 42 together with the protective sleeve 180 can then be re-sterilized and stored together. At the start of the next procedure, the protective sleeve 180 may be contracted in length to allow for insertion of the endoscope 42 into the secondary lumen 30.

Figure 29:
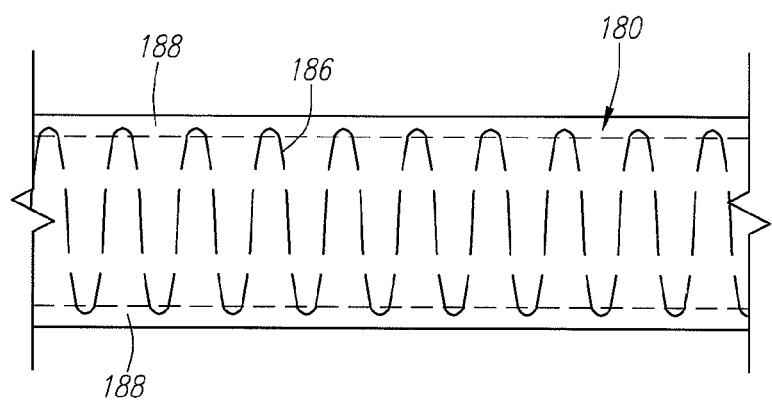
FIG. 29 illustrates one embodiment of a protective sleeve using a coil-embedded structure.
Figure 30:
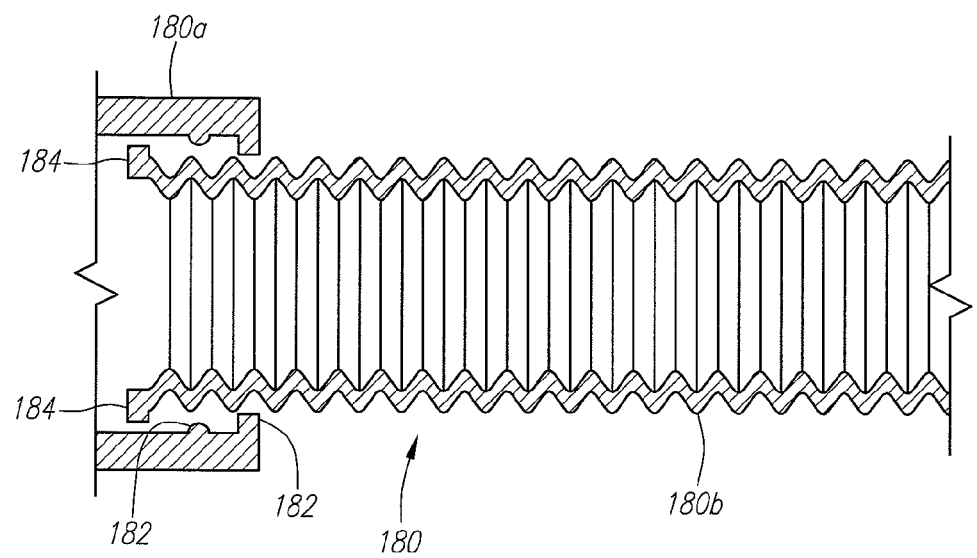
FIG. 30 illustrates another embodiment of a protective sleeve that uses a corrugated structure.

The tube(s) that comprise the protective sleeve 180 may be flexible yet kink resistant. For example, FIG. 29 illustrates one embodiment in which the tube 188 forming the protective sleeve 180 is includes a coil-embedded structure, wherein a coil 186 is embedded into the wall of a flexible polymeric tubular material 188. In another embodiment, as illustrated in FIG. 30, at least one of the tube(s) 188 that comprise the protective sleeve 180 can also have a corrugated construction.

The embodiments described above for a protective sleeve 180 are useful in conjunction with the above-mentioned Storz endoscope 42 (or other flexible endoscopes 42) which have length of relatively fragile small diameter portion that is longer than the secondary lumen 30 on or within the cannula 20. The protective sleeve 180 thus protects the fragile portion of the endoscope 42 that is not within the secondary lumen 30. Alternatively, it is also possible to tailor the length of the fragile portion of the endoscope 42 to match the length of the secondary lumen 30. The manifold 160*a* on the endoscope 42 can then be directly connected to the proximal end of the endoscope 42, for instance, by Luer fittings. Further still, the optical components in the fragile portion of the endoscope 42 including the light input fibers 162, fused imaging bundle 164 and lens could be permanently secured and sealed within the secondary lumen 30 of cannula 20. The cannula 20 together with the endoscope 42 would then preferably be an integrated reusable and re-sterilizable structure.

Figure 31:
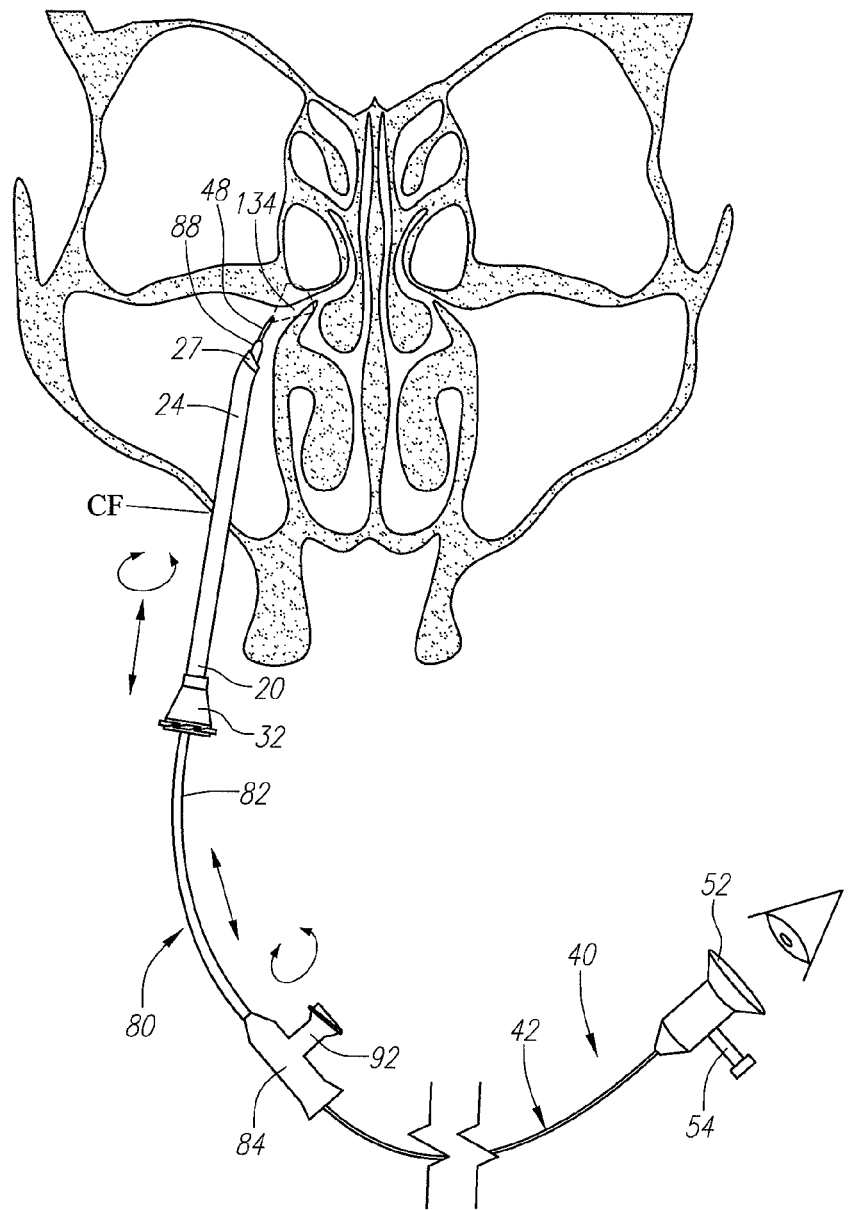
FIG. 31 illustrates a coronal cross-section view of the body structure of the skull defining the sinus cavities with an alternative embodiment of a balloon catheter, endoscope and cannula accessing the ostium of a sinus cavity via the canine fossa.

FIG. 31 illustrates another embodiment of treating sinusitis in which the endoscope 42 is advanced through a lumen 96 (hidden from view in FIG. 31) contained in the balloon dilation catheter 80. FIG. 31 illustrates a cannula 20 placed in the artificially created opening or passage in the canine fossa CF region. The distal tip 88 of the balloon dilation catheter 80 is shown emerging from the distal tip 26 of the cannula 20. Also, FIG. 31 illustrates the distal end 48 of the endoscope 42 projecting distally from the distal tip 88 of the balloon dilation catheter 80. The imaging field of view is shown by the dashed conical portion extending toward the patient's ostium 134. As seen in FIG. 31, location and positioning of the balloon dilation catheter 80 and endoscope 42 may be accomplished by a series of twisting, rotational, and axial movements of both the cannula 20 and the balloon dilation catheter 80.

While embodiments of the present invention have been shown and described, various modifications may be made without departing from the scope of the present invention. The invention, therefore, should not be limited, except to the following claims, and their equivalents.

What is claimed is:

1. A method of dilating an anatomical region in a patient comprising:
    forming an artificial access passageway into a canine fossa of the patient with a piercing tool that includes a removable sheath disposed on a distal portion of the piercing tool;
    positioning a cannula within the access passageway and the removable sheath, the cannula having a first lumen adapted for passage of a balloon dilation catheter, and a secondary lumen adapted for a visualization tool;
    visualizing the anatomical region of interest with the visualization tool located within the secondary lumen;
    inserting the balloon dilation catheter into the first lumen and advancing the same so as to place the dilation balloon in or across the anatomical region of interest; and
    dilating the dilation balloon.

2. The method of claim 1, wherein the piercing tool includes a stopping surface positioned at a location that is closer to a distal end of the piercing tool than a proximal end of the piercing tool.

3. The method of claim 1, wherein the piercing tool is removed from the artificial access passageway and the removable sheath is left in the artificial access passageway.

4. The method of claim 1, wherein the sheath extends through the artificial access passageway and a distal portion of the cannula is directed through the sheath and into the sinus cavity.

5. The method of claim 1, wherein the balloon dilation catheter includes a curved distal tip.

6. The method of claim 1, wherein the visualization tool is permanently sealed within the secondary lumen.

7. The method of claim 1, further including suctioning material from the sinus cavity through the cannula.

8. The method of claim 1, wherein the sinus cavity is a maxillary sinus cavity.

9. The method of claim 1, wherein the balloon dilation catheter is directed through the artificial access passageway, through the sinus cavity, and in or across the anatomical region of interest before dilating.

10. The method of claim 9, wherein sinus cavity is the maxillary sinus cavity and the anatomical region of interest includes a maxillary sinus ostium.

11. A method of dilating an anatomical region in a patient comprising:
    forming an artificial access passageway through a canine fossa region and into a maxillary sinus cavity with a piercing tool, wherein the piercing tool includes a removable sheath disposed on a distal portion of the piercing tool;
    positioning a cannula within the artificial access passageway, the cannula including a first lumen adapted for passage of a balloon dilation catheter and a secondary lumen that includes a visualization tool;
    directing a distal portion of a balloon dilation catheter through the removable sheath and into the maxillary sinus cavity;
    directing the distal portion of the balloon dilation catheter across at least a portion of a drainage pathway of the maxillary sinus cavity, wherein the distal portion of the balloon dilation catheter includes an inflatable balloon; and inflating the balloon to dilate the portion of the drainage pathway of the maxillary sinus cavity.

12. The method of claim 11, further including directing the cannula through the sheath and into the maxillary sinus cavity before the distal portion of the balloon dilation catheter is directed through the removable sheath.

13. The method of claim 12, wherein an endoscope is positioned within the first lumen and wherein the distal portion of the balloon dilation catheter is directed through the second lumen and into the maxillary sinus cavity.

14. The method of claim 13, wherein the distal portion of the balloon dilation catheter is visualized with the endoscope as it is directed across the portion of the drainage pathway of the maxillary sinus cavity.

15. The method of claim 13, wherein the endoscope is permanently sealed within the first lumen.

16. The method of claim 11, wherein the balloon dilation catheter includes a curved distal tip.

17. The method of claim 11, further including suctioning material from the maxillary sinus cavity through the cannula.

18. The method of claim 11, wherein the portion of the drainage pathway of the maxillary sinus cavity includes a maxillary sinus ostium.

\* \* \* \* \*